(12) United States Patent
Guy et al.

(10) Patent No.: US 9,416,124 B2
(45) Date of Patent: Aug. 16, 2016

(54) SUBSTITUTED 2-ALKYL-1-OXO-N-PHENYL-3-HETEROARYL-1,2,3,4-TETRAHYDRO-ISOQUINOLINE-4-CARBOXAMIDES FOR ANTIMALARIAL THERAPIES

(75) Inventors: Rodney Kiplin Guy, Memphis, TN (US); Fangyi Zhu, Memphis, TN (US); Wendyam Armand Guiguemde, Memphis, TN (US); David Floyd, Pennington, NJ (US); Spencer Knapp, Skillman, NJ (US); Philip Stein, Pennington, NJ (US); Steve Castro, East Hannover, NJ (US)

(73) Assignees: ST. JUDE CHILDREN'S RESEARCH HOSPITAL, Memphis, TN (US); MMV MEDICINES FOR MALARIA VENTURE, Geneva (CH); RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 12 days.

(21) Appl. No.: 14/240,994

(22) PCT Filed: Aug. 24, 2012

(86) PCT No.: PCT/IB2012/054305
§ 371 (c)(1),
(2), (4) Date: Feb. 25, 2014

(87) PCT Pub. No.: WO2013/027196
PCT Pub. Date: Feb. 28, 2013

(65) Prior Publication Data
US 2014/0235593 A1 Aug. 21, 2014

Related U.S. Application Data

(60) Provisional application No. 61/527,594, filed on Aug. 25, 2011.

(51) Int. Cl.
| | |
|---|---|
| *C07D 401/04* | (2006.01) |
| *C07D 409/04* | (2006.01) |
| *C07D 417/04* | (2006.01) |
| *A61K 31/4725* | (2006.01) |
| *A61K 31/506* | (2006.01) |
| *A61K 45/06* | (2006.01) |

(52) U.S. Cl.
CPC .......... *C07D 401/04* (2013.01); *A61K 31/4725* (2013.01); *A61K 31/506* (2013.01); *A61K 45/06* (2013.01); *C07D 409/04* (2013.01); *C07D 417/04* (2013.01)

(58) Field of Classification Search
None
See application file for complete search history.

(56) References Cited

U.S. PATENT DOCUMENTS

2005/0197353 A1  9/2005  Ritzeler et al.

FOREIGN PATENT DOCUMENTS

| | | |
|---|---|---|
| CA | 2 519 658 | 10/2004 |
| DE | 103 12 963 | 10/2004 |
| WO | WO 95/21616 | 8/1995 |
| WO | WO 03/044021 | 5/2003 |
| WO | WO 2004/004727 | 1/2004 |
| WO | WO 2004/022553 | 3/2004 |
| WO | WO 2006/104915 | 10/2006 |
| WO | WO 2007/105989 | 9/2007 |
| WO | WO 2010/055164 | 5/2010 |

OTHER PUBLICATIONS

Jordan, V. C. Nature Reviews: Drug Discovery, vol. 2, 2003, pp. 205-213.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Vippagunta, et al. Advanced Drug Delivery Reviews, 48, 2001, pp. 3-26.*
Guiguemde, W. A. et al. "Chemical genetics of *Plasmodium falciparum*" *Nature*, May 20, 2010, pp. 311-315, vol. 465.
Database Registry [Online] Chemical Abstracts Service, Accession Nos. RN 891918-34-6, RN 891911-97-0, RN 891923-28-7, RN 891923-04-9, RN 891901-26-1, Jul. 11, 2006, XP002686412, pp. 1-5.
Database Registry [Online] Chemical Abstracts Service, Accession No. RN 931315-35-4, Apr. 20, 2007, XP002686905, p. 1.
Database Registry [Online] Chemical Abstracts Service, Accession No. RN 931939-58-1, Apr. 23, 2007, XP002686906, p. 1.
Madrid, P. B. et al. "Synthesis of ring-substituted 4-aminoquinolines and evaluation of their antimalarial activities" *Bioorganic & Medicinal Chemistry Letters*, 2005, pp. 1015-1018, vol. 15.
Written Opinion in International Application No. PCT/IB2012/054305, Nov. 20, 2012, pp. 1-9.
Chaturvedi, D., et al., "Artemisinin and its derivatives: a novel class of anti-malarial and anti-cancer agents," *Chemical Society Reviews*, 2010, vol. 39, pp. 435-454.
Eastman, R.T., et al., "Artemisinin-based combination therapies: a vital tool in efforts to eliminate malaria," *Nature Reviews Microbiology*, Dec. 2009, vol. 7, pp. 864-874.
Gutema, G.B., et al., "Combination Therapy and Its Implication on Clinical Efficacy of Artemisinins—Review," *International Journal of Pharmaceutical Sciences and Research*, 2011, vol. 2, No. 8, pp. 1914-1921.
Mu, J., et al., "*Plasmodium falciparum* genome-wide scans for positive selection, recombination hot spots and resistance to antimalarial drugs," *Nature Genetics*, Mar. 2010, vol. 42, No. 3, pp. 268-272.
White, N.J., "Qinghaosu (Artemisinin): The Price of Success," *Science*, Apr. 18, 2008, vol. 320, pp. 330-334.
Jimenez-Diaz, M.B. et al. "(+)=SJ733, a clinical candidate for malaria that acts through ATP4 to induce rapid host-mediated clearance of *Plasmodium*" *PNAS*, Dec. 1, 2014, vol. 112, No. 42, pp. E5455-E5462 and corrected p. E5764.

* cited by examiner

Primary Examiner — James D Anderson
(74) Attorney, Agent, or Firm — Saliwanchik, Lloyd & Eisenschenk

(57) ABSTRACT

In one aspect, the invention relates to novel substituted 2-alkyl-1-oxo-N-phenyl-3-heteroaryl -1,2,3,4-tetrahydroisoquinoline-4-carboxamides; synthetic methods for making the compounds; pharmaceutical compositions comprising the compounds; and methods of treating and/or preventing malaria. This abstract is intended as a scanning tool for purposes of searching in the particular art and is not intended to be limiting of the present invention.

12 Claims, 2 Drawing Sheets

Reference compound 1247

| Compound | In vitro | | | In vivo – oral mouse | | | |
|---|---|---|---|---|---|---|---|
| | EC$_{50}$ (nM) | Sol (µM) | T$_{1/2}$ (hr) | Clint (ml/min/kg) | Cmax (µM) | AUC (µg-hr/ml) | T$_{1/2}$ (hr) |
| Reference compound 1247* (racemate) | 12 | 0.5 | 2.6 | 8 | 0.12 | 0.48 | 1.8 |
| Compound 6** (racemate) | 54 | 54 | >4 | 1.0 | 10 | 27 | 1.8 |
| Compound 2*** | 41 | 66 | >4 | 1.0 | 11 | 37 | 4.2 |

Notes: *oral data @ 300 mg/Kg; oral data @ 50mg/Kg; *oral data@100 mg/kg

A

B

SUBSTITUTED 2-ALKYL-1-OXO-N-PHENYL-3-HETEROARYL-1,2,3,4-TETRAHYDRO-ISOQUINOLINE-4-CARBOXAMIDES FOR ANTIMALARIAL THERAPIES

CROSS-REFERENCE TO RELATED APPLICATIONS

This application is the U.S. national stage application of International Patent Application No. PCT/IB2012/054305, filed Aug. 24, 2012, which claims the benefit of U.S. Provisional Patent Application No. 61/527,594, filed Aug. 25, 2011.

FIELD OF THE INVENTION

The present invention relates to novel anti-malarial agents. Specifically, the present invention is related to agents useful for the preparation of a pharmaceutical formulation for preventing or treating malaria and methods of their use and manufacture.

BACKGROUND

Malaria is a devastating infectious disease caused by the protozoa *Plasmodium falciparum*. Malaria affects about 200-500 million people worldwide annually, killing almost 1% of those infected (Madrid et al., Synthesis of ring-substituted 4-aminoquinolines and evaluation of their antimalarial activities, Bioorg. Med. Chem. Lett., 2005, 15, 1015-8). Four species of *Plasmodium* infect humans, the most deadly of these being *P. falciparum*. Most deaths occur due to a complication of infections with *P. falciparum*, wherein erythrocytes infected with mature-stage parasites adhere to the vascular endothelium of post-capillary venules. Vascular occlusion and/or an inappropriate host immune reaction can lead to coma. Once a coma is established, the subject usually has only a 10-50% chance of survival, even with appropriate medical attention.

Malarial drug resistance is largely responsible for the current epidemic and thus the discovery of new effective antimalarial agents is needed. Quinoline-based therapies are commonly used for the treatment of malaria. However, because of their widespread use, many malaria parasites are now resistant to traditional quinoline-based therapies. Drug resistance to the commonly used malaria drug, Chloroquine (CQ), for example, is so widespread that the drug is virtually useless in some parts of the world. Although numerous small molecules demonstrating superior antimalarial properties are regularly being discovered, most of these compounds fail to reach the clinic in part due to their poor pharmacokinetic and toxicity profiles. Thus, it is imperative that new anti-malarial strategies be developed, and in particular, new therapies that are effective against drug-resistant malaria. The present application addresses this need.

SUMMARY

In accordance with the purpose(s) of the invention, as embodied and broadly described herein, the invention, in one aspect, relates to compounds useful as malarial therapies, methods of making the same, pharmaceutical compositions comprising the same, and methods of treating and/or preventing malaria.

Disclosed are compounds having a structure represented by formula (I) or (II) as described herein or a pharmaceutically acceptable salt, hydrate, solvate, or polymorph thereof, as well as tautomers, geometrical isomers, or optically active forms thereof.

Also disclosed are pharmaceutical compositions comprising a therapeutically effective amount of one or more disclosed compounds, or a pharmaceutically acceptable salt, hydrate, solvate, or polymorph thereof, as well as tautomers, geometrical isomers, or optically active forms thereof and a pharmaceutically acceptable carrier.

Also disclosed are methods for preparing the disclosed compounds and corresponding synthesis intermediates.

Also disclosed are methods of using the disclosed compounds: methods for the treatment of malaria, methods for the prevention of malaria, and methods for inactivating parasitic infection.

Also disclosed are methods for manufacturing a medicament comprising combining at least one disclosed compound, or pharmaceutically acceptable salt, hydrate, solvate, or polymorph thereof, as well as tautomers, geometrical isomers, or optically active forms thereof or at least one disclosed product with a pharmaceutically acceptable carrier or diluent.

Also disclosed are kits comprising a disclosed compound or a product of a disclosed method and one or more of: at least one agent known to prevent malaria; at least one agent known to treat malaria; or instructions for treating malaria.

Also disclosed is a use of at least one disclosed compound, or pharmaceutically acceptable salt, hydrate, solvate, or polymorph thereof, as well as tautomers, geometrical isomers, or optically active forms thereof for the manufacture of a pharmaceutical preparation for the prevention or treatment of malaria.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

DESCRIPTION

Figure 1:
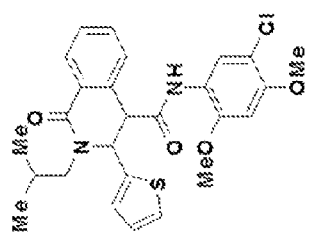
FIG. 1 shows the in vitro potency and in vitro and in vivo pharmacokinetic properties of a reference compound (1247) and two compounds of the invention (compound 2 and compound 6) assayed as described in Methods 6 and 8.

The present invention can be understood more readily by reference to the following detailed description of the invention and the Examples included herein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

References in the specification and concluding claims to parts by weight of a particular element or component in a composition denote the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" mean that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal, for example, a primate (e.g., human). A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where "reduce", "inhibit" or "prevent" are used herein, unless specifically indicated otherwise, the use of the other two words is also expressly disclosed. As used herein, the term "diagnosed" means having been subjected to a physical examination by a person of skill, for example, a physician, and found to have a condition that can be diagnosed or treated by the compounds, compositions, or methods disclosed herein.

As used herein, the phrase "identified to be in need of treatment for a disorder," or the like, refers to selection of a subject based upon need for treatment of the disorder. For example, a subject can be identified as having a need for treatment of a disorder based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target receptor, or other biological entity together in such a manner that the compound can affect the activity of the target (e.g., subject, cell, etc.), either directly (i.e., by interacting with the target itself), or indirectly (i.e., by interacting with another molecule, co-factor, factor, or protein on which the activity of the target is dependent).

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "pro-phylactically effective amount"; that is, an amount effective for prevention of a disease or condition. The term "effective amount" includes "prophylaxis-effective amount" as well as "treatment-effective amount".

The term "prophylaxis-effective amount" refers to a concentration of a compound of this invention that is effective in inhibiting, decreasing the likelihood of the disease by malarial parasites, preventing malarial infection or preventing the delayed onset of the disease by malarial parasites, when administered before infection, i.e. before, during and/or slightly after the exposure period to malarial parasites.

The term "prophylaxis" includes causal prophylaxis (i.e., antimalarial activity comprising preventing the pre-erythrocytic development of the parasite), suppressive prophylaxis (i.e., antimalarial activity comprising suppressing the development of the blood stage infection) and terminal prophylaxis (i.e., antimalarial activity comprising suppressing the development of intra-hepatic stage infection). This term includes primary prophylaxis (i.e., preventing initial infection) where the antimalarial compound is administered before, during and/or after the exposure period to malarial parasites and terminal prophylaxis (i.e., to prevent relapses or delayed onset of clinical symptoms of malaria) when the antimalarial compound is administered towards the end of and/or slightly after the exposure period to malarial parasites but before the clinical symptoms. Typically, against *P. falciparum* infections, suppressive prophylaxis is used whereas against *P. vivax* or a combination of *P. falciparum* and *P. vivax*, terminal prophylaxis is used.

Likewise, the term "treatment-effective amount" refers to a concentration of a compound that is effective in treating malaria infection, e.g., leads to a reduction in parasite numbers in blood following microscopic examination when administered after infection has occurred.

As used herein, "$EC_{50}$," is intended to refer to the concentration of a substance (e.g., a compound or a drug) that is required for 50% perturbation of a biological process, or component of a process, including a protein, subunit, organelle, ribonucleoprotein, etc. in vitro. In one aspect, an $EC_{50}$ ($ED_{50}$ is generally used for in vivo and describes the dose in mg/Kg given to cause a 50% effect; $ED_{90}$ refers to a 90% effect) can refer to the concentration of a substance that is required for 50% perturbation in vivo, as further defined elsewhere herein. In a further aspect, $EC_{50}$ refers to the concentration of agonist that provokes a response halfway between the baseline and maximum response. In yet a further aspect, the response is in vitro.

As used herein, "$IC_{50}$" is intended to refer to the concentration of a substance (e.g., a compound or a drug) that is required for 50% inhibition of a biological process, or component of a process, including a protein, subunit, organelle, ribonucleoprotein, etc. In one aspect, $IC_{50}$ can refer to the concentration of a substance that is required for 50% inhibition in vivo, as further defined elsewhere herein. In a further aspect, $IC_{50}$ refers to the half maximal (50%) inhibitory concentration (IC) of a substance. In yet a further aspect, the inhibition is measured in vitro.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and, based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with the permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $-(CH_2)_a-$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like.

The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula $-C(O)H$. Throughout this specification "C(O)" is a shorthand notation for a carbonyl group, i.e., C=O.

The terms "amine" or "amino" as used herein are represented by the formula $-NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula $-NH(-alkyl)$ where alkyl is as described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula $-N(-alkyl)_2$ where alkyl is as described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula $-C(O)OH$.

The term "ester" as used herein is represented by the formula $-OC(O)A^1$ or $-C(O)OA^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula $-(A^1O$ (O)C-A$^2$-C(O)O)$_a$— or —(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula —(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle" as used herein refers to single and multi-cyclic aromatic or non-aromatic ring systems in which at least one of the ring members is other than carbon. Heterocycle includes azetidine, dioxane, furan, imidazole, isothiazole, isoxazole, morpholine, oxazole, oxazole (including 1,2,3-oxadiazole, 1,2,5-oxadiazole and 1,3,4-oxadiazole), piperazine, piperidine, pyrazine, pyrazole, pyridazine, pyridine, pyrimidine, pyrrole, pyrrolidine, tetrahydrofuran, tetrahydropyran, tetrazine (including 1,2,4,5-tetrazine), tetrazole (including 1,2,3,4-tetrazole and 1,2,4,5-tetrazole), thiadiazole (including 1,2,3-thiadiazole, 1,2,5-thiadiazole, and 1,3,4-thiadiazole), thiazole, thiophene, triazine (including 1,3,5-triazine and 1,2,4-triazine), triazole (including 1,2,3-triazole and 1,3,4-triazole), and the like. The term "hydroxyl" as used herein is represented by the formula —OH.

The term "ketone" as used herein is represented by the formula A$^1$C(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —N$_3$.

The term "nitro" as used herein is represented by the formula —NO$_2$.

The term "nitrile" as used herein is represented by the formula —CN.

The term "silyl" as used herein is represented by the formula —SiA$^1$A$^2$A$^3$, where A$^1$, A$^2$, and A$^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, —S(O)$_2$A$^1$, —OS(O)$_2$A$^1$, or —OS(O)$_2$OA$^1$, where A$^1$ can be hydrogen or an alkyl, cycloalkyl, alkenyl, cycloalkenyl, alkynyl, cycloalkynyl, aryl, or heteroaryl group as described herein. Throughout this specification "S(O)" is a shorthand notation for S═O. The term "sulfonyl" is used herein to refer to the sulfo-oxo group represented by the formula —S(O)$_2$A$^1$, where A$^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH. "R$^1$," "R$^2$," "R$^3$," "R$^n$," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. It is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —(CH$_2$)$_{0-4}$R$^\circ$; —(CH$_2$)$_{0-4}$OR$^\circ$; —O(CH$_2$)$_{0-4}$R$^\circ$, —O—(CH$_2$)$_{0-4}$C(O)OR$^\circ$; —(CH$_2$)$_{0-4}$CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH═CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NR$^\circ$$_2$; —N(R$^\circ$)C(S)NR$^\circ$$_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ$$_2$ ; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ$$_3$; —(CH$_2$)$_{0-4}$OC(O)R$^\circ$; —OC(O)(CH$_2$)$_{0-4}$SR—; SC(S)SR$^\circ$; —(CH$_2$)$_{0-4}$SC(O)R$^\circ$; —(CH$_2$)$_{0-4}$C(O)NR$^\circ$$_2$; —C(S)NR$^\circ$$_2$; —C(S)SR$^\circ$; —SC(S)SR$^\circ$; —(CH$_2$)$_{0-4}$OC(O)NR$^\circ$$_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NR$^\circ$$_2$; —(CH$_2$)$_{0-4}$S(O)R$^\circ$; —N(R$^\circ$)S(O)$_2$NR$^\circ$$_2$; —N(R$^\circ$)S(O)$_2$R$^\circ$; —N(OR$^\circ$)R$^\circ$; —C(NH)NR$^\circ$$_2$; —P(O)$_2$R$^\circ$; —P(O)R$^\circ$$_2$; —OP(O)R$^\circ$$_2$; —OP(O)(OR$^\circ$)$_2$; SiR$^\circ$$_3$; —(C$_{1-4}$ straight or branched alkylene)O—N(R$^\circ$)$_2$; or —(C$_{1-4}$ straight or branched alkylene)C(O)O—N(R$^\circ$)$_2$, wherein each R$^\circ$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6—membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12—membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —$(CH_2)_{0-2}R^•$, —(haloR$^•$), —$(CH_2)_{0-2}OH$, —$(CH_2)_{0-2}OR^•$, —$(CH_2)_{0-2}CH(OR^•)_2$, —$O(haloR^•)$, —CN, —$N_3$, —$(CH_2)_{0-2}C(O)R^•$, —$(CH_2)_{0-2}C(O)OH$, —$(CH_2)_{0-2}C(O)OR^•$, —$(CH_2)_{0-2}SR^•$, —$(CH_2)_{0-2}SH$, —$(CH_2)_{0-2}NH_2$, —$(CH_2)_{0-2}NHR^•$, —$(CH_2)_{0-2}NR^•_2$, —$NO_2$, —$SiR^•_3$, —$OSiR^•_3$, —$C(O)SR^•$, —($C_{1-4}$ straight or branched alkylene)$C(O)OR^•$, or —$SSR^•$, wherein each R$^•$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6—membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, $C_{1-6}$ aliphatic which may be substituted as defined below, or an unsubstituted 5-6—membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include —O(CR*$_2$)$_{2-3}$O—, wherein each independent occurrence of R* is selected from hydrogen, $C_{1-6}$ aliphatic which may be substituted as defined below, or an unsubstituted 5-6—membered saturated, partially unsaturated, or aryl ring having 0-4 heteroatoms independently selected from nitrogen, oxygen, or sulfur.

Suitable substituents on the aliphatic group of R* include halogen, —R$^•$, —(haloR$^•$), —OH, —OR$^•$, —O(haloR$^•$), —CN, —C(O)OH, —C(O)OR$^•$, —$NH_2$, —NHR$^•$, —NR$^•_2$, or —$NO_2$, wherein each R$^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6—membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$, wherein each R$^†$ is independently hydrogen, $C_{1-6}$ aliphatic which may be substituted as defined below, unsubstituted —OPh, or an unsubstituted 5-6—membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s), form an unsubstituted 3-12—membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, R$^•$ are independently halogen, —R$^•$, —(haloR$^•$), —OH, —OR$^•$, —O(haloR$^•$), —CN, —C(O)OH, —C(O)OR$^•$, —$NH_2$, —NHR$^•$, —NR$^•_2$, or —$NO_2$, wherein each R$^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6—membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, brosylate, and halides.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited to alkyl or substituted alkyls, alkoxy or substituted alkoxy, mono or di-substituted amino, amide groups, etc. Organic residues can preferably comprise 1 to 18 carbon atoms, 1 to 15 carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15 carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims refers to a fragment, group, or substructure of a molecule described herein, regardless of how the molecule is prepared. For example, a 2,4-thiazolidinedione radical in a particular compound has the structure

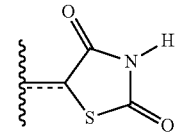

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkyl sulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four, inorganic atoms as listed above bonded together. Examples of inorganic radicals include, but are not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radicals. Inorganic radicals do not comprise metalloid elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light (optical rotation, denoted by $[\alpha]_D$) by the compound, with (−) or l meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines (bonds to atoms below the plane). When specified, the Cahn-Ingold-Prelog system can be used to assign the (R) or (S) configuration to a chiral carbon although, unless specifically defined, the indication of atoms above or below the plane does not necessarily imply a definition of absolute configuration.

According to one particular aspect of the invention, compounds of the invention encompass racemates with trans stereochemistry.

According to another particular aspect of the invention, compounds of the invention are dextrorotatory (d) and have a (+)-sign of optical rotation.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from an aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates; see, e.g., "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

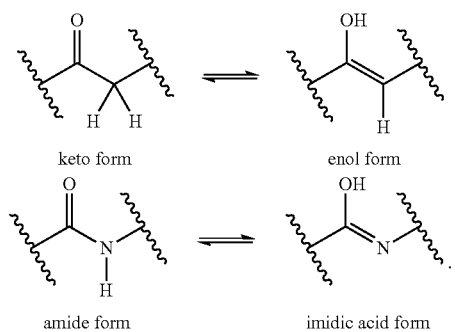

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

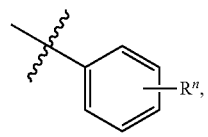

which is understood to be equivalent to a formula:

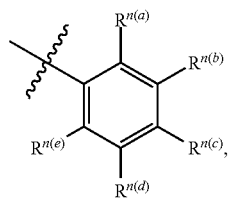

wherein n is typically an integer. That is, $R''$ is understood to represent five independent substituents, $R''^{(a)}$, $R''^{(b)}$, $R''^{(c)}$, $R''^{(d)}$, $R''^{(e)}$. By "independent substituents," it is meant that each R substituent can be independently defined. For example, if in one instance $R''^{(a)}$ is halogen, then $R''^{(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed, while specific reference to each various individual and collective combination and permutation of these compounds cannot be explicitly disclosed, each is specifically contemplated and described herein. For example, if a particular compound is disclosed and discussed and a number of modifications that can be made to a number of molecules including the compound are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D, is disclosed, then even if each is not individually recited each is individually and collectively contemplated, meaning combinations A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds having a structure represented by a formula:

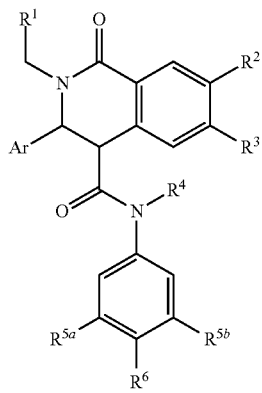

wherein Ar is monocyclic heteroaryl selected from 2-thiopheneyl, 3-thiopheneyl, 2-furanyl, 3-furanyl, imidazolyl, isoxazolyl, pyrazolyl, thiazolyl, isothiazolyl, 2-pyridinyl, 3-pyridinyl, 4-pyridinyl, pyrimidinyl, and pyridazinyl and, valence permitting, is substituted with 0-3 groups selected from fluoro, chloro, bromo, iodo, cyano, methyl, trifluoromethyl, methoxyl, and ethoxyl; wherein $R^1$ is selected from hydrogen, methyl, ethyl, n-propyl, i-propyl, cyclopropyl, n-butyl, i-butyl, s-butyl, t-butyl, and cyclobutyl and, valence permitting, is substituted with 0-3 groups selected from fluoro, chloro, bromo, iodo, cyano, methoxyl, and ethoxyl; wherein $R^2$ and $R^3$ are independently selected from hydrogen, C1-C4 alkyl, C1-C4 alkoxyl, cyano, fluoro, chloro, bromo, and iodo; wherein $R^4$ is hydrogen, C1-C4 alkyl, or a hydrolysable residue; wherein $R^{5a}$ and $R^{5b}$ are independently selected from hydrogen, fluoro, chloro, bromo, iodo, cyano, C1-C4 alkyl, C1-C4 haloalkyl, C1-C4 polyhaloalkyl, C1-C4 alkoxyl, C1-C4 haloalkoxyl, and C1-C4 polyhaloalkoxyl; and wherein $R^6$ is selected from hydrogen, fluoro, chloro, bromo, iodo, cyano, C1-C4 alkyl, C1-C4 haloalkyl, C1-C4 polyhaloalkyl, C1-C4 alkoxyl, C1-C4 haloalkoxyl, and C1-C4 polyhaloalkoxyl, provided that if Ar is unsubstituted thiopheneyl, then $R^1$ is not isopropyl, or a pharmaceutically acceptable salt, hydrate, solvate, or polymorph thereof, as well as tautomers, geometrical isomers, and optically active forms thereof.

In a further embodiment, the invention relates to compounds of Formula (I), wherein $R^4$ is hydrogen.

The labels α and β are included as aids to help identify and distinguish the particular carbon atom positions for further discussion. The choice of these labels is merely arbitrary and is not intended to be a limitation.

In a further embodiment, the invention relates to compounds of Formula (I), having a structure represented by a formula (II):

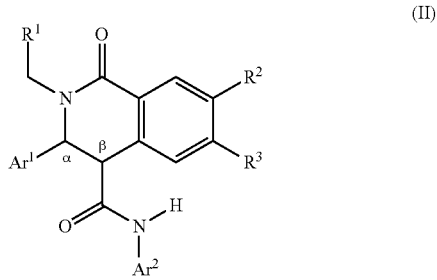

wherein $Ar^1$ is monocyclic heteroaryl selected from 2-thiopheneyl, 3-thiopheneyl, 5-cyano-2-thiopheneyl, 2-furanyl, 3-furanyl, imidazolyl, 4-isoxazolyl, 4-pyrazolyl, N-methyl-4-pyrazolyl, 5-thiazolyl, 5-isothiazolyl, 4-isothiazolyl, 2-pyridinyl, 3-pyridinyl, 4-pyridinyl, 5-pyrimidinyl, and 4-pyridazinyl; wherein $R^1$ is selected from hydrogen, methyl, ethyl, n-propyl, i-propyl, cyclopropyl, n-butyl, i-butyl, s-butyl, t-butyl, and cyclobutyl and, valence permitting, is substituted with 0-3 groups selected from fluoro, chloro, bromo, iodo, cyano, methoxyl, and ethoxyl; wherein R2 and R3 are independently selected from hydrogen, C1-C4 alkyl, C1-C4 alkoxyl, cyano, fluoro, chloro, bromo, and iodo; wherein ring substituents at the carbon atoms denoted with labels α and β have a trans configuration; wherein $Ar^2$ has a structure represented by a formula:

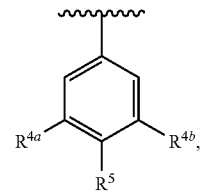

wherein $R^{4a}$ and $R^{4b}$ are independently selected from hydrogen, fluoro, chloro, bromo, iodo, cyano, C1-C4 alkyl, C1-C4 haloalkyl, C1-C4 polyhaloalkyl, C1-C4 alkoxyl, C1-C4 haloalkoxyl, and C1-C4 polyhaloalkoxyl; and wherein $R^5$ is selected from hydrogen, fluoro, chloro, bromo, iodo, cyano, C1-C4 alkyl, C1-C4 haloalkyl, C1-C4 polyhaloalkyl, C1-C4 alkoxyl, C1-C4 haloalkoxyl, and C1-C4 polyhaloalkoxyl, provided that if Ar¹ is unsubstituted thiopheneyl, then R¹ is not isopropyl, as well as tautomers, geometrical isomers, optically active forms thereof.

In a further aspect, the compound has a structure represented by a formula selected from:

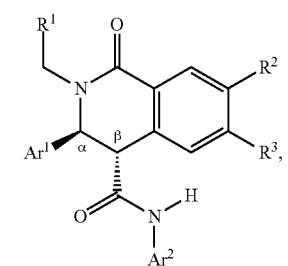
(IIa)

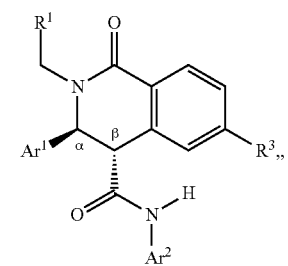
(IIb)

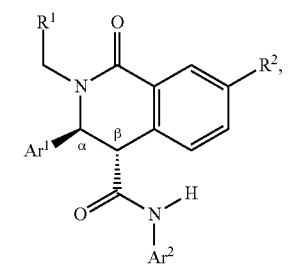
(IIc)

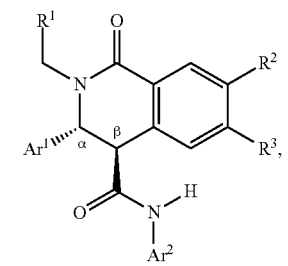
(IId)

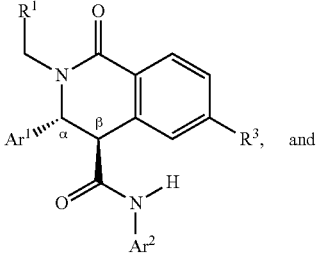
(IIe) and

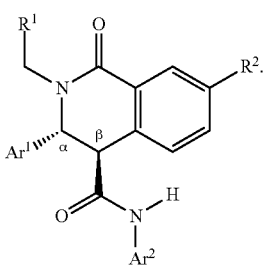
(IIf)

In a further aspect, the compound has a structure represented by a formula selected from:

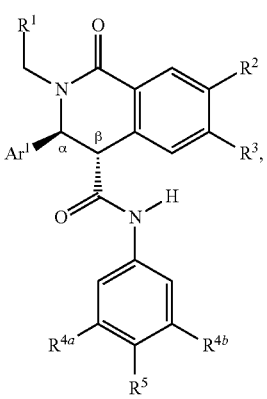
(IIg)

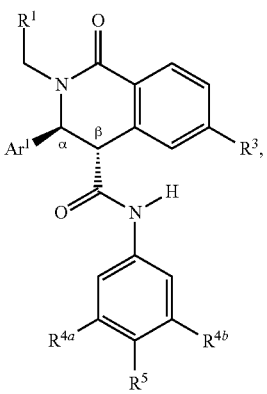
(IIh)

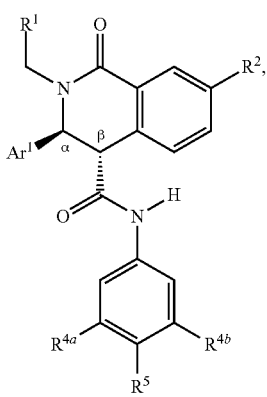
(IIi)

-continued

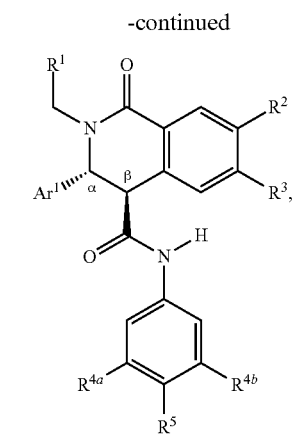

(IIj)

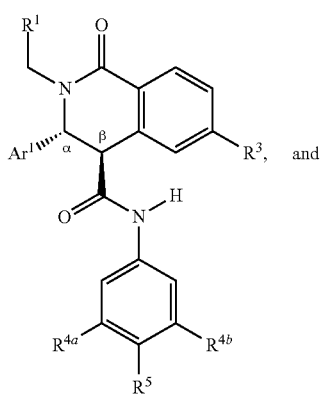

(IIk)

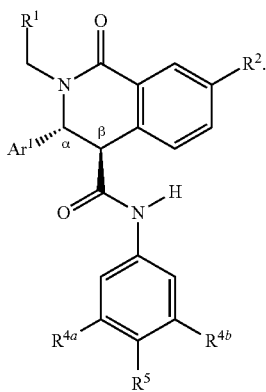

(III)

In a further embodiment, the invention relates to compounds of Formula (I) wherein Ar is selected from 3-pyridinyl, 4-(1-methylpyrazolyl) and 4-pyrazolyl; $R^1$ is selected from $CF_3$ and $(CH_3)_2CH$; $R^2$ and $R^3$ are independently selected from H, $OCH_3$ and F; and $R^{5a}$, $R^{5b}$ and $R^6$ are independently selected from H, CN, F, Cl and $OCF_3$.

In a further aspect, compounds of the invention are dextrorotatory (d) and have a (+)-sign of optical rotation.

In one aspect, the compound exhibits activity against one or more eukaryotic protists of the genus Plasmodium.

1. Structure

The disclosed compounds can have substituents as described herein.

a. Ar or $Ar^1$ Groups

In one aspect, Ar or $Ar^1$ are selected from monocyclic heteroaryl selected from 2-thiopheneyl, 3-thiopheneyl, 5-cyano-2-thiopheneyl, 2-furanyl, 3-furanyl, imidazolyl, 4-isoxazolyl, 4-pyrazolyl, N-methyl-4-pyrazolyl, 5-thiazolyl, 5-isothiazolyl, 4-isothiazolyl, 2-pyridinyl, 3-pyridinyl, 4-pyridinyl, 5-pyrimidinyl, and 4-pyridazinyl. In a further aspect, Ar or $Ar^1$ are selected from monocyclic heteroaryl selected from 2-furanyl, 3-furanyl, imidazolyl, 4-isoxazolyl, 4-pyrazolyl, N-methyl-4-pyrazolyl, 5-thiazolyl, 5-isothiazolyl, 4-isothiazolyl, 2-pyridinyl, 3-pyridinyl, 4-pyridinyl, 5-pyrimidinyl, and 4-pyridazinyl. In a further aspect, $Ar^1$ is not unsubstituted thiopheneyl. In a further aspect, $Ar^1$ is selected from 5-cyano-2-thiopheneyl, 3-pyridinyl, 4-isoxazolyl, N-methyl-4-pyrazolyl, 4-pyrazolyl, 4-isothiazolyl, 5-thiazolyl, 5-pyrimidinyl, and 4-pyridazinyl. In a further aspect, $Ar^1$ has a structure selected from:

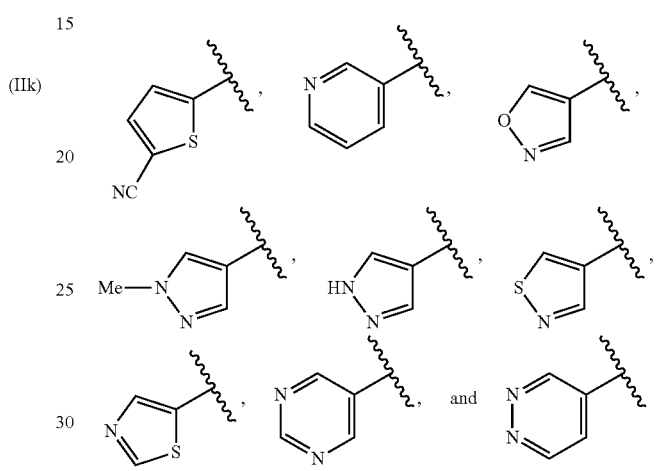

In a further aspect, Ar or Ar1 are selected from 3-pyridinyl, 4-(1-methylpyrazolyl) and 4-pyrazolyl.

b. $R^1$ Groups

In one aspect, $R^1$ is selected from hydrogen, methyl, ethyl, n-propyl, i-propyl, cyclopropyl, n-butyl, i-butyl, s-butyl, t-butyl, and cyclobutyl and, valence permitting, is substituted with 0-3 groups (e.g., 0-1, 0-2, 0-3, 1-2, 1-3, or 2-3 groups) selected from fluoro, chloro, bromo, iodo, cyano, methoxyl, and ethoxyl. In a further aspect, $R^1$ is not isopropyl. In another further aspect, $R^1$ is selected from methyl, n-propyl, i-propyl, and cyclopropyl. In a further aspect, $R^1$ is selected from methyl, n-propyl, i-propyl, and cyclopropyl, optionally substituted with 0-3 groups selected from fluoro and methoxyl. In a further aspect, $R^1$ is substituted with 0-3 groups selected from fluoro and methoxyl. In a further aspect, $R^1$ is selected from isopropyl, trifluoromethyl, cyclopropyl, and methoxymethyl. In a further aspect, $R^1$ is isopropyl or trifluoromethyl. In a further aspect, $R^1$ has a structure selected from:

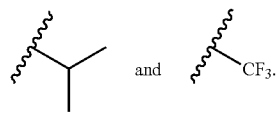

In another further aspect, $R^1$ is selected from $CF_3$, propyl, isopropyl and cyclopropyl, in particular from $CF_3$ and $(CH_3)_2CH$.

c. $R^2$ Groups

In one aspect, $R^2$ is selected from hydrogen, C1-C4 alkyl, C1-C4 alkoxyl, cyano, fluoro, chloro, bromo, and iodo. In a further embodiment, $R^2$ is selected from hydrogen, C1-C4 alkyl, cyano, fluoro, chloro, bromo, and iodo.

In a further aspect, $R^2$ is hydrogen. In a further aspect, $R^2$ is selected from C1-C4 alkyl, cyano, fluoro, chloro, bromo, and iodo. In a further aspect, $R^2$ is selected from hydrogen and fluoro.

In a further embodiment, $R^2$ is selected from H, $OCH_3$ and F.

d. $R^3$ Groups

In one aspect, $R^3$ is selected from hydrogen, C1-C4 alkyl, C1-C4 alkoxyl, cyano, fluoro, chloro, bromo, and iodo. In a further embodiment, $R^3$ is selected from hydrogen, C1-C4 alkyl, cyano, fluoro, chloro, bromo, and iodo. In a further aspect, $R^3$ is hydrogen. In a further aspect, $R^3$ is selected from C1-C4 alkyl, cyano, fluoro, chloro, bromo, and iodo. In a further aspect, $R^3$ is selected from hydrogen, chloro, and fluoro. In a further embodiment, $R^3$ is selected from H, $OCH_3$ and F. In a further embodiment, $R^2$ is H and $R^3$ is selected from H and F. In a further embodiment, $R^2$ is selected from F or $OCH_3$ and $R^3$ is selected from H and fluoro. In a further aspect, $R^2$ and $R^3$ are both hydrogen. In another further aspect, $R^2$ and $R^3$ are both fluoro.

e. $Ar^2$ Groups

In one aspect, $Ar^2$ has a structure represented by a formula:

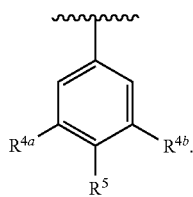

In a further aspect, $Ar^2$ is selected from 3-(trifluoromethoxy)phenyl, 3-(trifluoromethyl)phenyl, 3-chloro-5-cyanophenyl, 3-cyano-4-fluorophenyl, 3-cyano-5-fluorophenyl, 3-fluoro-5-(trifluoromethoxy)phenyl, 3-fluoro-5-(trifluoromethyl)phenyl, 4-fluoro-3-(trifluoromethoxy)phenyl, and 4-fluoro-3-(trifluoromethyl)phenyl. In a further aspect, $Ar^2$ has a structure selected from:

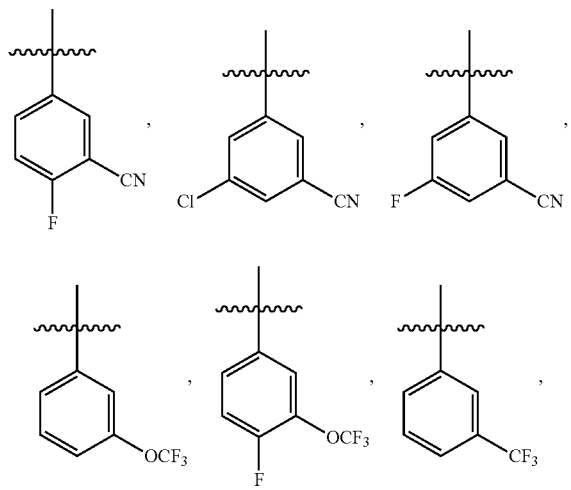

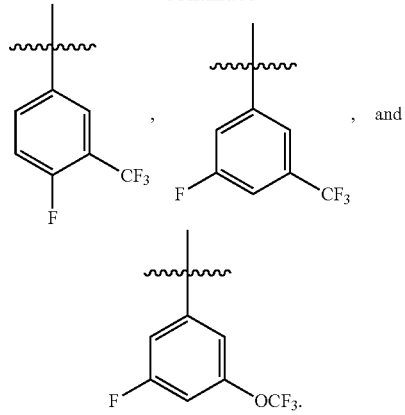

f. $R^4/R^{5a,b}$ Groups

In one aspect, each of $R^{4a}$ and $R^{4b}$, $R^{5a}$ and $R^{5b}$ is independently selected from hydrogen, fluoro, chloro, bromo, iodo, cyano, C1-C4 alkyl, C1-C4 haloalkyl, C1-C4 polyhaloalkyl, C1-C4 alkoxyl, C1-C4 haloalkoxyl, and C1-C4 polyhaloalkoxyl. In a further aspect, $R^{4a}/R^{5a}$ is hydrogen. In a further aspect, $R^{4a}/R^{5a}$ is selected from fluoro, chloro, bromo, iodo, cyano, C1-C4 alkyl, C1-C4 haloalkyl, C1-C4 polyhaloalkyl, C1-C4 alkoxyl, C1-C4 haloalkoxyl, and C1-C4 polyhaloalkoxyl. In a further aspect, $R^{4a}/R^{5a}$ is selected from hydrogen, fluoro, and chloro. In a further aspect, $R^{4b}/R^{5b}$ is hydrogen. In a further aspect, $R^{4b}/R^{5b}$ is selected from fluoro, chloro, bromo, iodo, cyano, C1-C4 alkyl, C1-C4 haloalkyl, C1-C4 polyhaloalkyl, C1-C4 alkoxyl, C1-C4 haloalkoxyl, and C1-C4 polyhaloalkoxyl. In a further aspect, $R^{4b}/R^{5b}$ is selected from cyano, trifluoromethyl, and trifluoromethoxyl.

In a further embodiment, $R^{4a}$ and $R^{4b}$, $R^{5a}$ and $R^{5b}$ are independently selected from H, CN, F, Cl and $OCF_3$. In a further embodiment, $R^{4a}$ and $R^{5a}$ are H and $R^{4b}$ and $R^{5b}$ are selected from cyano and $OCF_3$. In a further embodiment, $R^{4a}$ and $R^{5a}$ are selected from CN, F, Cl and $OCF_3$ and $R^{4b}$ and $R^{5b}$ are selected from H, cyano, and $OCF_3$.

g. $R^5/R^6$ Groups

In one aspect, $R^5/R^6$ is selected from hydrogen, fluoro, chloro, bromo, iodo, cyano, C1-C4 alkyl, C1-C4 haloalkyl, C1-C4 polyhaloalkyl, C1-C4 alkoxyl, C1-C4 haloalkoxyl, and C1-C4 polyhaloalkoxyl. In a further aspect, $R^5$ is hydrogen. In a further aspect, $R^5/R^6$ is selected from fluoro, chloro, bromo, iodo, cyano, C1-C4 alkyl, C1-C4 haloalkyl, C1-C4 polyhaloalkyl, C1-C4 alkoxyl, C1-C4 haloalkoxyl, and C1-C4 polyhaloalkoxyl. In a further aspect, $R^5$ is selected from hydrogen and fluoro. In a further embodiment, $R^5/R^6$ are selected from H, CN, F, Cl and $OCF_3$.

In a further aspect, $R^{4a}$, $R^{4b}$, and $R^5$ ($R^{5a}$, $R^{5b}$, and $R^6$) are not simultaneously hydrogen. In a further aspect, $R^{4a}/R^{5a}$ is selected from hydrogen, fluoro, and chloro; wherein $R^{4b}/R^{5b}$ is selected from cyano, trifluoromethyl, and trifluoromethoxyl; and wherein $R^5/R^6$ is selected from hydrogen and fluoro.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

2. Example Compounds

In one aspect, a compound can be present as one or more of the compounds shown in Table I, or a subgroup thereof:

TABLE I

TABLE I-continued
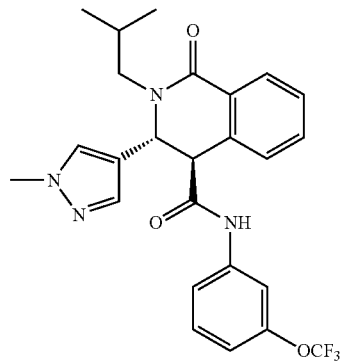 [SMILES: CC(C)CN1C(=O)c2ccccc2[C@@H](C(=O)Nc2cccc(OC(F)(F)F)c2)[C@@H]1c1cnn(C)c1]
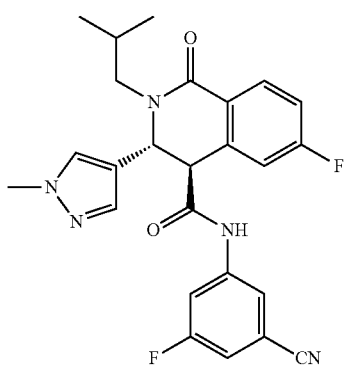 [SMILES: CC(C)CN1C(=O)c2ccc(F)cc2[C@@H](C(=O)Nc2cc(F)cc(C#N)c2)[C@@H]1c1cnn(C)c1]
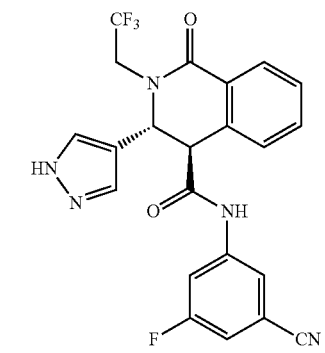 [SMILES: N#Cc1cc(F)cc(NC(=O)[C@@H]2c3ccccc3C(=O)N(CC(F)(F)F)[C@H]2c2cn[nH]c2)c1]
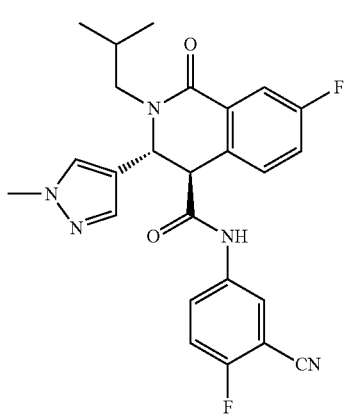 [SMILES: CC(C)CN1C(=O)c2cc(F)ccc2[C@@H](C(=O)Nc2ccc(F)c(C#N)c2)[C@@H]1c1cnn(C)c1]
TABLE I-continued
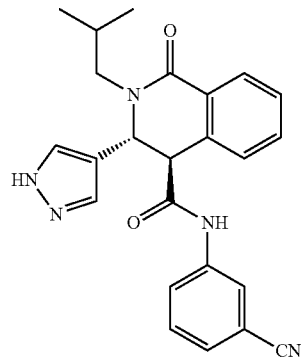 [SMILES: CC(C)CN1C(=O)c2ccccc2[C@@H](C(=O)Nc2cccc(C#N)c2)[C@@H]1c1cn[nH]c1]
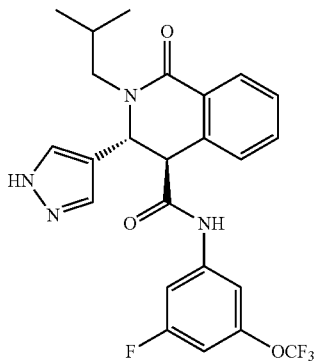 [SMILES: CC(C)CN1C(=O)c2ccccc2[C@@H](C(=O)Nc2cc(F)cc(OC(F)(F)F)c2)[C@@H]1c1cn[nH]c1]
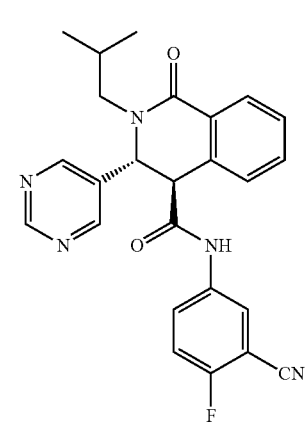 [SMILES: CC(C)CN1C(=O)c2ccccc2[C@@H](C(=O)Nc2ccc(F)c(C#N)c2)[C@@H]1c1cncnc1]
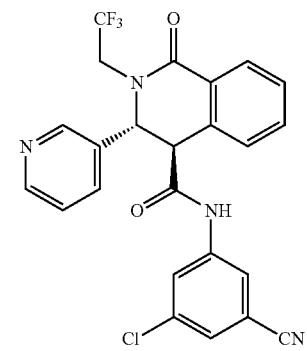 [SMILES: N#Cc1cc(Cl)cc(NC(=O)[C@@H]2c3ccccc3C(=O)N(CC(F)(F)F)[C@H]2c2cccnc2)c1]

TABLE I-continued
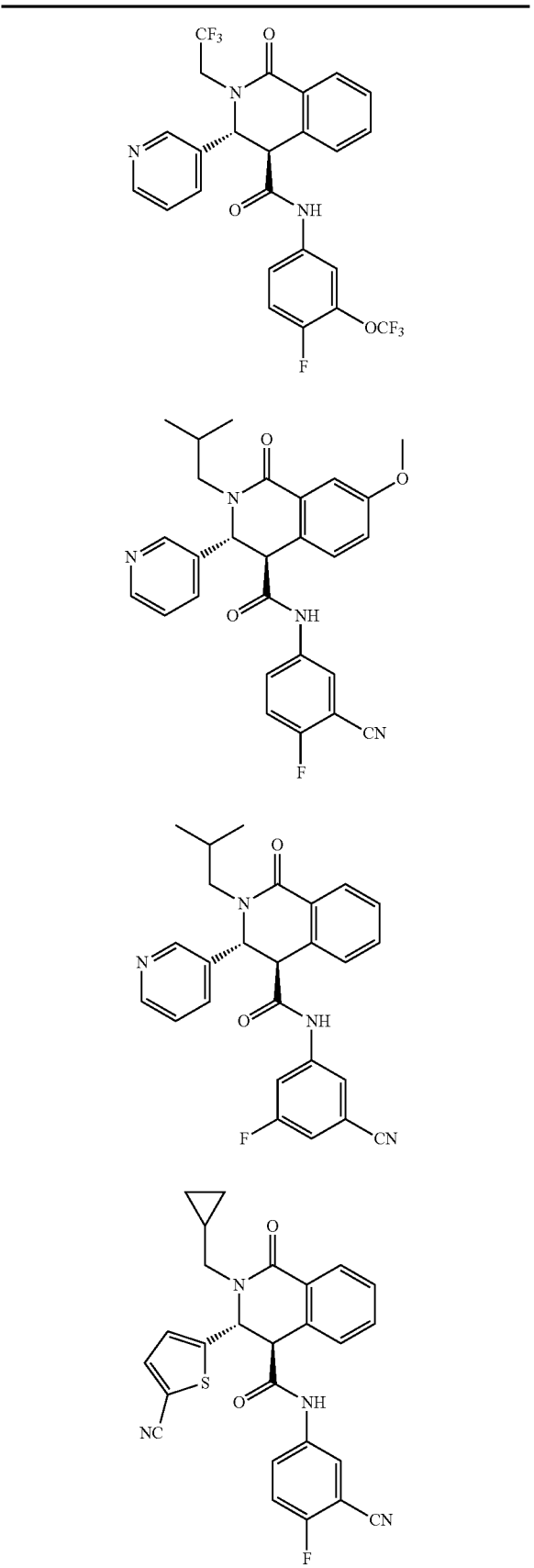
TABLE I-continued
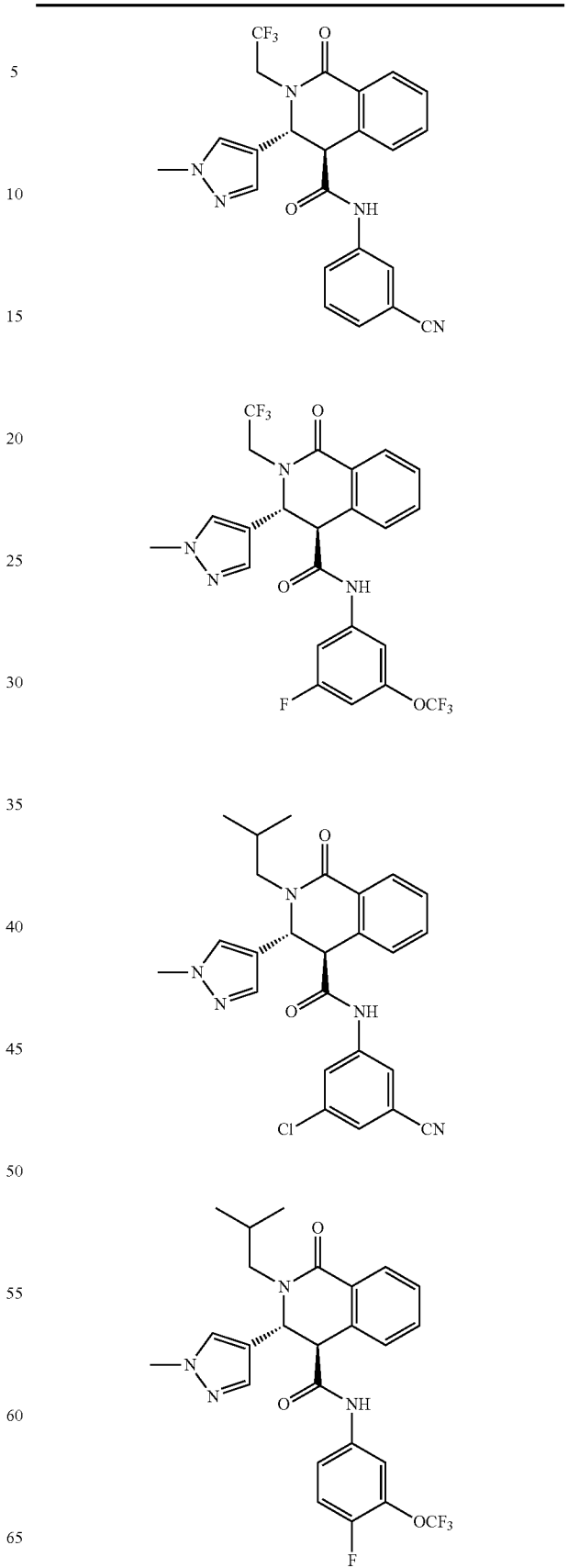

TABLE I-continued
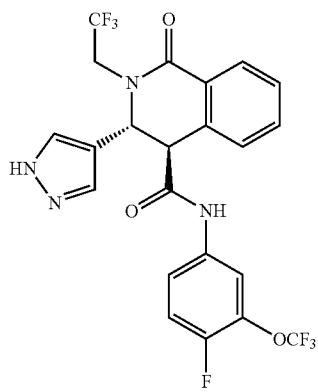 [SMILES: O=C(Nc1ccc(F)c(OC(F)(F)F)c1)[C@@H]1c2ccccc2C(=O)N(CC(F)(F)F)[C@H]1c1cn[nH]c1]
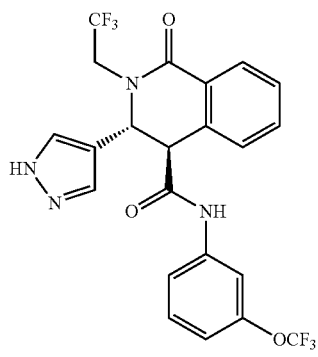 [SMILES: O=C(Nc1cccc(OC(F)(F)F)c1)[C@@H]1c2ccccc2C(=O)N(CC(F)(F)F)[C@H]1c1cn[nH]c1]
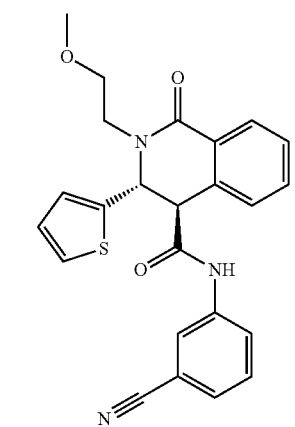 [SMILES: COCCN1C(=O)c2ccccc2[C@@H](C(=O)Nc2cccc(C#N)c2)[C@@H]1c1cccs1]
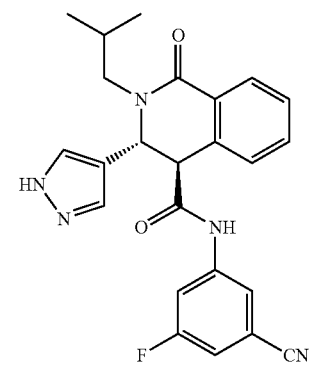 [SMILES: CC(C)CN1C(=O)c2ccccc2[C@@H](C(=O)Nc2cc(F)cc(C#N)c2)[C@@H]1c1cn[nH]c1]
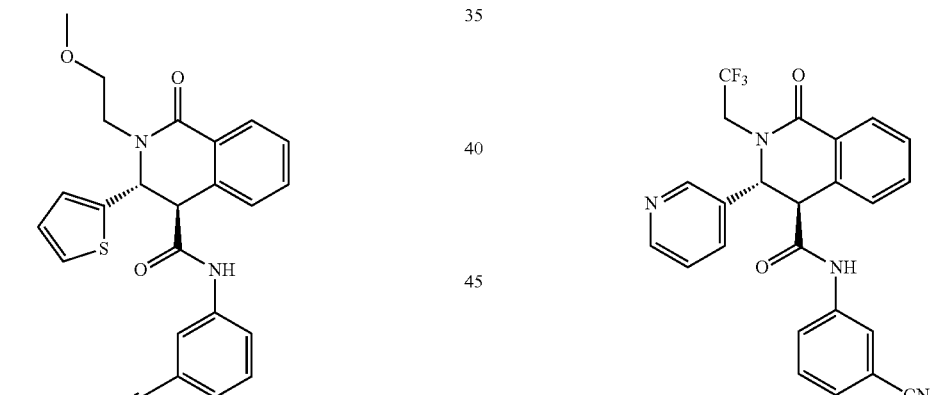

TABLE I-continued
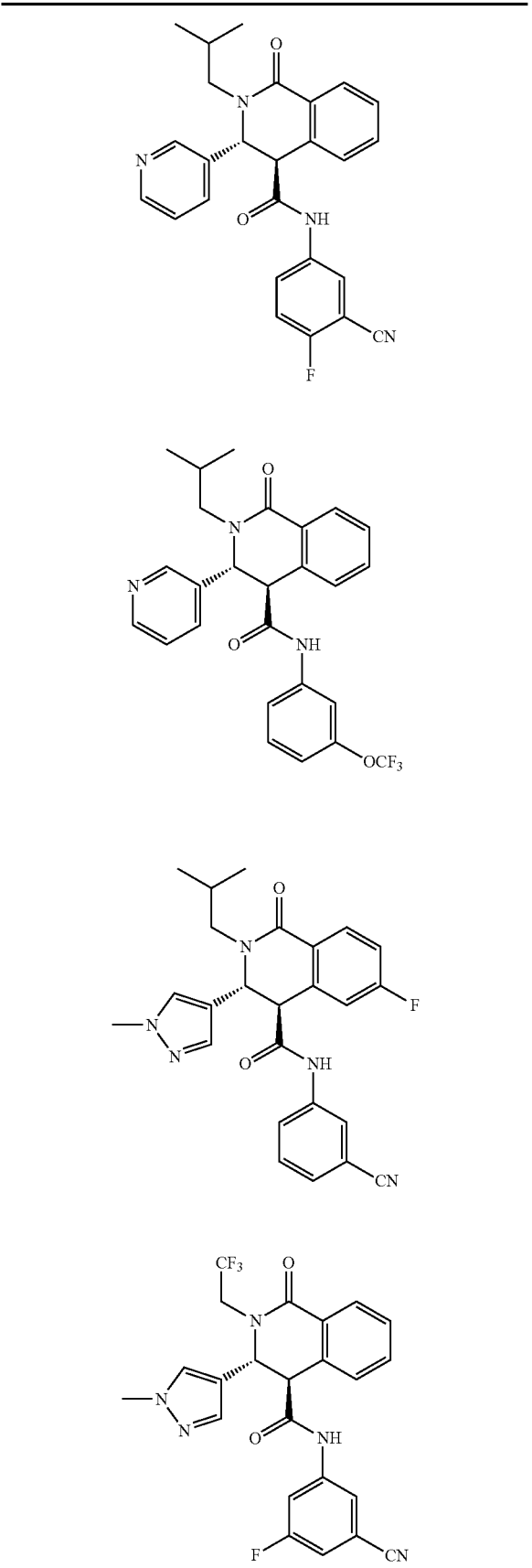
TABLE I-continued
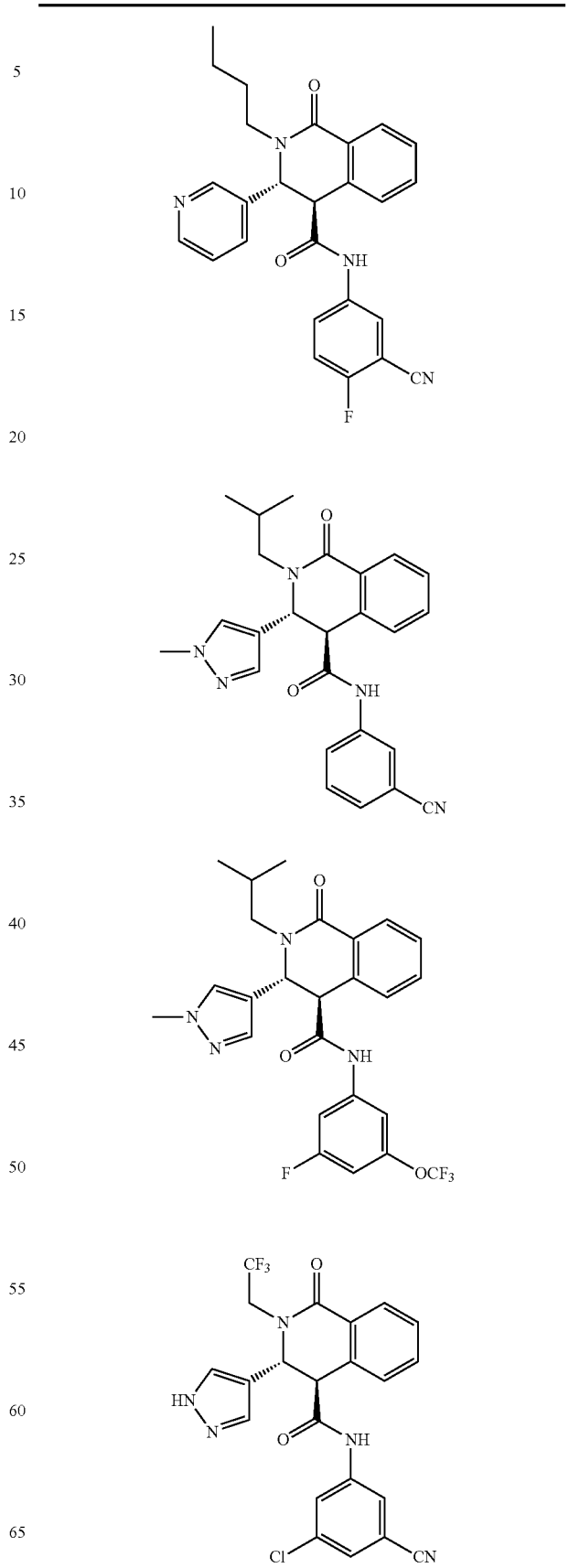

TABLE I-continued
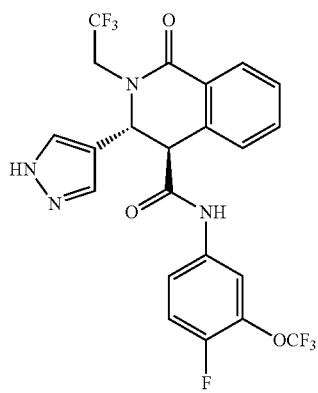 [SMILES: O=C(Nc1ccc(F)c(OC(F)(F)F)c1)[C@@H]1c2ccccc2C(=O)N(CC(F)(F)F)[C@H]1c1cn[nH]c1]
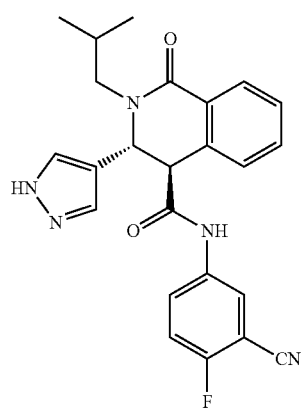 [SMILES: CC(C)CN1C(=O)c2ccccc2[C@@H](C(=O)Nc2ccc(F)c(C#N)c2)[C@@H]1c1cn[nH]c1]
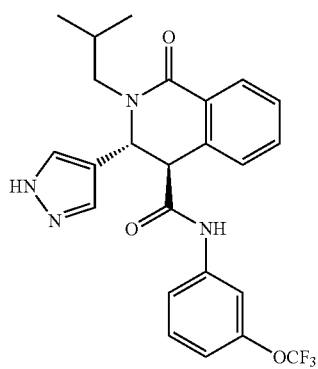 [SMILES: CC(C)CN1C(=O)c2ccccc2[C@@H](C(=O)Nc2cccc(OC(F)(F)F)c2)[C@@H]1c1cn[nH]c1]
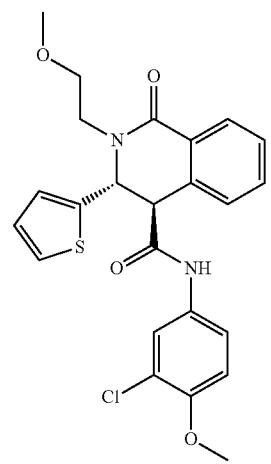 [SMILES: COCCN1C(=O)c2ccccc2[C@@H](C(=O)Nc2ccc(OC)c(Cl)c2)[C@@H]1c1cccs1]
TABLE I-continued
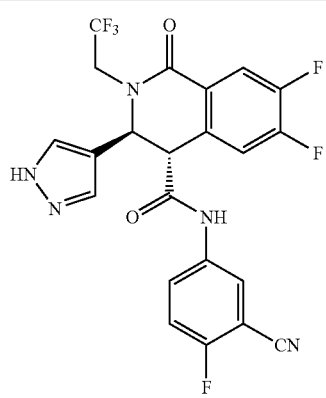 [SMILES: N#Cc1cc(NC(=O)[C@H]2c3cc(F)c(F)cc3C(=O)N(CC(F)(F)F)[C@@H]2c2cn[nH]c2)ccc1F]
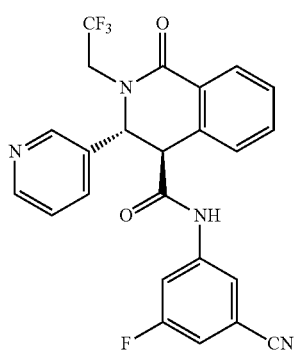 [SMILES: N#Cc1cc(F)cc(NC(=O)[C@@H]2c3ccccc3C(=O)N(CC(F)(F)F)[C@H]2c2cccnc2)c1]
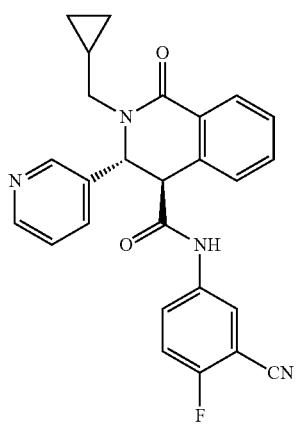 [SMILES: N#Cc1cc(NC(=O)[C@@H]2c3ccccc3C(=O)N(CC3CC3)[C@H]2c2cccnc2)ccc1F]
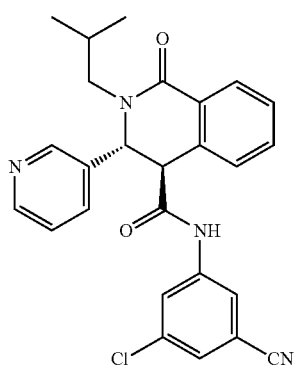 [SMILES: CC(C)CN1C(=O)c2ccccc2[C@@H](C(=O)Nc2cc(Cl)cc(C#N)c2)[C@@H]1c1cccnc1]

TABLE I-continued
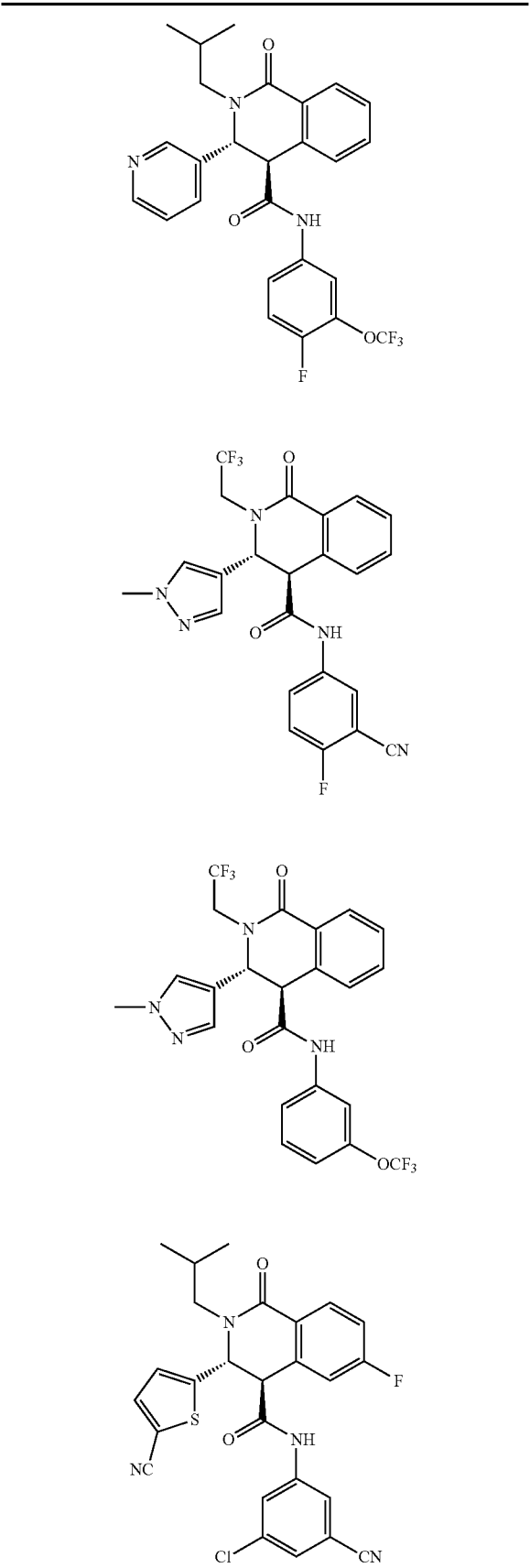
TABLE I-continued
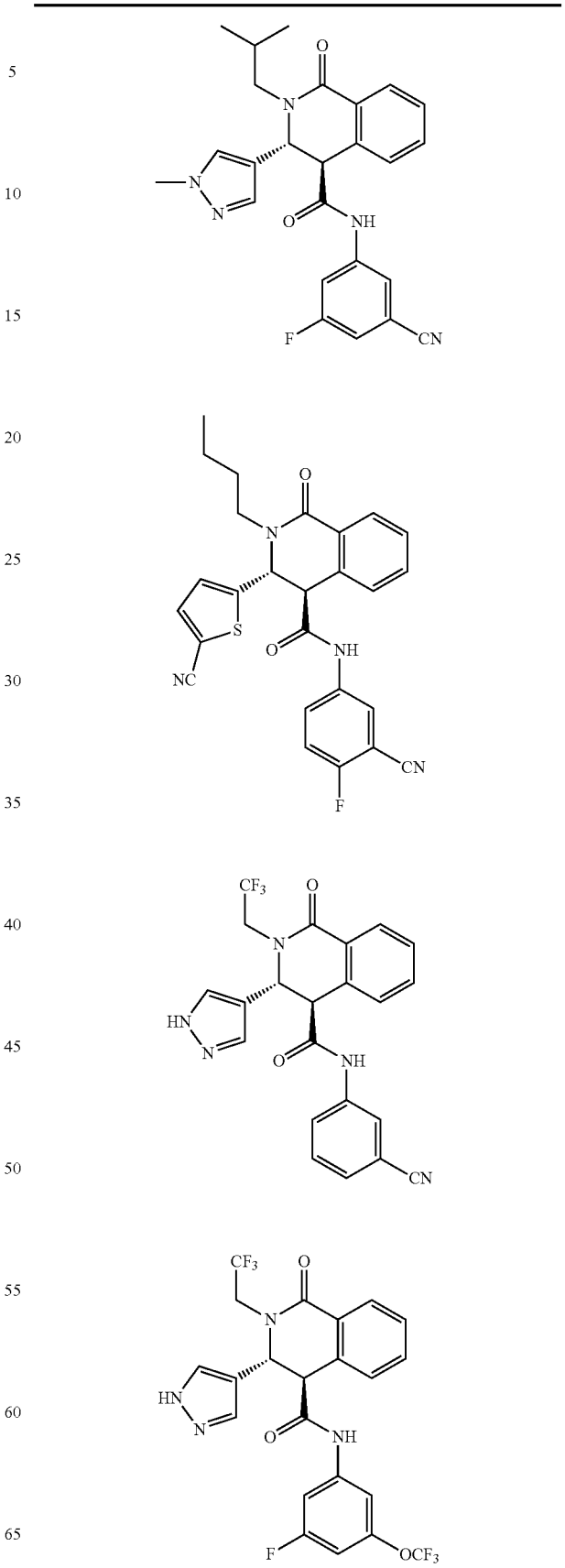

TABLE I-continued

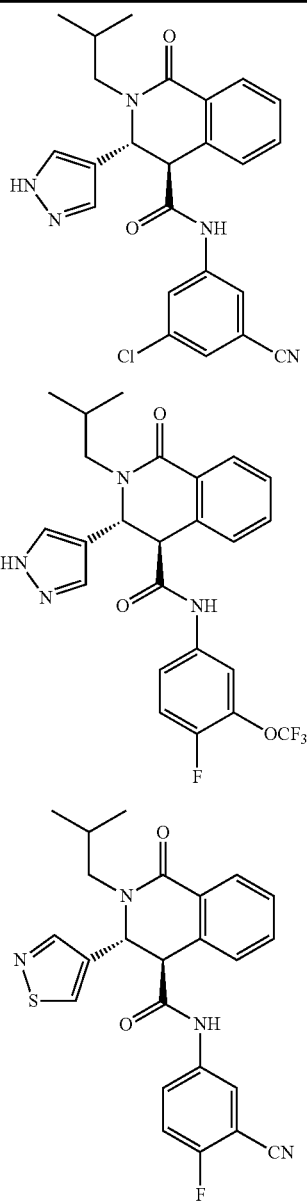

According to one aspect of the invention, the compounds are selected from the following group:

N-(3-cyano-4-fluorophenyl)-1-oxo-3-(pyridin-3-yl)-2-(2,2,2-trifluoroethyl)-1,2,3,4-tetrahydroisoquinoline-4-carboxamide;

N-(3-chloro-5-cyanophenyl)-1-oxo-3-(pyridin-3-yl)-2-(2,2,2-trifluoroethyl)-1,2,3,4-tetrahydroisoquinoline-4-carboxamide;

N-(3-cyanophenyl)-1-oxo-3-(pyridin-3-yl)-2-(2,2,2-trifluoroethyl)-1,2,3,4-tetrahydroisoquinoline-4-carboxamide;

N-(3-cyano-5-fluorophenyl)-1-oxo-3-(pyridin-3-yl)-2-(2,2,2-trifluoroethyl)-1,2,3,4-tetrahydroisoquinoline-4-carboxamide;

1-oxo-3-(pyridin-3-yl)-2-(2,2,2-trifluoroethyl)-N-(3-(trifluoromethoxy)phenyl)-1,2,3,4-tetrahydroisoquinoline-4-carboxamide;

N-(4-fluoro-3-(trifluoromethoxy)phenyl)-1-oxo-3-(pyridin-3-yl)-2-(2,2,2-trifluoroethyl)-1,2,3,4-tetrahydroisoquinoline-4-carboxamide;

N-(3-fluoro-5-(trifluoromethoxy)phenyl)-1-oxo-3-(pyridin-3-yl)-2-(2,2,2-trifluoroethyl)-1,2,3,4-tetrahydroisoquinoline-4-carboxamide;

N-(3-cyano-4-fluorophenyl)-2-(cyclopropylmethyl)-1-oxo-3-(pyridin-3-yl)-1,2,3,4

N-(3-cyano-5-fluorophenyl)-7-fluoro-3-(1-methyl-1H-pyrazol-4-yl)-1-oxo-2-(2,2,2-tetrahydroisoquinoline-4-carboxamide;

N-(3-cyano-4-fluorophenyl)-2-isobutyl-7-methoxy-1-oxo-3-(pyridin-3-yl)-1,2,3,4-trifluoroethyl)-1,2,3,4-tetrahydroisoquinoline-4-carboxamide; tetrahydroisoquinoline-4-carboxamide;N-(3-cyano-4-fluorophenyl)-2-isobutyl-1-oxo-3-(pyridin-3-yl)-1,2,3,4-tetrahydroisoquinoline-4-carboxamide;

N-(3-chloro-5-cyanophenyl)-2-isobutyl-1-oxo-3-(pyridin-3-yl)-1,2,3,4-tetrahydroisoquinoline-4-carboxamide;

N-(3-cyanophenyl)-2-isobutyl-1-oxo-3-(pyridin-3-yl)-1,2,3,4-tetrahydroisoquinoline-4-carboxamide;

N-(3-cyano-5-fluorophenyl)-2-isobutyl-1-oxo-3-(pyridin-3-yl)-1,2,3,4-tetrahydroisoquinoline-4-carboxamide;

2-isobutyl-1-oxo-3-(pyridin-3-yl)-N-(3-(trifluoromethoxy)phenyl)-1,2,3,4-tetrahydroisoquinoline-4-carboxamide;

N-(4-fluoro-3-(trifluoromethoxy)phenyl)-2-isobutyl-1-oxo-3-(pyridin-3-yl)-1,2,3,4-tetrahydroisoquinoline-4-carboxamide;

N-(3-fluoro-5-(trifluoromethoxy)phenyl)-2-isobutyl-1-oxo-3-(pyridin-3-yl)-1,2,3,4-tetrahydroisoquinoline-4-carboxamide;

N-(3-cyano-4-fluorophenyl)-3-(5-cyanothiophen-2-yl)-2-(cyclopropylmethyl)-1-oxo-1,2,3,4-tetrahydroisoquinoline-4-carboxamide;

N-(3-cyanophenyl)-6-fluoro-2-isobutyl-3-(1-methyl-1H-pyrazol-4-yl)-1-oxo-1,2,3,4-tetrahydroisoquinoline-4-carboxamide;

N-(3-cyano-4-fluorophenyl)-3-(1-methyl-1H-pyrazol-4-yl)-1-oxo-2-(2,2,2-trifluoroethyl)-1,2,3,4-tetrahydroisoquinoline-4-carboxamide;

N-(3-chloro-5-cyanophenyl)-3-(1-methyl-1H-pyrazol-4-yl)-1-oxo-2-(2,2,2-trifluoroethyl)-1,2,3,4-tetrahydroisoquinoline-4-carboxamide;

N-(3-cyanophenyl)-3-(1-methyl-1H-pyrazol-4-yl)-1-oxo-2-(2,2,2-trifluoroethyl)-1,2,3,4-tetrahydroisoquinoline-4-carboxamide;

N-(3-cyano-5-fluorophenyl)-3-(1-methyl-1H-pyrazol-4-yl)-1-oxo-2-(2,2,2-trifluoroethyl)-1,2,3,4-tetrahydroisoquinoline-4-carboxamide;

3-(1-methyl-1H-pyrazol-4-yl)-1-oxo-2-(2,2,2-trifluoroethyl)-N-(3-(trifluoromethoxy)phenyl)-1,2,3,4-tetrahydroisoquinoline-4-carboxamide;

N-(4-fluoro-3-(trifluoromethoxy)phenyl)-3-(1-methyl-1H-pyrazol-4-yl)-1-oxo-2-(2,2,2-trifluoroethyl)-1,2,3,4-tetrahydroisoquinoline-4-carboxamide;

N-(3-fluoro-5-(trifluoromethoxy)phenyl)-3-(1-methyl-1H-pyrazol-4-yl)-1-oxo-2-(2,2,2-trifluoroethyl)-1,2,3,4-tetrahydroisoquinoline-4-carboxamide;

2-butyl-N-(3-cyano-4-fluorophenyl)-1-oxo-3-(pyridin-3-yl)-1,2,3,4-tetrahydroisoquinoline-4-carboxamide;

N-(3-chloro-5-cyanophenyl)-3-(5-cyanothiophen-2-yl)-6-fluoro-2-isobutyl-1-oxo-1,2,3,4-tetrahydroisoquinoline-4-carboxamide;

N-(3-cyano-4-fluorophenyl)-2-isobutyl-3-(1-methyl-1H-pyrazol-4-yl)-1-oxo-1,2,3,4-tetrahydroisoquinoline-4-carboxamide;

N-(3-chloro-5-cyanophenyl)-2-isobutyl-3-(1-methyl-1H-pyrazol-4-yl)-1-oxo-1,2,3,4-tetrahydroisoquinoline-4-carboxamide;

N-(3-cyanophenyl)-2-isobutyl-3-(1-methyl-1H-pyrazol-4-yl)-1-oxo-1,2,3,4-tetrahydroisoquinoline-4-carboxamide;
N-(3-cyano-5-fluorophenyl)-2-isobutyl-3-(1-methyl-1H-pyrazol-4-yl)-1-oxo-1,2,3,4-tetrahydroisoquinoline-4-carboxamide;
2-isobutyl-3-(1-methyl-1H-pyrazol-4-yl)-1-oxo-N-(3-(trifluoromethoxy)phenyl)-1,2,3,4-tetrahydroisoquinoline-4-carboxamide;
N-(4-fluoro-3-(trifluoromethoxy)phenyl)-2-isobutyl-3-(1-methyl-1H-pyrazol-4-yl)-1-oxo-1,2,3,4-tetrahydroisoquinoline-4-carboxamide;
N-(3-fluoro-5-(trifluoromethoxy)phenyl)-2-isobutyl-3-(1-methyl-1H-pyrazol-4-yl)-1-oxo-1,2,3,4-tetrahydroisoquinoline-4-carboxamide;
2-butyl-N-(3-cyano-4-fluorophenyl)-3-(5-cyanothiophen-2-yl)-1-oxo-1,2,3,4-tetrahydroisoquinoline-4-carboxamide;
N-(3-cyano-5-fluorophenyl)-6-fluoro-2-isobutyl-3-(1-methyl-1H-pyrazol-4-yl)-1-oxo-1,2,3,4-tetrahydroisoquinoline-4-carboxamide;
N-(3-cyano-4-fluorophenyl)-1-oxo-3-(1H-pyrazol-4-yl)-2-(2,2,2-trifluoroethyl)-1,2,3,4-tetrahydroisoquinoline-4-carboxamide;
N-(3-chloro-5-cyanophenyl)-1-oxo-3-(1H-pyrazol-4-yl)-2-(2,2,2-trifluoroethyl)-1,2,3,4-tetrahydroisoquinoline-4-carboxamide;
N-(3-cyanophenyl)-1-oxo-3-(1H-pyrazol-4-yl)-2-(2,2,2-trifluoroethyl)-1,2,3,4-tetrahydroisoquinoline-4-carboxamide;
N-(3-cyano-5-fluorophenyl)-1-oxo-3-(1H-pyrazol-4-yl)-2-(2,2,2-trifluoroethyl)-1,2,3,4-tetrahydroisoquinoline-4-carboxamide;
1-oxo-3-(1H-pyrazol-4-yl)-2-(2,2,2-trifluoroethyl)-N-(3-(trifluoromethoxy)phenyl)-1,2,3,4-tetrahydroisoquinoline-4-carboxamide;
N-(4-fluoro-3-(trifluoromethoxy)phenyl)-1-oxo-3-(1H-pyrazol-4-yl)-2-(2,2,2-trifluoroethyl)-1,2,3,4-tetrahydroisoquinoline-4-carboxamide;
N-(3-fluoro-5-(trifluoromethoxy)phenyl)-1-oxo-3-(1H-pyrazol-4-yl)-2-(2,2,2-trifluoroethyl)-1,2,3,4-tetrahydroisoquinoline-4-carboxamide;
N-(3-cyano-4-fluorophenyl)-7-fluoro-2-isobutyl-3-(1-methyl-1H-pyrazol-4-yl)-1-oxo-1,2,3,4-tetrahydroisoquinoline-4-carboxamide;
N-(3-cyanophenyl)-2-(2-methoxyethyl)-1-oxo-3-(thiophen-2-yl)-1,2,3,4-tetrahydroisoquinoline-4-carboxamide;
N-(3-cyano-4-fluorophenyl)-2-isobutyl-1-oxo-3-(1H-pyrazol-4-yl)-1,2,3,4-tetrahydroisoquinoline-4-carboxamide;
N-(3-chloro-5-cyanophenyl)-2-isobutyl-1-oxo-3-(1H-pyrazol-4-yl)-1,2,3,4-tetrahydroisoquinoline-4-carboxamide;
N-(3-cyanophenyl)-2-isobutyl-1-oxo-3-(1H-pyrazol-4-yl)-1,2,3,4-tetrahydroisoquinoline-4-carboxamide;
N-(3-cyano-5-fluorophenyl)-2-isobutyl-1-oxo-3-(1H-pyrazol-4-yl)-1,2,3,4-tetrahydroisoquinoline-4-carboxamide;
2-isobutyl-1-oxo-3-(1H-pyrazol-4-yl)-N-(3-(trifluoromethoxy)phenyl)-1,2,3,4-tetrahydroisoquinoline-4-carboxamide;
N-(4-fluoro-3-(trifluoromethoxy)phenyl)-2-isobutyl-1-oxo-3-(1H-pyrazol-4-yl)-1,2,3,4-tetrahydroisoquinoline-4-carboxamide;
N-(3-fluoro-5-(trifluoromethoxy)phenyl)-2-isobutyl-1-oxo-3-(1H-pyrazol-4-yl)-1,2,3,4-tetrahydroisoquinoline-4-carboxamide;
N-(3-chloro-5-cyanophenyl)-7-fluoro-2-isobutyl-3-(1-methyl-1H-pyrazol-4-yl)-1-oxo-1,2,3,4-tetrahydroisoquinoline-4-carboxamide;
N-(3-chloro-4-methoxyphenyl)-2-(2-methoxyethyl)-1-oxo-3-(thiophen-2-yl)-1,2,3,4-tetrahydroisoquinoline-4-carboxamide;
N-(3-cyano-4-fluorophenyl)-2-isobutyl-3-(isothiazol-4-yl)-1-oxo-1,2,3,4-tetrahydroisoquinoline-4-carboxamide;
N-(3-cyano-4-fluorophenyl)-2-isobutyl-1-oxo-3-(pyrimidin-5-yl)-1,2,3,4-tetrahydroisoquinoline-4-carboxamide;
N-(3-cyano-5-fluorophenyl)-3-(5-cyanothiophen-2-yl)-6-fluoro-2-isobutyl-1-oxo-1,2,3,4-tetrahydroisoquinoline-4-carboxamide; and
N-(3-cyano-4-fluorophenyl)-1-oxo-3-(1H-pyrazol-4-yl-6,7-difluoro-2-(2,2,2-trifluoroethyl)-1,2,3,4-tetrahydroisoquinoline-4-carboxamide.

According to another aspect, the invention relates to compounds of the invention selected from the following group:
N-(3-cyano-4-fluorophenyl)-1-oxo-3-(pyridin-3-yl)-2-(2,2,2-trifluoroethyl)-1,2,3,4-tetrahydroisoquinoline-4-carboxamide;
N-(3-chloro-5-cyanophenyl)-1-oxo-3-(pyridin-3-yl)-2-(2,2,2-trifluoroethyl)-1,2,3,4-tetrahydroisoquinoline-4-carboxamide;
N-(3-cyanophenyl)-1-oxo-3-(pyridin-3-yl)-2-(2,2,2-trifluoroethyl)-1,2,3,4-tetrahydroisoquinoline-4-carboxamide;
N-(3-cyano-5-fluorophenyl)-1-oxo-3-(pyridin-3-yl)-2-(2,2,2-trifluoroethyl)-1,2,3,4-tetrahydroisoquinoline-4-carboxamide;
1-oxo-3-(pyridin-3-yl)-2-(2,2,2-trifluoroethyl)-N-(3-(trifluoromethoxy)phenyl)-1,2,3,4-tetrahydroisoquinoline-4-carboxamide;
N-(4-fluoro-3-(trifluoromethoxy)phenyl)-1-oxo-3-(pyridin-3-yl)-2-(2,2,2-trifluoroethyl)-1,2,3,4-tetrahydroisoquinoline-4-carboxamide;
N-(3-fluoro-5-(trifluoromethoxy)phenyl)-1-oxo-3-(pyridin-3-yl)-2-(2,2,2-trifluoroethyl)-1,2,3,4-tetrahydroisoquinoline-4-carboxamide;
N-(3-cyano-4-fluorophenyl)-2-(cyclopropylmethyl)-1-oxo-3-(pyridin-3-yl)-1,2,3,4-tetrahydroisoquinoline-4-carboxamide;
N-(3-cyano-5-fluorophenyl)-7-fluoro-3-(1-methyl-1H-pyrazol-4-yl)-1-oxo-2-(2,2,2-trifluoroethyl)-1,2,3,4-tetrahydroisoquinoline-4-carboxamide;
N-(3-cyano-4-fluorophenyl)-2-isobutyl-7-methoxy-1-oxo-3-(pyridin-3-yl)-1,2,3,4-tetrahydroisoquinoline-4-carboxamide;N-(3-cyano-4-fluorophenyl)-2-isobutyl-1-oxo-3-(pyridin-3-yl)-1,2,3,4-tetrahydroisoquinoline-4-carboxamide;
N-(3-chloro-5-cyanophenyl)-2-isobutyl-1-oxo-3-(pyridin-3-yl)-1,2,3,4-tetrahydroisoquinoline-4-carboxamide;
N-(3-cyanophenyl)-2-isobutyl-1-oxo-3-(pyridin-3-yl)-1,2,3,4-tetrahydroisoquinoline-4-carboxamide;
N-(3-cyano-5-fluorophenyl)-2-isobutyl-1-oxo-3-(pyridin-3-yl)-1,2,3,4-tetrahydroisoquinoline-4-carboxamide;
2-isobutyl-1-oxo-3-(pyridin-3-yl)-N-(3-(trifluoromethoxy)phenyl)-1,2,3,4-tetrahydroisoquinoline-4-carboxamide;
N-(4-fluoro-3-(trifluoromethoxy)phenyl)-2-isobutyl-1-oxo-3-(pyridin-3-yl)-1,2,3,4-tetrahydroisoquinoline-4-carboxamide;
N-(3-fluoro-5-(trifluoromethoxy)phenyl)-2-isobutyl-1-oxo-3-(pyridin-3-yl)-1,2,3,4-tetrahydroisoquinoline-4-carboxamide;
N-(3-cyanophenyl)-6-fluoro-2-isobutyl-3-(1-methyl-1H-pyrazol-4-yl)-1-oxo-1,2,3,4-tetrahydroisoquinoline-4-carboxamide;
N-(3-cyano-4-fluorophenyl)-3-(1-methyl-1H-pyrazol-4-yl)-1-oxo-2-(2,2,2-trifluoroethyl)-1,2,3,4-tetrahydroisoquinoline-4-carboxamide;
N-(3-chloro-5-cyanophenyl)-3-(1-methyl-1H-pyrazol-4-yl)-1-oxo-2-(2,2,2-trifluoroethyl)-1,2,3,4-tetrahydroisoquinoline-4-carboxamide;

N-(3-cyanophenyl)-3-(1-methyl-1H-pyrazol-4-yl)-1-oxo-2-(2,2,2-trifluoroethyl)-1,2,3,4-tetrahydroisoquinoline-4-carboxamide;
N-(3-cyano-5-fluorophenyl)-3-(1-methyl-1H-pyrazol-4-yl)-1-oxo-2-(2,2,2-trifluoroethyl)-1,2,3,4-tetrahydroisoquinoline-4-carboxamide;
3-(1-methyl-1H-pyrazol-4-yl)-1-oxo-2-(2,2,2-trifluoroethyl)-N-(3-(trifluoromethoxy)phenyl)-1,2,3,4-tetrahydroisoquinoline-4-carboxamide;
N-(4-fluoro-3-(trifluoromethoxy)phenyl)-3-(1-methyl-1H-pyrazol-4-yl)-1-oxo-2-(2,2,2-trifluoroethyl)-1,2,3,4-tetrahydroisoquinoline-4-carboxamide;
N-(3-fluoro-5-(trifluoromethoxy)phenyl)-3-(1-methyl-1H-pyrazol-4-yl)-1-oxo-2-(2,2,2-trifluoroethyl)-1,2,3,4-tetrahydroisoquinoline-4-carboxamide;
2-butyl-N-(3-cyano-4-fluorophenyl)-1-oxo-3-(pyridin-3-yl)-1,2,3,4-tetrahydroisoquinoline-4-carboxamide;
N-(3-cyano-4-fluorophenyl)-2-isobutyl-3-(1-methyl-1H-pyrazol-4-yl)-1-oxo-1,2,3,4-tetrahydroisoquinoline-4-carboxamide;
N-(3-chloro-5-cyanophenyl)-2-isobutyl-3-(1-methyl-1H-pyrazol-4-yl)-1-oxo-1,2,3,4-tetrahydroisoquinoline-4-carboxamide;
N-(3-cyanophenyl)-2-isobutyl-3-(1-methyl-1H-pyrazol-4-yl)-1-oxo-1,2,3,4-tetrahydroisoquinoline-4-carboxamide;
N-(3-cyano-5-fluorophenyl)-2-isobutyl-3-(1-methyl-1H-pyrazol-4-yl)-1-oxo-1,2,3,4-tetrahydroisoquinoline-4-carboxamide;
2-isobutyl-3-(1-methyl-1H-pyrazol-4-yl)-1-oxo-N-(3-(trifluoromethoxy)phenyl)-1,2,3,4-tetrahydroisoquinoline-4-carboxamide;
N-(4-fluoro-3-(trifluoromethoxy)phenyl)-2-isobutyl-3-(1-methyl-1H-pyrazol-4-yl)-1-oxo-1,2,3,4-tetrahydroisoquinoline-4-carboxamide;
N-(3-fluoro-5-(trifluoromethoxy)phenyl)-2-isobutyl-3-(1-methyl-1H-pyrazol-4-yl)-1-oxo-1,2,3,4-tetrahydroisoquinoline-4-carboxamide;
N-(3-cyano-5-fluorophenyl)-6-fluoro-2-isobutyl-3-(1-methyl-1H-pyrazol-4-yl)-1-oxo-1,2,3,4-tetrahydroisoquinoline-4-carboxamide;
N-(3-cyano-4-fluorophenyl)-1-oxo-3-(1H-pyrazol-4-yl)-2-(2,2,2-trifluoroethyl)-1,2,3,4-tetrahydroisoquinoline-4-carboxamide;
N-(3-chloro-5-cyanophenyl)-1-oxo-3-(1H-pyrazol-4-yl)-2-(2,2,2-trifluoroethyl)-1,2,3,4-tetrahydroisoquinoline-4-carboxamide;
N-(3-cyanophenyl)-1-oxo-3-(1H-pyrazol-4-yl)-2-(2,2,2-trifluoroethyl)-1,2,3,4-tetrahydroisoquinoline-4-carboxamide;
N-(3-cyano-5-fluorophenyl)-1-oxo-3-(1H-pyrazol-4-yl)-2-(2,2,2-trifluoroethyl)-1,2,3,4-tetrahydroisoquinoline-4-carboxamide;
1-oxo-3-(1H-pyrazol-4-yl)-2-(2,2,2-trifluoroethyl)-N-(3-(trifluoromethoxy)phenyl)-1,2,3,4-tetrahydroisoquinoline-4-carboxamide;
N-(4-fluoro-3-(trifluoromethoxy)phenyl)-1-oxo-3-(1H-pyrazol-4-yl)-2-(2,2,2-trifluoroethyl)-1,2,3,4-tetrahydroisoquinoline-4-carboxamide;
N-(3-fluoro-5-(trifluoromethoxy)phenyl)-1-oxo-3-(1H-pyrazol-4-yl)-2-(2,2,2-trifluoroethyl)-1,2,3,4-tetrahydroisoquinoline-4-carboxamide;
N-(3-cyano-4-fluorophenyl)-7-fluoro-2-isobutyl-3-(1-methyl-1H-pyrazol-4-yl)-1-oxo-1,2,3,4-tetrahydroisoquinoline-4-carboxamide;
N-(3-cyano-4-fluorophenyl)-2-isobutyl-1-oxo-3-(1H-pyrazol-4-yl)-1,2,3,4-tetrahydroisoquinoline-4-carboxamide;
N-(3-chloro-5-cyanophenyl)-2-isobutyl-1-oxo-3-(1H-pyrazol-4-yl)-1,2,3,4-tetrahydroisoquinoline-4-carboxamide;
N-(3-cyanophenyl)-2-isobutyl-1-oxo-3-(1H-pyrazol-4-yl)-1,2,3,4-tetrahydroisoquinoline-4-carboxamide;
N-(3-cyano-5-fluorophenyl)-2-isobutyl-1-oxo-3-(1H-pyrazol-4-yl)-1,2,3,4-tetrahydroisoquinoline-4-carboxamide;
2-isobutyl-1-oxo-3-(1H-pyrazol-4-yl)-N-(3-(trifluoromethoxy)phenyl)-1,2,3,4-tetrahydroisoquinoline-4-carboxamide;
N-(4-fluoro-3-(trifluoromethoxy)phenyl)-2-isobutyl-1-oxo-3-(1H-pyrazol-4-yl)-1,2,3,4-tetrahydroisoquinoline-4-carboxamide;
N-(3-fluoro-5-(trifluoromethoxy)phenyl)-2-isobutyl-1-oxo-3-(1H-pyrazol-4-yl)-1,2,3,4-tetrahydroisoquinoline-4-carboxamide;
N-(3-chloro-5-cyanophenyl)-7-fluoro-2-isobutyl-3-(1-methyl-1H-pyrazol-4-yl)-1-oxo-1,2,3,4-tetrahydroisoquinoline-4-carboxamide;
N-(3-cyano-4-fluorophenyl)-2-isobutyl-3-(isothiazol-4-yl)-1-oxo-1,2,3,4-tetrahydroisoquinoline-4-carboxamide;
N-(3-cyano-4-fluorophenyl)-2-isobutyl-1-oxo-3-(pyrimidin-5-yl)-1,2,3,4-tetrahydroisoquinoline-4-carboxamide; and
N-(3-cyano-4-fluorophenyl)-1-oxo-3-(1H-pyrazol-4-yl-6,7-difluoro-2-(2,2,2-trifluoroethyl)-1,2,3,4-tetrahydroisoquinoline-4-carboxamide.

According to another aspect, the invention relates to compounds of the invention selected from the following group:
N-(3-cyano-4-fluorophenyl)-1-oxo-3-(pyridin-3-yl)-2-(2,2,2-trifluoroethyl)-1,2,3,4-tetrahydroisoquinoline-4-carboxamide;
N-(3-chloro-5-cyanophenyl)-1-oxo-3-(pyridin-3-yl)-2-(2,2,2-trifluoroethyl)-1,2,3,4-tetrahydroisoquinoline-4-carboxamide;
N-(3-cyanophenyl)-1-oxo-3-(pyridin-3-yl)-2-(2,2,2-trifluoroethyl)-1,2,3,4-tetrahydroisoquinoline-4-carboxamide;
N-(3-cyano-5-fluorophenyl)-1-oxo-3-(pyridin-3-yl)-2-(2,2,2-trifluoroethyl)-1,2,3,4-tetrahydroisoquinoline-4-carboxamide;
1-oxo-3-(pyridin-3-yl)-2-(2,2,2-trifluoroethyl)-N-(3-(trifluoromethoxy)phenyl)-1,2,3,4-tetrahydroisoquinoline-4-carboxamide;
N-(4-fluoro-3-(trifluoromethoxy)phenyl)-1-oxo-3-(pyridin-3-yl)-2-(2,2,2-trifluoroethyl)-1,2,3,4-tetrahydroisoquinoline-4-carboxamide;
N-(3-fluoro-5-(trifluoromethoxy)phenyl)-1-oxo-3-(pyridin-3-yl)-2-(2,2,2-trifluoroethyl)-1,2,3,4-tetrahydroisoquinoline-4-carboxamide;
N-(3-cyano-5-fluorophenyl)-7-fluoro-3-(1-methyl-1H-pyrazol-4-yl)-1-oxo-2-(2,2,2-trifluoroethyl)-1,2,3,4-tetrahydroisoquinoline-4-carboxamide;
N-(3-cyano-4-fluorophenyl)-2-isobutyl-7-methoxy-1-oxo-3-(pyridin-3-yl)-1,2,3,4-tetrahydroisoquinoline-4-carboxamide;N-(3-cyano-4-fluorophenyl)-2isobutyl-1-oxo-3-(pyridin-3-yl)-1,2,3,4-tetrahydroisoquinoline-4-carboxamide;
N-(3-chloro-5-cyanophenyl)-2-isobutyl-1-oxo-3-(pyridin-3-yl)-1,2,3,4-tetrahydroisoquinoline-4-carboxamide;
N-(3-cyanophenyl)-2-isobutyl-1-oxo-3-(pyridin-3-yl)-1,2,3,4-tetrahydroisoquinoline-4-carboxamide;
N-(3-cyano-5-fluorophenyl)-2-isobutyl-1-oxo-3-(pyridin-3-yl)-1,2,3,4-tetrahydroisoquinoline-4-carboxamide;
2-isobutyl-1-oxo-3-(pyridin-3-yl)-N-(3-(trifluoromethoxy)phenyl)-1,2,3,4-tetrahydroisoquinoline-4-carboxamide;
N-(4-fluoro-3-(trifluoromethoxy)phenyl)-2-isobutyl-1-oxo-3-(pyridin-3-yl)-1,2,3,4-tetrahydroisoquinoline-4-carboxamide;
N-(3-fluoro-5-(trifluoromethoxy)phenyl)-2-isobutyl-1-oxo-3-(pyridin-3-yl)-1,2,3,4-tetrahydroisoquinoline-4-carboxamide;

N-(3-cyanophenyl)-6-fluoro-2-isobutyl-3-(1-methyl-1H-pyrazol-4-yl)-1-oxo-1,2,3,4-tetrahydroisoquinoline-4-carboxamide;
N-(3-cyano-4-fluorophenyl)-3-(1-methyl-1H-pyrazol-4-yl)-1-oxo-2-(2,2,2-trifluoroethyl)-1,2,3,4-tetrahydroisoquinoline-4-carboxamide;
N-(3-chloro-5-cyanophenyl)-3-(1-methyl-1H-pyrazol-4-yl)-1-oxo-2-(2,2,2-trifluoroethyl)-1,2,3,4-tetrahydroisoquinoline-4-carboxamide;
N-(3-cyanophenyl)-3-(1-methyl-1H-pyrazol-4-yl)-1-oxo-2-(2,2,2-trifluoroethyl)-1,2,3,4-tetrahydroisoquinoline-4-carboxamide;
N-(3-cyano-5-fluorophenyl)-3-(1-methyl-1H-pyrazol-4-yl)-1-oxo-2-(2,2,2-trifluoroethyl)-1,2,3,4-tetrahydroisoquinoline-4-carboxamide;
3-(1-methyl-1H-pyrazol-4-yl)-1-oxo-2-(2,2,2-trifluoroethyl)-N-(3-(trifluoromethoxy)phenyl)-1,2,3,4-tetrahydroisoquinoline-4-carboxamide;
N-(4-fluoro-3-(trifluoromethoxy)phenyl)-3-(1-methyl-1H-pyrazol-4-yl)-1-oxo-2-(2,2,2-trifluoroethyl)-1,2,3,4-tetrahydroisoquinoline-4-carboxamide;
N-(3-fluoro-5-(trifluoromethoxy)phenyl)-3-(1-methyl-1H-pyrazol-4-yl)-1-oxo-2-(2,2,2-trifluoroethyl)-1,2,3,4-tetrahydroisoquinoline-4-carboxamide;
N-(3-cyano-4-fluorophenyl)-2-isobutyl-3-(1-methyl-1H-pyrazol-4-yl)-1-oxo-1,2,3,4-tetrahydroisoquinoline-4-carboxamide;
N-(3-chloro-5-cyanophenyl)-2-isobutyl-3-(1-methyl-1H-pyrazol-4-yl)-1-oxo-1,2,3,4-tetrahydroisoquinoline-4-carboxamide;
N-(3-cyanophenyl)-2-isobutyl-3-(1-methyl-1H-pyrazol-4-yl)-1-oxo-1,2,3,4-tetrahydroisoquinoline-4-carboxamide;
N-(3-cyano-5-fluorophenyl)-2-isobutyl-3-(1-methyl-1H-pyrazol-4-yl)-1-oxo-1,2,3,4-tetrahydroisoquinoline-4-carboxamide;
2-isobutyl-3-(1-methyl-1H-pyrazol-4-yl)-1-oxo-N-(3-(trifluoromethoxy)phenyl)-1,2,3,4-tetrahydroisoquinoline-4-carboxamide;
N-(4-fluoro-3-(trifluoromethoxy)phenyl)-2-isobutyl-3-(1-methyl-1H-pyrazol-4-yl)-1-oxo-1,2,3,4-tetrahydroisoquinoline-4-carboxamide;
N-(3-fluoro-5-(trifluoromethoxy)phenyl)-2-isobutyl-3-(1-methyl-1H-pyrazol-4-yl)-1-oxo-1,2,3,4-tetrahydroisoquinoline-4-carboxamide;
N-(3-cyano-5-fluorophenyl)-6-fluoro-2-isobutyl-3-(1-methyl-1H-pyrazol-4-yl)-1-oxo-1,2,3,4-tetrahydroisoquinoline-4-carboxamide;
N-(3-cyano-4-fluorophenyl)-1-oxo-3-(1H-pyrazol-4-yl)-2-(2,2,2-trifluoroethyl)-1,2,3,4-tetrahydroisoquinoline-4-carboxamide;
N-(3-chloro-5-cyanophenyl)-1-oxo-3-(1H-pyrazol-4-yl)-2-(2,2,2-trifluoroethyl)-1,2,3,4-tetrahydroisoquinoline-4-carboxamide;
N-(3-cyanophenyl)-1-oxo-3-(1H-pyrazol-4-yl)-2-(2,2,2-trifluoroethyl)-1,2,3,4-tetrahydroisoquinoline-4-carboxamide;
N-(3-cyano-5-fluorophenyl)-1-oxo-3-(1H-pyrazol-4-yl)-2-(2,2,2-trifluoroethyl)-1,2,3,4-tetrahydroisoquinoline-4-carboxamide;
1-oxo-3-(1H-pyrazol-4-yl)-2-(2,2,2-trifluoroethyl)-N-(3-(trifluoromethoxy)phenyl)-1,2,3,4-tetrahydroisoquinoline-4-carboxamide;
N-(4-fluoro-3-(trifluoromethoxy)phenyl)-1-oxo-3-(1H-pyrazol-4-yl)-2-(2,2,2-trifluoroethyl)-1,2,3,4-tetrahydroisoquinoline-4-carboxamide;
N-(3-fluoro-5-(trifluoromethoxy)phenyl)-1-oxo-3-(1H-pyrazol-4-yl)-2-(2,2,2-trifluoroethyl)-1,2,3,4-tetrahydroisoquinoline-4-carboxamide;
N-(3-cyano-4-fluorophenyl)-7-fluoro-2-isobutyl-3-(1-methyl-1H-pyrazol-4-yl)-1-oxo-1,2,3,4-tetrahydroisoquinoline-4-carboxamide;
N-(3-cyano-4-fluorophenyl)-2-isobutyl-1-oxo-3-(1H-pyrazol-4-yl)-1,2,3,4-tetrahydroisoquinoline-4-carboxamide;
N-(3-chloro-5-cyanophenyl)-2-isobutyl-1-oxo-3-(1H-pyrazol-4-yl)-1,2,3,4-tetrahydroisoquinoline-4-carboxamide;
N-(3-cyanophenyl)-2-isobutyl-1-oxo-3-(1H-pyrazol-4-yl)-1,2,3,4-tetrahydroisoquinoline-4-carboxamide;
N-(3-cyano-5-fluorophenyl)-2-isobutyl-1-oxo-3-(1H-pyrazol-4-yl)-1,2,3,4-tetrahydroisoquinoline-4-carboxamide;
2-isobutyl-1-oxo-3-(1H-pyrazol-4-yl)-N-(3-(trifluoromethoxy)phenyl)-1,2,3,4-tetrahydroisoquinoline-4-carboxamide;
N-(4-fluoro-3-(trifluoromethoxy)phenyl)-2-isobutyl-1-oxo-3-(1H-pyrazol-4-yl)-1,2,3,4-tetrahydroisoquinoline-4-carboxamide;
N-(3-fluoro-5-(trifluoromethoxy)phenyl)-2-isobutyl-1-oxo-3-(1H-pyrazol-4-yl)-1,2,3,4-tetrahydroisoquinoline-4-carboxamide;
N-(3-chloro-5-cyanophenyl)-7-fluoro-2-isobutyl-3-(1-methyl-1H-pyrazol-4-yl)-1-oxo-1,2,3,4-tetrahydroisoquinoline-4-carboxamide; and
N-(3-cyano-4-fluorophenyl)-1-oxo-3-(1H-pyrazol-4-yl-6,7-difluoro-2-(2,2,2-trifluoroethyl)-1,2,3,4-tetrahydroisoquinoline-4-carboxamide.

According to another aspect, the invention relates to compounds of the invention selected from the following group:
N-(3-cyano-4-fluorophenyl)-1-oxo-3-(1H-pyrazol-4-yl)-2-(2,2,2-trifluoroethyl)-1,2,3,4-tetrahydroisoquinoline-4-carboxamide;
N-(3-cyano-4-fluorophenyl)-1-oxo-3-(pyridin-3-yl)-2-(2,2,2-trifluoroethyl)-1,2,3,4-tetrahydroisoquinoline-4-carboxamide; and
N-(3-cyano-5-fluorophenyl)-1-oxo-3-(1H-pyrazol-4-yl)-2-(2,2,2-trifluoroethyl)-1,2,3,4-tetrahydroisoquinoline-4-carboxamide.

According to another aspect, the invention relates to compounds of the invention selected from the following group:
d-N-(3-cyano-4-fluorophenyl)-1-oxo-3-(1H-pyrazol-4-yl)-2-(2,2,2-trifluoroethyl)-1,2,3,4-tetrahydroisoquinoline-4-carboxamide;
d-N-(3-cyano-4-fluorophenyl)-1-oxo-3-(pyridin-3-yl)-2-(2,2,2-trifluoroethyl)-1,2,3,4-tetrahydroisoquinoline-4-carboxamide; and
d-N-(3-cyano-5-fluorophenyl)-1-oxo-3-(1H-pyrazol-4-yl)-2-(2,2,2-trifluoroethyl)-1,2,3,4-tetrahydroisoquinoline-4-carboxamide.

3. Specified Examples

In various specific aspects, the compounds can be selected such that $Ar^1$ is selected from 5-cyano-2-thiopheneyl, 3-pyridinyl, 4-isoxazolyl, N-methyl-4-pyrazolyl, 4-pyrazolyl, 4-isothiazolyl, 5-thiazolyl, 5-pyrimidinyl, and 4-pyridazinyl. In various specific aspects, the compounds can be selected such that $R^1$ is isopropyl or trifluoromethyl. In various specific aspects, the compounds can be selected such that $R^2$ is selected from hydrogen and fluoro. In various specific aspects, the compounds can be selected such that $R^3$ is selected from hydrogen, chloro, and fluoro. In various specific aspects, the compounds can be selected such that $Ar^2$ is selected from 3-(trifluoromethoxy)phenyl, 3-(trifluoromethyl)phenyl, 3-chloro-5-cyanophenyl, 3-cyano-4-fluorophenyl, 3-cyano-5-fluorophenyl, 3-fluoro-5-(trifluoromethoxy)phenyl, 3-fluoro-5-(trifluoromethyl)phenyl, 4-fluoro-3-(trifluoromethoxy) phenyl, and 4-fluoro-3-(trifluoromethyl)phenyl.

Accordingly, in one specific aspect, the invention relates to compounds having a structure represented by a formula:

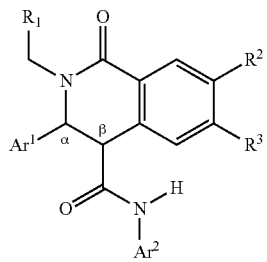
(II)

wherein Ar¹ is selected from 5-cyano-2-thiopheneyl, 3-pyridinyl, 4-isoxazolyl, N-methyl-4-pyrazolyl, 4-pyrazolyl, 4-isothiazolyl, 5-thiazolyl, 5-pyrimidinyl, and 4-pyridazinyl; wherein R¹ is isopropyl or trifluoromethyl; wherein R² is selected from hydrogen and fluoro; wherein R³ is selected from hydrogen, chloro, and fluoro; wherein ring substituents at the carbon atoms denoted with labels α and β have a trans configuration; and wherein Ar² is selected from 3-(trifluoromethoxy)phenyl, 3-(trifluoromethyl)phenyl, 3-chloro-5-cyanophenyl, 3-cyano-4-fluorophenyl, 3-cyano-5-fluorophenyl, 3-fluoro-5-(trifluoromethoxy)phenyl, 3-fluoro-5-(trifluoromethyl)phenyl, 4-fluoro-3-(trifluoromethoxy)phenyl, and 4-fluoro-3-(trifluoromethyl)phenyl, or a pharmaceutically acceptable salt, hydrate, solvate, or polymorph thereof, as well as tautomers, geometrical isomers, and optically active forms thereof.

In a further aspect, compounds of the invention are dextrorotatory (d) and have a (+)-sign of optical rotation. In a further aspect, the compound exhibits activity against one or more eukaryotic protists of the genus *Plasmodium*.

In the various disclosed aspects, such compounds exhibit: improved physiochemical properties (e.g., solubility), improved potency, improved oral exposure, improved oral efficacy in the mouse, improved metabolic stability, and potential reduction in potential toxicity. It is appreciated that the compounds of the various aspects can be provided by the disclosed methods. It is also understood that the compounds of the various aspects can be employed in the disclosed methods of using. In further aspects, a compound can be present as one or more of the compounds shown in Table II, or a subgroup thereof:

TABLE II

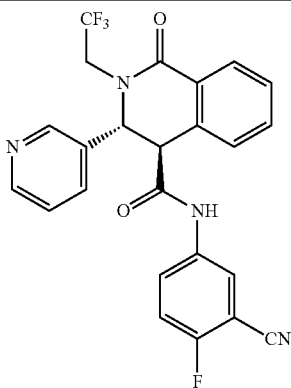

TABLE II-continued

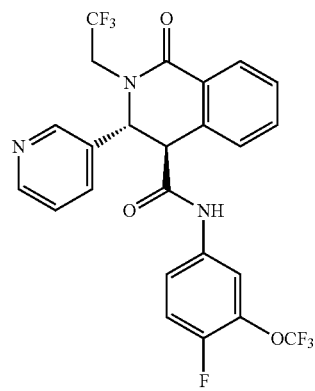 [SMILES: O=C(Nc1ccc(F)c(OC(F)(F)F)c1)[C@@H]1c2ccccc2C(=O)N(CC(F)(F)F)[C@H]1c1cccnc1]

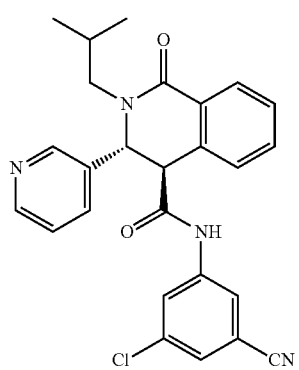 [SMILES: CC(C)CN1C(=O)c2ccccc2[C@@H](C(=O)Nc2cc(Cl)cc(C#N)c2)[C@@H]1c1cccnc1]

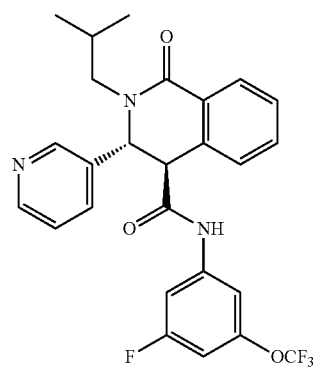 [SMILES: CC(C)CN1C(=O)c2ccccc2[C@@H](C(=O)Nc2cc(F)cc(OC(F)(F)F)c2)[C@@H]1c1cccnc1]

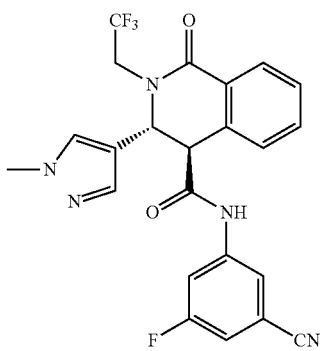 [SMILES: CN/C=C(\C=N)[C@H]1[C@H](C(=O)Nc2cc(F)cc(C#N)c2)c2ccccc2C(=O)N1CC(F)(F)F]

TABLE II-continued
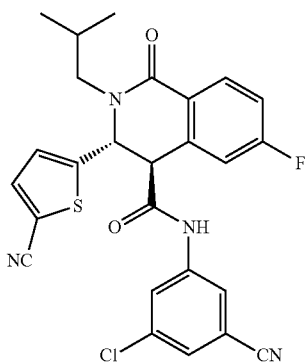
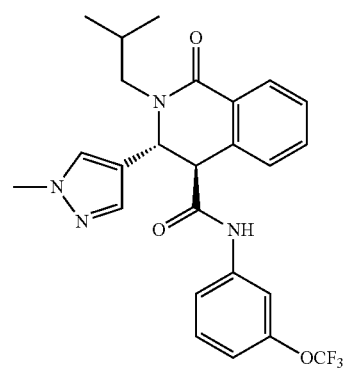 [SMILES: CC(C)CN1C(=O)c2ccccc2[C@@H](C(=O)Nc2cccc(OC(F)(F)F)c2)[C@@H]1c1cnn(C)c1]
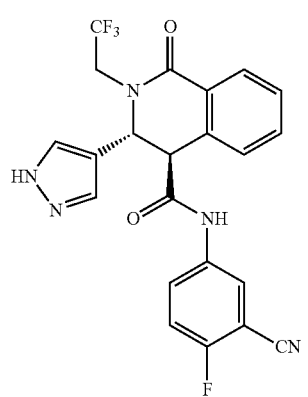 [SMILES: N#Cc1cc(NC(=O)[C@@H]2c3ccccc3C(=O)N(CC(F)(F)F)[C@H]2c2cn[nH]c2)ccc1F]
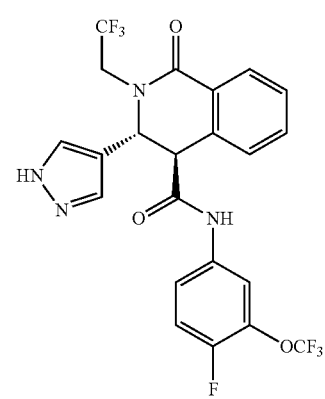 [SMILES: O=C(Nc1ccc(F)c(OC(F)(F)F)c1)[C@@H]1c2ccccc2C(=O)N(CC(F)(F)F)[C@H]1c1cn[nH]c1]
TABLE II-continued
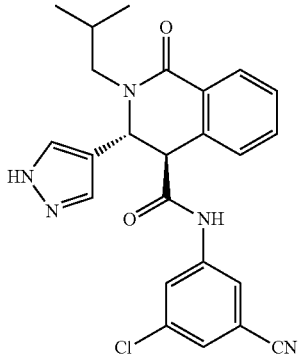
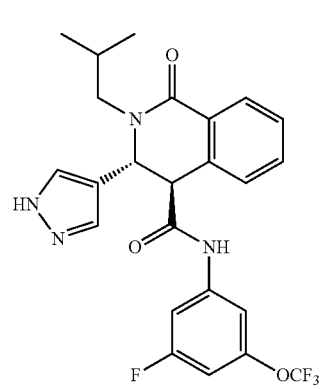 [SMILES: CC(C)CN1C(=O)c2ccccc2[C@@H](C(=O)Nc2cc(F)cc(OC(F)(F)F)c2)[C@@H]1c1cn[nH]c1]
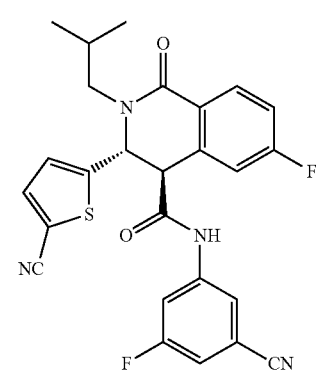 [SMILES: CC(C)CN1C(=O)c2ccc(F)cc2[C@@H](C(=O)Nc2cc(F)cc(C#N)c2)[C@@H]1c1ccc(C#N)s1]
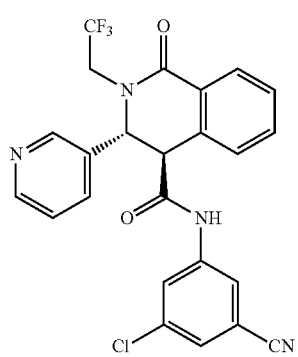 [SMILES: N#Cc1cc(Cl)cc(NC(=O)[C@@H]2c3ccccc3C(=O)N(CC(F)(F)F)[C@H]2c2cccnc2)c1]

TABLE II-continued
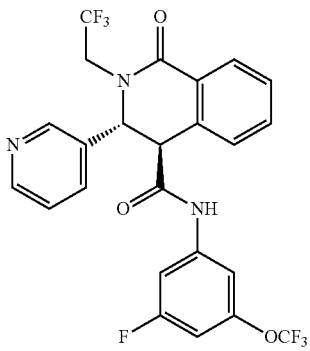 [SMILES: O=C(Nc1cc(F)cc(OC(F)(F)F)c1)[C@@H]1c2ccccc2C(=O)N(CC(F)(F)F)[C@H]1c1cccnc1]
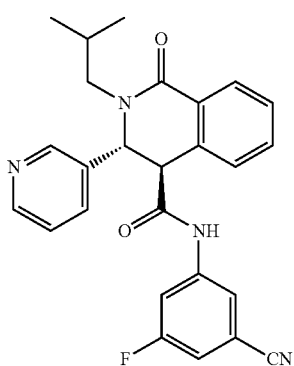 [SMILES: CC(C)CN1C(=O)c2ccccc2[C@@H](C(=O)Nc2cc(F)cc(C#N)c2)[C@@H]1c1cccnc1]
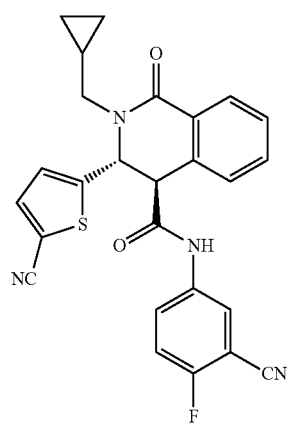 [SMILES: N#Cc1ccc([C@H]2[C@H](C(=O)Nc3ccc(F)c(C#N)c3)c3ccccc3C(=O)N2CC2CC2)s1]
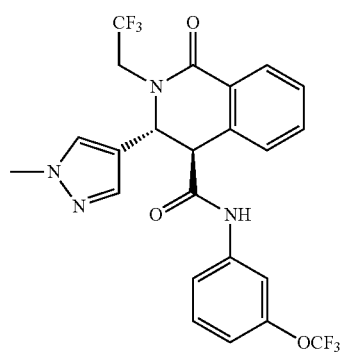 [SMILES: Cn1cc([C@H]2[C@H](C(=O)Nc3cccc(OC(F)(F)F)c3)c3ccccc3C(=O)N2CC(F)(F)F)cn1]
TABLE II-continued
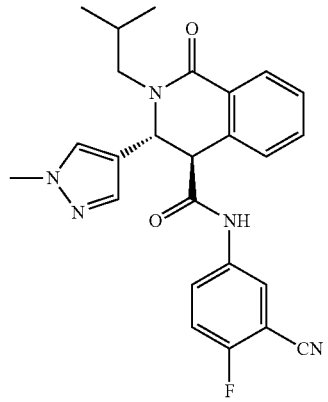 [SMILES: CC(C)CN1C(=O)c2ccccc2[C@@H](C(=O)Nc2ccc(F)c(C#N)c2)[C@@H]1c1cnn(C)c1]
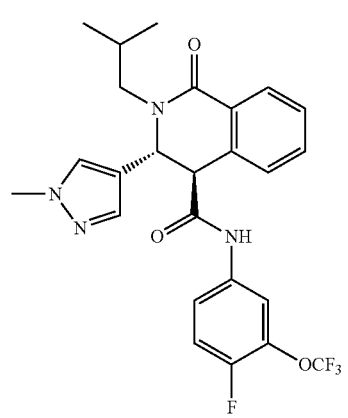 [SMILES: CC(C)CN1C(=O)c2ccccc2[C@@H](C(=O)Nc2ccc(F)c(OC(F)(F)F)c2)[C@@H]1c1cnn(C)c1]
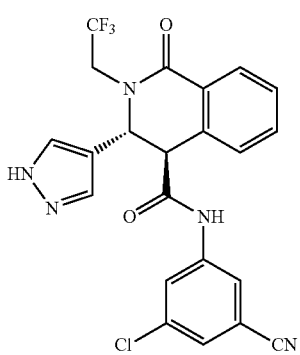 [SMILES: N#Cc1cc(Cl)cc(NC(=O)[C@@H]2c3ccccc3C(=O)N(CC(F)(F)F)[C@H]2c2cn[nH]c2)c1]
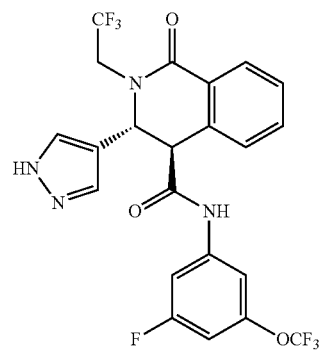 [SMILES: O=C(Nc1cc(F)cc(OC(F)(F)F)c1)[C@@H]1c2ccccc2C(=O)N(CC(F)(F)F)[C@H]1c1cn[nH]c1]

TABLE II-continued
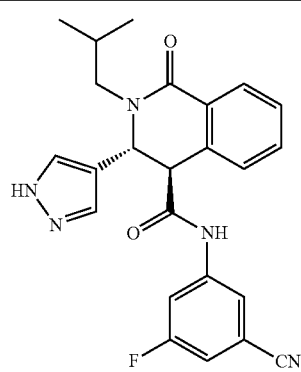
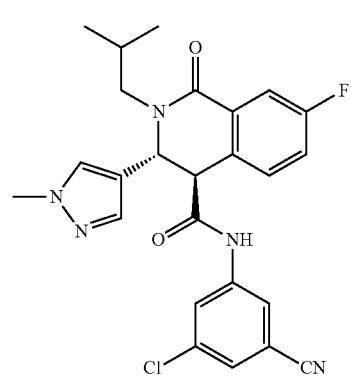 [SMILES: CC(C)CN1C(=O)c2cc(F)ccc2[C@@H](C(=O)Nc2cc(Cl)cc(C#N)c2)[C@@H]1c1cnn(C)c1]
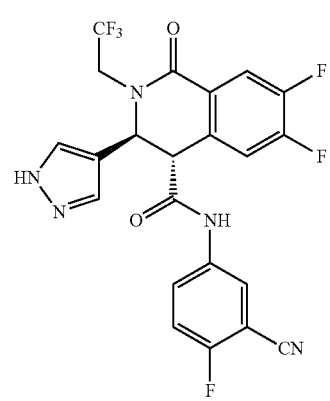 [SMILES: N#Cc1cc(NC(=O)[C@H]2c3cc(F)c(F)cc3C(=O)N(CC(F)(F)F)[C@@H]2c2cn[nH]c2)ccc1F]
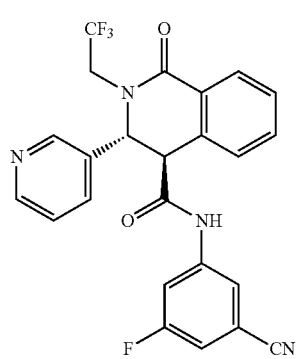 [SMILES: N#Cc1cc(F)cc(NC(=O)[C@@H]2c3ccccc3C(=O)N(CC(F)(F)F)[C@H]2c2cccnc2)c1]
TABLE II-continued
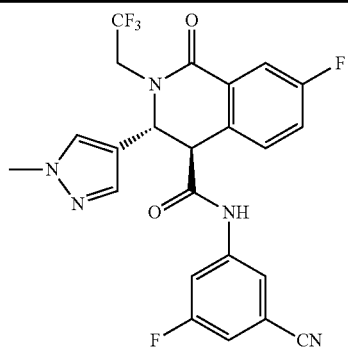
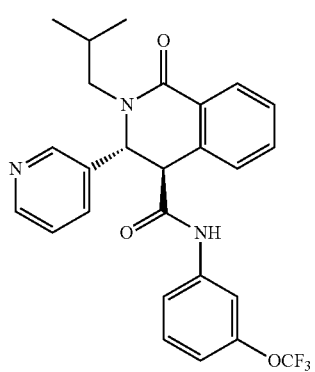 [SMILES: CC(C)CN1C(=O)c2ccccc2[C@@H](C(=O)Nc2cccc(OC(F)(F)F)c2)[C@@H]1c1cccnc1]
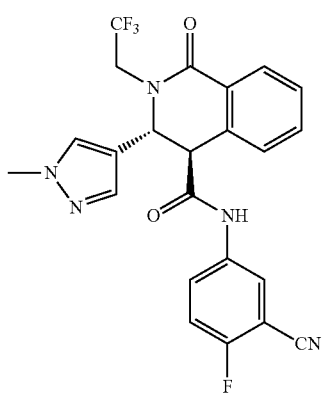 [SMILES: Cn1cc([C@H]2[C@H](C(=O)Nc3ccc(F)c(C#N)c3)c3ccccc3C(=O)N2CC(F)(F)F)cn1]
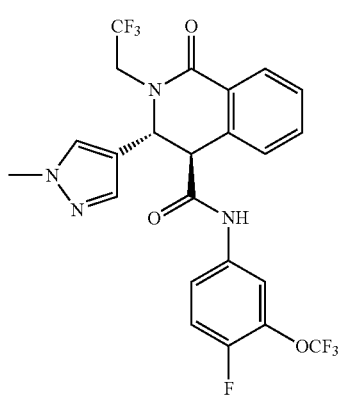 [SMILES: Cn1cc([C@H]2[C@H](C(=O)Nc3ccc(F)c(OC(F)(F)F)c3)c3ccccc3C(=O)N2CC(F)(F)F)cn1]

TABLE II-continued
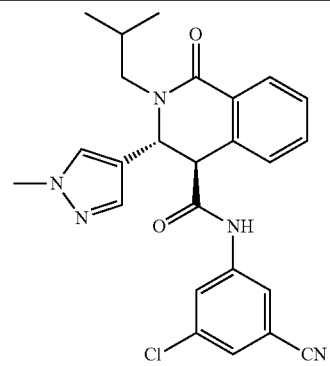
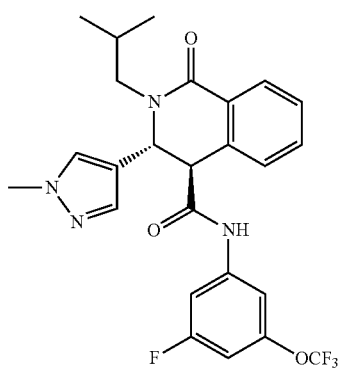 [SMILES: CC(C)CN1C(=O)c2ccccc2[C@@H](C(=O)Nc2cc(F)cc(OC(F)(F)F)c2)[C@@H]1c1cnn(C)c1]
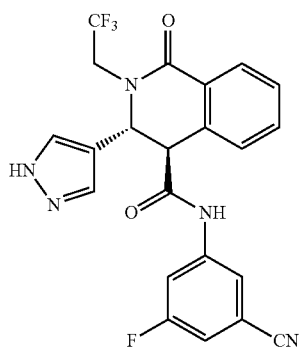
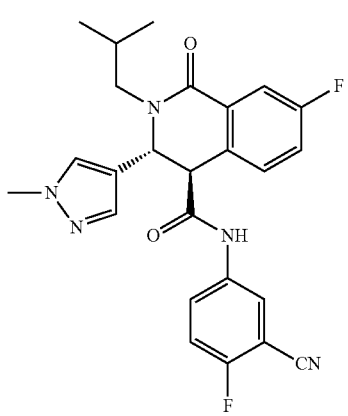 [SMILES: CC(C)CN1C(=O)c2cc(F)ccc2[C@@H](C(=O)Nc2ccc(F)c(C#N)c2)[C@@H]1c1cnn(C)c1]
TABLE II-continued
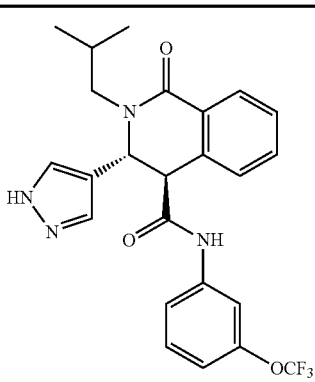
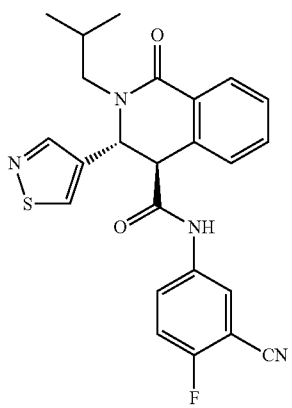 [SMILES: CC(C)CN1C(=O)c2ccccc2[C@@H](C(=O)Nc2ccc(F)c(C#N)c2)[C@@H]1c1cnsc1]
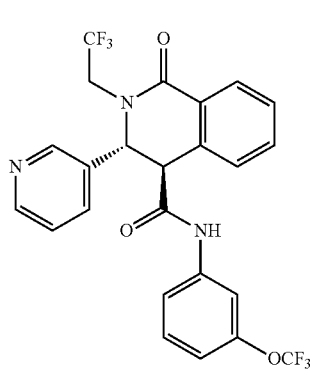 [SMILES: O=C(Nc1cccc(OC(F)(F)F)c1)[C@@H]1c2ccccc2C(=O)N(CC(F)(F)F)[C@H]1c1cccnc1]
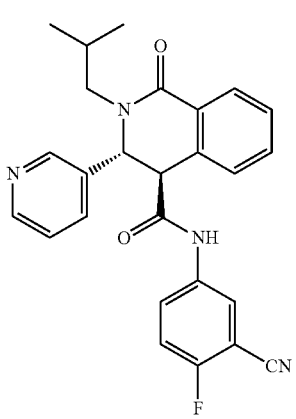 [SMILES: CC(C)CN1C(=O)c2ccccc2[C@@H](C(=O)Nc2ccc(F)c(C#N)c2)[C@@H]1c1cccnc1]

TABLE II-continued
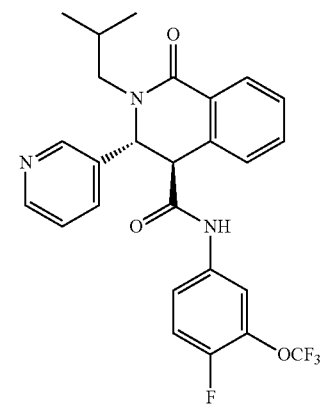 [SMILES: CC(C)CN1C(=O)c2ccccc2[C@@H](C(=O)Nc2ccc(F)c(OC(F)(F)F)c2)[C@@H]1c1cccnc1]
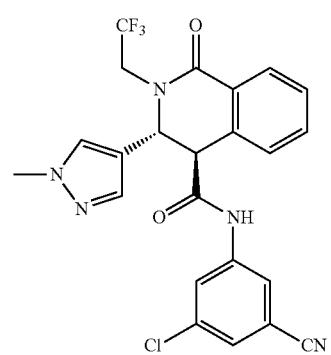 [SMILES: Cn1cc([C@H]2[C@H](C(=O)Nc3cc(Cl)cc(C#N)c3)c3ccccc3C(=O)N2CC(F)(F)F)cn1]
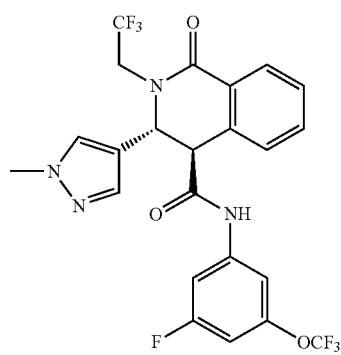 [SMILES: Cn1cc([C@H]2[C@H](C(=O)Nc3cc(F)cc(OC(F)(F)F)c3)c3ccccc3C(=O)N2CC(F)(F)F)cn1]
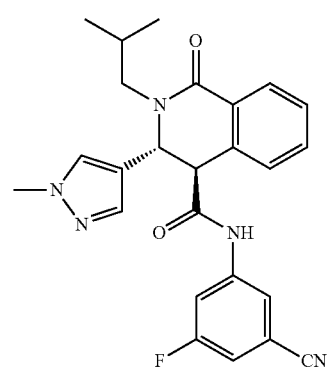
TABLE II-continued
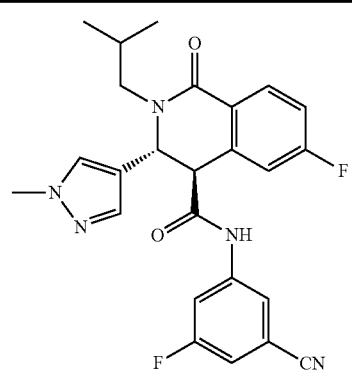
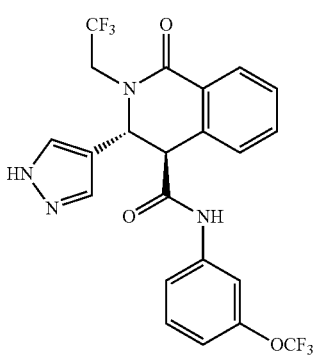 [SMILES: O=C(Nc1cccc(OC(F)(F)F)c1)[C@@H]1c2ccccc2C(=O)N(CC(F)(F)F)[C@H]1c1cn[nH]c1]
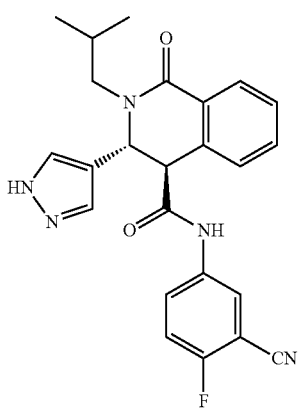 [SMILES: CC(C)CN1C(=O)c2ccccc2[C@@H](C(=O)Nc2ccc(F)c(C#N)c2)[C@@H]1c1cn[nH]c1]
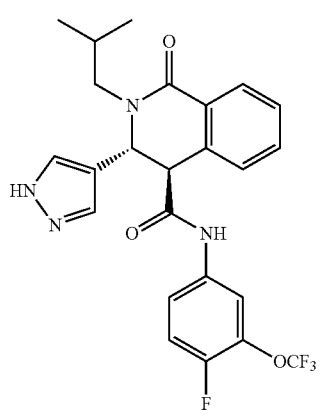 [SMILES: CC(C)CN1C(=O)c2ccccc2[C@@H](C(=O)Nc2ccc(F)c(OC(F)(F)F)c2)[C@@H]1c1cn[nH]c1]

TABLE II-continued

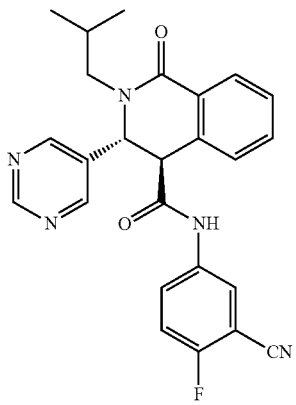 [SMILES: CC(C)CN1C(=O)c2ccccc2[C@@H](C(=O)Nc2ccc(F)c(C#N)c2)[C@@H]1c1cncnc1]

According to one aspect of the invention, the compounds are selected from the following group:

N-(3-cyano-4-fluorophenyl)-1-oxo-3-(pyridin-3-yl)-2-(2,2,2-trifluoroethyl)-1,2,3,4-tetrahydroisoquinoline-4-carboxamide;
N-(3-chloro-5-cyanophenyl)-1-oxo-3-(pyridin-3-yl)-2-(2,2,2-trifluoroethyl)-1,2,3,4-tetrahydroisoquinoline-4-carboxamide;
N-(3-cyano-5-fluorophenyl)-1-oxo-3-(pyridin-3-yl)-2-(2,2,2-trifluoroethyl)-1,2,3,4-tetrahydroisoquinoline-4-carboxamide;
1-oxo-3-(pyridin-3-yl)-2-(2,2,2-trifluoroethyl)-N-(3-(trifluoromethoxy)phenyl)-1,2,3,4-tetrahydroisoquinoline-4-carboxamide;
N-(4-fluoro-3-(trifluoromethoxy)phenyl)-1-oxo-3-(pyridin-3-yl)-2-(2,2,2-trifluoroethyl)-1,2,3,4-tetrahydroisoquinoline-4-carboxamide;
N-(3-fluoro-5-(trifluoromethoxy)phenyl)-1-oxo-3-(pyridin-3-yl)-2-(2,2,2-trifluoroethyl)-1,2,3,4-tetrahydroisoquinoline-4-carboxamide;
N-(3-cyano-5-fluorophenyl)-7-fluoro-3-(1-methyl-1H-pyrazol-4-yl)-1-oxo-2-(2,2,2-trifluoroethyl)-1,2,3,4-tetrahydroisoquinoline-4-carboxamide;
N-(3-cyano-4-fluorophenyl)-2-isobutyl-1-oxo-3-(pyridin-3-yl)-1,2,3,4-tetrahydroisoquinoline-4-carboxamide;
N-(3-chloro-5-cyanophenyl)-2-isobutyl-1-oxo-3-(pyridin-3-yl)-1,2,3,4-tetrahydroisoquinoline-4-carboxamide;
N-(3-cyano-5-fluorophenyl)-2-isobutyl-1-oxo-3-(pyridin-3-yl)-1,2,3,4-tetrahydroisoquinoline-4-carboxamide;
2-isobutyl-1-oxo-3-(pyridin-3-yl)-N-(3-(trifluoromethoxy)phenyl)-1,2,3,4-tetrahydroisoquinoline-4-carboxamide;
N-(4-fluoro-3-(trifluoromethoxy)phenyl)-2-isobutyl-1-oxo-3-(pyridin-3-yl)-1,2,3,4-tetrahydroisoquinoline-4-carboxamide;
N-(3-fluoro-5-(trifluoromethoxy)phenyl)-2-isobutyl-1-oxo-3-(pyridin-3-yl)-1,2,3,4-tetrahydroisoquinoline-4-carboxamide;
N-(3-cyano-4-fluorophenyl)-3-(5-cyanothiophen-2-yl)-2-(cyclopropylmethyl)-1-oxo-1,2,3,4-tetrahydroisoquinoline-4-carboxamide;
N-(3-chloro-5-cyanophenyl)-3-(1-methyl-1H-pyrazol-4-yl)-1-oxo-2-(2,2,2-trifluoroethyl)-1,2,3,4-tetrahydroisoquinoline-4-carboxamide;
N-(3-cyano-5-fluorophenyl)-3-(1-methyl-1H-pyrazol-4-yl)-1-oxo-2-(2,2,2-trifluoroethyl)-1,2,3,4-tetrahydroisoquinoline-4-carboxamide;
3-(1-methyl-1H-pyrazol-4-yl)-1-oxo-2-(2,2,2-trifluoroethyl)-N-(3-(trifluoromethoxy)phenyl)-1,2,3,4-tetrahydroisoquinoline-4-carboxamide;
N-(4-fluoro-3-(trifluoromethoxy)phenyl)-3-(1-methyl-1H-pyrazol-4-yl)-1-oxo-2-(2,2,2-trifluoroethyl)-1,2,3,4-tetrahydroisoquinoline-4-carboxamide;
N-(3-fluoro-5-(trifluoromethoxy)phenyl)-3-(1-methyl-1H-pyrazol-4-yl)-1-oxo-2-(2,2,2-trifluoroethyl)-1,2,3,4-tetrahydroisoquinoline-4-carboxamide;
N-(3-chloro-5-cyanophenyl)-3-(5-cyanothiophen-2-yl)-6-fluoro-2-isobutyl-1-oxo-1,2,3,4-tetrahydroisoquinoline-4-carboxamide;
N-(3-cyano-4-fluorophenyl)-2-isobutyl-3-(1-methyl-1H-pyrazol-4-yl)-1-oxo-1,2,3,4-tetrahydroisoquinoline-4-carboxamide;
N-(3-chloro-5-cyanophenyl)-2-isobutyl-3-(1-methyl-1H-pyrazol-4-yl)-1-oxo-1,2,3,4-tetrahydroisoquinoline-4-carboxamide;
N-(3-cyano-5-fluorophenyl)-2-isobutyl-3-(1-methyl-1H-pyrazol-4-yl)-1-oxo-1,2,3,4-tetrahydroisoquinoline-4-carboxamide;
2-isobutyl-3-(1-methyl-1H-pyrazol-4-yl)-1-oxo-N-(3-(trifluoromethoxy)phenyl)-1,2,3,4-tetrahydroisoquinoline-4-carboxamide;
N-(4-fluoro-3-(trifluoromethoxy)phenyl)-2-isobutyl-3-(1-methyl-1H-pyrazol-4-yl)-1-oxo-1,2,3,4-tetrahydroisoquinoline-4-carboxamide;
N-(3-fluoro-5-(trifluoromethoxy)phenyl)-2-isobutyl-3-(1-methyl-1H-pyrazol-4-yl)-1-oxo-1,2,3,4-tetrahydroisoquinoline-4-carboxamide;
N-(3-cyano-4-fluorophenyl)-1-oxo-3-(1H-pyrazol-4-yl)-2-(2,2,2-trifluoroethyl)-1,2,3,4-tetrahydroisoquinoline-4-carboxamide;
N-(3-chloro-5-cyanophenyl)-1-oxo-3-(1H-pyrazol-4-yl)-2-(2,2,2-trifluoroethyl)-1,2,3,4-tetrahydroisoquinoline-4-carboxamide;
N-(3-cyanophenyl)-1-oxo-3-(1H-pyrazol-4-yl)-2-(2,2,2-trifluoroethyl)-1,2,3,4-tetrahydroisoquinoline-4-carboxamide;
1-oxo-3-(1H-pyrazol-4-yl)-2-(2,2,2-trifluoroethyl)-N-(3-(trifluoromethoxy)phenyl)-1,2,3,4-tetrahydroisoquinoline-4-carboxamide;
N-(4-fluoro-3-(trifluoromethoxy)phenyl)-1-oxo-3-(1H-pyrazol-4-yl)-2-(2,2,2-trifluoroethyl)-1,2,3,4-tetrahydroisoquinoline-4-carboxamide;
N-(3-cyano-4-fluorophenyl)-7-fluoro-2-isobutyl-3-(1-methyl-1H-pyrazol-4-yl)-1-oxo-1,2,3,4-tetrahydroisoquinoline-4-carboxamide;
N-(3-cyano-4-fluorophenyl)-2-isobutyl-1-oxo-3-(1H-pyrazol-4-yl)-1,2,3,4-tetrahydroisoquinoline-4-carboxamide;
N-(3-chloro-5-cyanophenyl)-2-isobutyl-1-oxo-3-(1H-pyrazol-4-yl)-1,2,3,4-tetrahydroisoquinoline-4-carboxamide;
N-(3-cyano-5-fluorophenyl)-2-isobutyl-1-oxo-3-(1H-pyrazol-4-yl)-1,2,3,4-tetrahydroisoquinoline-4-carboxamide;
2-isobutyl-1-oxo-3-(1H-pyrazol-4-yl)-N-(3-(trifluoromethoxy)phenyl)-1,2,3,4-tetrahydroisoquinoline-4-carboxamide;
N-(4-fluoro-3-(trifluoromethoxy)phenyl)-2-isobutyl-1-oxo-3-(1H-pyrazol-4-yl)-1,2,3,4-tetrahydroisoquinoline-4-carboxamide;
N-(3-fluoro-5-(trifluoromethoxy)phenyl)-2-isobutyl-1-oxo-3-(1H-pyrazol-4-yl)-1,2,3,4-tetrahydroisoquinoline-4-carboxamide;
N-(3-chloro-5-cyanophenyl)-7-fluoro-2-isobutyl-3-(1-methyl-1H-pyrazol-4-yl)-1-oxo-1,2,3,4-tetrahydroisoquinoline-4-carboxamide;
N-(3-cyano-4-fluorophenyl)-2-isobutyl-3-(isothiazol-4-yl)-1-oxo-1,2,3,4-tetrahydroisoquinoline-4-carboxamide;
N-(3-cyano-4-fluorophenyl)-2-isobutyl-1-oxo-3-(pyrimidin-5-yl)-1,2,3,4-tetrahydroisoquinoline-4-carboxamide;

N-(3-cyano-5-fluorophenyl)-3-(5-cyanothiophen-2-yl)-6-fluoro-2-isobutyl-1-oxo-1,2,3,4-tetrahydroisoquinoline-4-carboxamide; and C. N-(3-Cyano-4-Fluorophenyl)-1-oxo-3-(1H-Pyrazol-4-Yl-6,7-Difluoro-(2,2,2-Trifluoroethyl)-1,2,3,4-Tetrahydroisoquinoline-4-Carboxamide. Methods of Making the Compounds The compounds of this invention can be prepared by employing reactions as shown in the following schemes, in addition to other standard manipulations that are known in the literature, exemplified in the experimental sections or clear to one skilled in the art. Reactions used to generate the compounds of this invention are prepared by employing reactions as shown in the following Reaction Schemes, in addition to other standard manipulations known in the literature or to one skilled in the art. The following examples are provided so that the invention might be more fully understood, are illustrative only, and should not be construed as limiting.

In one aspect, the invention relates to methods of making substituted 2-alkyl-1-oxo-N-phenyl-3-heteroaryl-1,2,3,4-tetrahydroisoquinoline-4-carboxamides via reaction of an optionally substituted isochroman-1,3-dione with an (E)-N-heteroarylidene-2-alkylpropan-1-amine to yield an anti-2-alkyl-1-oxo-3-heteroaryl-1,2,3,4-tetrahydroisoquinoline-4-carboxylic acid, followed by coupling with an optionally substituted aniline to provide a trans-2-alkyl-1-oxo-N-phenyl-3-heteroaryl-1,2,3,4-tetrahydroisoquinoline-4-carboxamide. Such a reaction sequence is shown generally in Reaction Scheme 1, below:

REACTION SCHEME 1

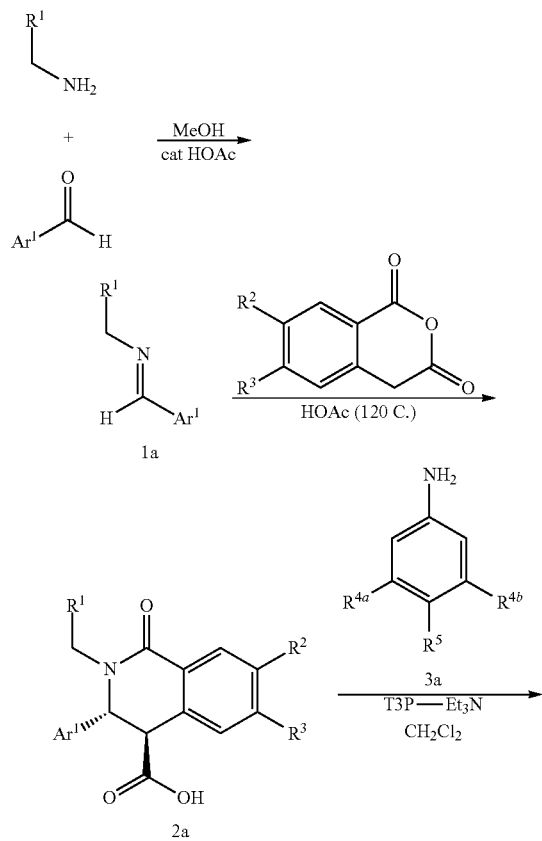

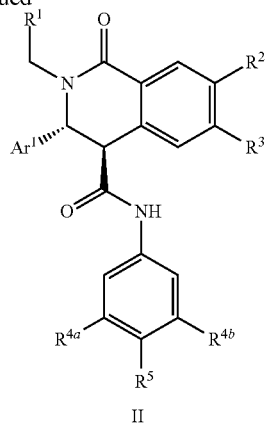

Typically, an optionally substituted aldehyde is reacted with a primary amine in the presence of a catalytic amount of glacial acetic acid to provide a crude aldimine 1a wherein $Ar^1$ and $R^1$ are as defined herein, which after removal of solvent can be used without further purification. The aldimine 1a can then be reacted with optionally substituted isochroman-1,3-dione to provide, after concentration, the trans-acid 2a wherein Ar1 and $R^1$, $R^2$ and $R^3$ are as described herein. Acid 2a can then be coupled with an optionally substituted aniline 3a wherein $R^{4a}$, $R^{4b}$ and $R^5$ are as described herein to provide amides, a racemic mixture of compounds of the invention (IIg) and (IIj). The crude amides can be purified over silica gel to yield the pure compound.

To prepare the individual enantiomers of the amides, the racemic acids 2a may be converted into the corresponding diastereomeric salt forms by reaction with a suitable enantiomerically pure amine. Said diastereomeric salt forms are subsequently separated, for example, by selective or fractional crystallization and the enantiomeric acids 2a are liberated therefrom under acidic conditions. The pure enantiomers of acids 2a are then converted to the pure enantiomers of amides (IIg) and (IIj) An alternative manner of separating the enantiomeric forms of the disclosed compounds involves conversion of acids 2a to their corresponding methyl esters followed by chromatographic separation using a chiral stationary phase and hydrolysis of the esters to give individual enantiomers of acids 2a as exemplified in Example 6 below.

In another aspect, the aldimine 1a can be formed by the reaction of an amine hydrochloride salt and the selected aldehyde in acetonitrile in the presence of triethylamine. Pure 1a is obtained by initial filtration of the reaction mixture, concentration, re-suspension of the residue in diethyl ether, filtration and finally concentration to give pure aldimine 1a. Reaction of 1a with the appropriate substituted isochroman-1,3-dione in acetonitile for 15 hr at 85° C. followed by cooling and filtration affords pure trans-acid 2a in 30-60% yields. Treating a mixture of acids 2a and appropriate corresponding substituted aniline with phosphorous oxychloride in acetonitrile for three hours at 85° C. followed by basic quench and extraction and concentration gives the amides (II) of the invention after chromatographic purification.

According to another aspect, the invention provides a process for the preparation of compounds of formula (II) wherein $Ar^1$ is selected from 3-pyridinyl, 4-(1-methylpyrazolyl) and 4-pyrazolyl; $R^1$ is selected from $CF_3$, propyl, cyclopropyl and $(CH_3)_2CH$; $R^2$ and $R^3$ are independently selected from H, $OCH_3$ and F; $R^{5a}$, $R^{5b}$ and $R^6$ are independently selected from H, CN, F, Cl and $OCF_3$, comprising a step of reacting a carboxylic acid of formula 2a wherein $Ar^1$ is selected from 3-pyridinyl, 4-(1-methylpyrazolyl) and 4-pyrazolyl; $R^1$ is selected from $CF_3$, propyl, cyclopropyl and $(CH_3)_2CH$; and $R^2$ and $R^3$ are independently selected from H, $OCH_3$ and F with an aryl amine of formula 3a wherein $R^{4a}$, $R^{4b}$ and $R^5$ are independently selected from H, CN, F, Cl and $OCF_3$:

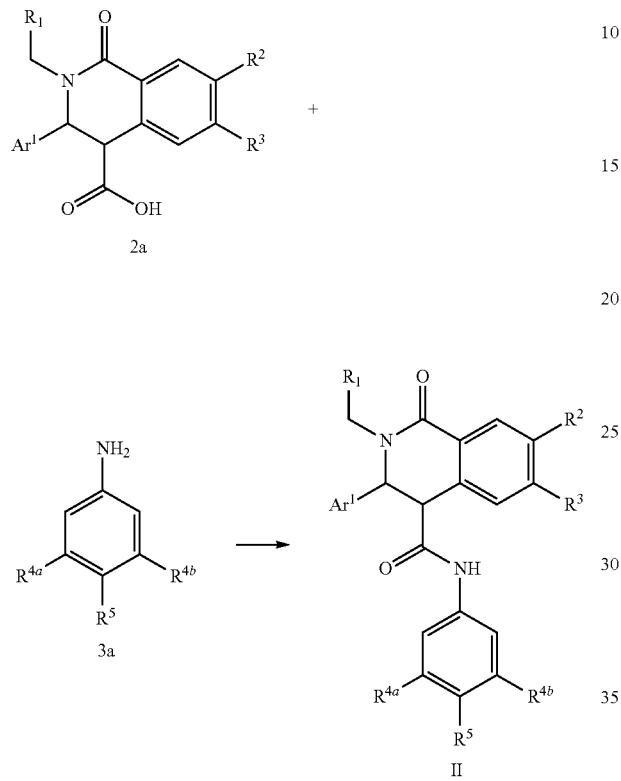

According to another aspect, the invention provides an intermediate of formula 2a selected from the following group:

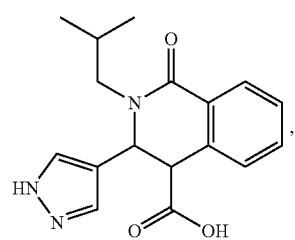
(2a1)

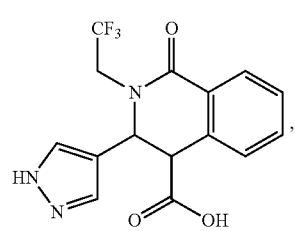
(2a2)

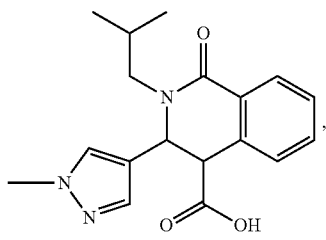
(2a3)

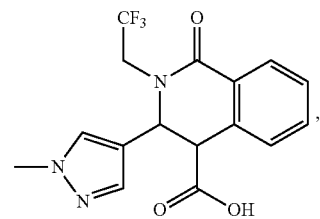
(2a4)

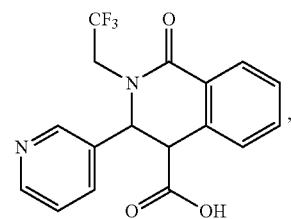
(2a5)

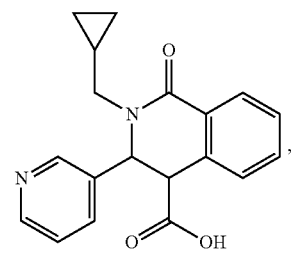
(2a6)

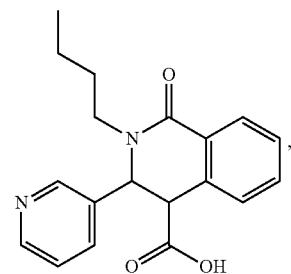
(2a7)

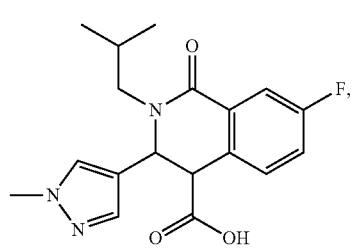
(2a8)

-continued

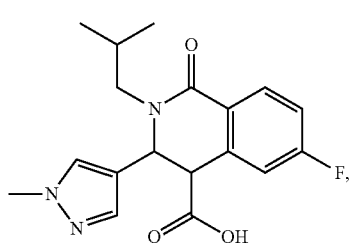 (2a9)

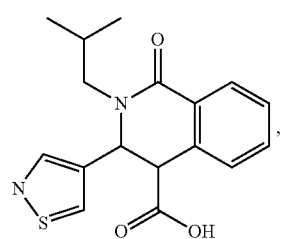 (2a10)

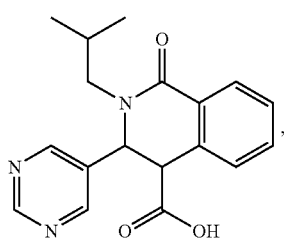 (2a11)

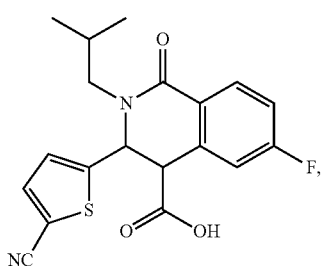 (2a12)

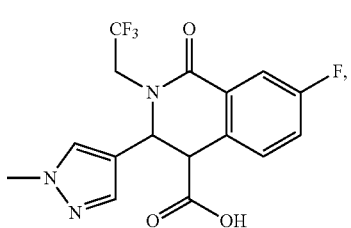 (2a13)

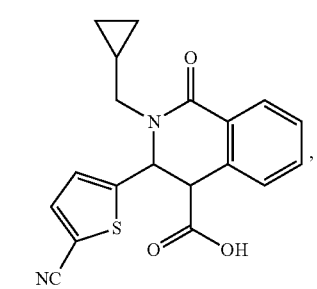 (2a14)

-continued

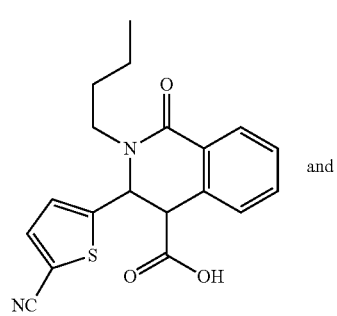 (2a15)

and

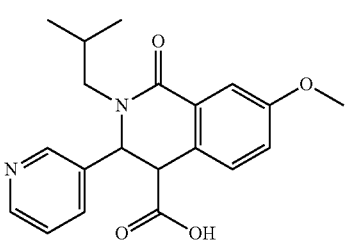 (2a16)

According to another aspect, the invention provides an intermediate of formula 2a selected from the following group:

1-oxo-2-isobutyl-3-(1H-pyrazol-4-yl)-1,2,3,4-tetrahydroisoquinoline-4-carboxylic acid;

1-oxo-2-(2,2,2-trifluoroethyl)-3-(1H-pyrazol-4-yl)-1,2,3,4-tetrahydroisoquinoline-4-carboxylic acid;

1-oxo-2-isobutyl-3-(1-methyl-1H-pyrazol-4-yl)-1,2,3,4-tetrahydroisoquinoline-4-carboxylic acid;

1-oxo-2-(2,2,2-trifluoroethyl)-3-(1-methyl-1H-pyrazol-4-yl)-1,2,3,4-tetrahydroisoquinoline-4-carboxylic acid;

1-oxo-2-(2,2,2-trifluoroethyl)-3-(pyridin-3-yl)-1,2,3,4-tetrahydroisoquinoline-4-carboxylic acid;

1-oxo-2-(cyclopropylmethyl)-3-(pyridin-3-yl)-1,2,3,4-tetrahydroisoquinoline-4-carboxylic acid;

1-oxo-2-(1-butyl)-3-(pyridin-3-yl)-1,2,3,4-tetrahydroisoquinoline-4-carboxylic acid; 1-oxo-2-isobutyl-3-(1-methyl-1H-pyrazol-4-yl)-7-fluoro-1,2,3,4-tetrahydroisoquinoline-4-carboxylic acid;

1-oxo-2-isobutyl-3-(1-methyl-1H-pyrazol-4-yl)-6-fluoro-1,2,3,4-tetrahydroisoquinoline-4-carboxylic acid;

1-oxo-2-isobutyl-3-(isothiazol-4-yl)-1,2,3,4-tetrahydroisoquinoline-4-carboxylic acid; 1-oxo-2-isobutyl-3-(pyrimidin-5-yl)-1,2,3,4-tetrahydroisoquinoline-4-carboxylic acid;

1-oxo-2-isobutyl-3-(5-cyanothiophen-2-yl)-6-fluoro-1,2,3,4-tetrahydroisoquinoline-4-carboxylic acid;

1-oxo-2-(2,2,2-trifluoroethyl)-3-(1-methyl-1H-pyrazol-4-yl)-7-fluoro-1,2,3,4-tetrahydroisoquinoline-4-carboxylic acid;

1-oxo-2-cyclopropylmethyl-3-(5-cyanothiophen-2-yl)-1,2,3,4-tetrahydroisoquinoline-4-carboxylic acid;

1-oxo-2-(1-butyl)-3-(5-cyanothiophen-2-yl)-1,2,3,4-tetrahydroisoquinoline-4-carboxylic acid; and 2-isobutyl-7-methoxy-1-oxo-3-(pyridin-3-yl)-1,2,3,4-tetrahydroisoquinoline-4-carboxylic acid.

D. Pharmaceutical Compositions

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and the nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as arginine, betaine, caffeine, choline, N,N'-dibenzylethylenediamine, diethylamine, 2-diethylaminoethanol, 2-dimethylamino ethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids" includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions, while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and the nature and severity of the conditions for which the active ingredient is being administered.

The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included, such as hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use, such as an aerosol, cream, ointment, lotion, dusting powder, mouthwash, gargle, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt% to about 10 wt% of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient.

Compositions containing a compound of the invention, and/or pharmaceutically acceptable salts thereof, can also be prepared in powder or liquid concentrate form.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

To prepare the pharmaceutical compositions of this invention, an effective amount of the particular compound, optionally in salt form, as the active ingredient is combined in intimate admixture with a pharmaceutically acceptable carrier or diluent, which carrier or diluent may take a wide variety of forms depending on the form of preparation desired for administration.

These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions, or solid carriers such as starches, sugars, kaolin, diluents, lubricants, binders, disintegrating agents and the like in the case of powders, pills, capsules and tablets. Because of the ease of administration, oral administration is preferred, and tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations.

In compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, or as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

In order to enhance the solubility and/or the stability of the disclosed compounds in pharmaceutical compositions, it can be advantageous to employ $\alpha$-, $\beta$- or $\gamma$-cyclodextrins or their derivatives, in particular hydroxyalkyl substituted cyclodextrins, e.g., 2-hydroxypropyl -$\beta$-cyclodextrin or sulfobutyl-$\beta$-cyclodextrin. Also co-solvents such as alcohols may improve the solubility and/or the stability of the compounds according to the invention in pharmaceutical compositions.

Further materials as well as processing techniques and the like are set out in The Science and Practice of Pharmacy (Remington: The Science & Practice of Pharmacy), $22^{nd}$ Edition, 2012, *Lloyd, Ed. Allen, Pharmaceutical Press* which is incorporated herein by reference.

The exact dosage and frequency of administration depends on the particular disclosed compound used, the particular condition being treated, the severity of the condition being treated, and the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and from 1 to 99.95% by weight, preferably from 30 to 99.9% by weight, more preferably from 50 to 99.9% by weight of a pharmaceutically acceptable carrier, all percentages being based on the total weight of the composition.

The amount of a disclosed compound that can be combined with a carrier material to produce a single dosage form will vary depending upon the disease treated, the mammalian species, and the particular mode of administration. However, as a general guide, suitable unit doses for the compounds of the present invention can, for example, preferably contain between 0.1 mg to about 1000 mg of the active compound. A preferred unit dose is between 1 mg to about 500 mg. A more preferred unit dose is between 1 mg to about 300 mg. An even more preferred unit dose is between 1 mg to about 100 mg. Such unit doses can be administered more than once a day, for example, 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and, in some cases, years. It will be understood, however, that the specific dose level for any particular patient will depend on a variety of factors, including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

As already mentioned, the invention relates to a pharmaceutical composition comprising a therapeutically effective amount of a compound according to the invention, and a pharmaceutically acceptable carrier. Additionally, the invention relates to a process for preparing such pharmaceutical composition, characterized in that a pharmaceutically acceptable carrier is intimately mixed with a therapeutically effective amount of a compound according to the invention.

As already mentioned, the invention also relates to a pharmaceutical composition comprising the compounds according to the invention and one or more other drugs in the treatment, prevention, control, amelioration, or reduction of risk of diseases or conditions for which disclosed compounds or the other drugs may have utility as well as to the use of such a composition for the manufacture of a medicament.

According to a particular aspect, pharmaceutical compositions according to the invention are provided, further comprising a co-agent useful in the treatment of malaria, such as substances useful in the treatment and/or prevention of malaria, e.g., a co-agent including, but not limited to, artemisinin or an artemisinin derivative (such as artemether or dihydroartemisinin), chloroquine, mefloquine, quinine, atovaquone/proguanil, doxycycline, hydroxychloroquine, pyronaridine, lumefantrine, pyrimethamine-sulfadoxine, quinacrine, chloroquine, primaquine, doxycycline, atovaquone, proguanil hydrochloride, piperaquine, ferroquine, tafenoquine, arterolane, Spiro[3H-indole-3,1'-[1H]pyrido[3,4-b]indol]-2(1H)-one (CAS Registry Number: 1193314-23-6), 5,7'-dichloro-6'-fluoro-2',3',4',9'-tetrahydro-3'-methyl-, (1'R, 3'S], Sulfur, [4-[[2-(1,1-difluoroethyl)-5-methyl[1,2,4]triazolo [1,5-a]pyrimidin-7-yl]amino]phenyl] pentafluoro-] (CAS Registry Number: 1282041-94-4), Morpholine, and 4-[2-(4-cis-dispiro[cyclohexane-1,3'-[1,2,4]trioxolane-5', 2''-tricyclo [3.3.1.13,7]decan]-4-ylphenoxy)ethyl]-] (CAS Registry Number: 1029939-86-3).

E. Methods of Using the Compounds and Compositions

The disclosed compounds have various utilities, and it is contemplated that the disclosed compounds of formulae (I) and (II) can be used to perform the disclosed methods. According to the invention, the compounds of the invention and pharmaceutical formulations thereof can be administered alone or in combination with a co-agent useful in the treatment of malaria, such as substances useful in the treatment and/or prevention of malaria, e.g., a co-agent including, but not limited to, artemisinin or an artemisinin derivative (such as artemether or dihydroartemisinin), chloroquine, mefloquine, quinine, atovaquone/proguanil, doxycycline, hydroxychloroquine, pyronaridine, lumefantrine, pyrimethamine-sulfadoxine, quinacrine, chloroquine, primaquine, doxycycline, atovaquone, proguanil hydrochloride, piperaquine, ferroquine, tafenoquine, arterolane, Spiro[3H-indole-3,1'-[1H]pyrido[3,4-b]indol]-2(1H)-one (CAS Registry Number: 1193314-23-6), 5,7'-dichloro-6'-fluoro-2',3',4', 9'-tetrahydro-3'-methyl-, (1'R,3'S)-], Sulfur, [4-[[2-(1,1-difluoroethyl)-5-methyl[1,2,4]triazolo [1,5-a]pyrimidin-7-yl]amino]phenyl] pentafluoro-] (CAS Registry Number: 1282041-94-4), Morpholine, and 4-[2-(4-cis-dispiro[cyclohexane-1,3'-[1,2,4]trioxolane-5',2''-tricyclo [3.3.1.13,7]decan]-4-ylphenoxy)ethyl]-] (CAS Registry Number: 1029939-86-3).

The invention encompasses the administration of compounds according to the invention or of a pharmaceutical formulation thereof, wherein the compounds of the invention or the pharmaceutical formulation thereof are administered to an individual prior to, simultaneously or sequentially with other therapeutic regimens or co-agents useful in the treatment of malaria (e.g. multiple drug regimens), in an effective amount. Compounds of the invention or the pharmaceutical formulations thereof that are administered simultaneously with said co-agents can be administered in the same or different composition(s) and by the same or different route(s) of administration.

1. Treatment Methods

The compounds disclosed herein are useful for treating, preventing, ameliorating, controlling or reducing the risk of malaria.

a. Methods for the Treatment of Malaria

In one aspect, the invention relates to a method for the treatment of malaria comprising the step of administering to a primate a therapeutically effective amount of at least one compound having a structure represented by a formula:

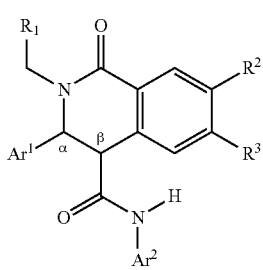

(II)

wherein $Ar^1$ is monocyclic heteroaryl selected from 2-thiopheneyl, 3-thiopheneyl, 5-cyano-2-thiopheneyl, 2-furanyl, 3-furanyl, imidazolyl, 4-isoxazolyl, 4-pyrazolyl, N-methyl-4-pyrazolyl, 5-thiazolyl, 5-isothiazolyl, 4-isothiazolyl, 2-pyridinyl, 3-pyridinyl, 4-pyridinyl, 5-pyrimidinyl, and 4-pyridazinyl; wherein $R^1$ is selected from hydrogen, methyl, ethyl, n-propyl, i-propyl, cyclopropyl, n-butyl, i-butyl, s-butyl, t-butyl, and cyclobutyl and, valence permitting, is substituted with 0-3 groups selected from fluoro, chloro, bromo, iodo, cyano, methoxyl, and ethoxyl; wherein $R^2$ and $R^3$ are independently selected from hydrogen, C1-C4 alkyl, cyano, fluoro, chloro, bromo, and iodo; wherein ring substituents at the carbon atoms denoted with labels α and β have a trans configuration; wherein $Ar^2$ has a structure represented by a formula:

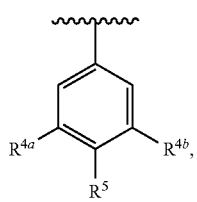

wherein $R^{4a}$ and $R^{4b}$ are independently selected from hydrogen, fluoro, chloro, bromo, iodo, cyano, C1-C4 alkyl, C1-C4 haloalkyl, C1-C4 polyhaloalkyl, C1-C4 alkoxyl, C1-C4 haloalkoxyl, and C1-C4 polyhaloalkoxyl; and wherein $R^5$ is selected from hydrogen, fluoro, chloro, bromo, iodo, cyano, C1-C4 alkyl, C1-C4 haloalkyl, C1-C4 polyhaloalkyl, C1-C4 alkoxyl, C1-C4 haloalkoxyl, and C1-C4 polyhaloalkoxyl, provided that if $Ar^1$ is unsubstituted thiopheneyl, then $R^1$ is not isopropyl, or a pharmaceutically acceptable salt, hydrate, solvate, or polymorph thereof, as well as tautomers, geometrical isomers, and optically active forms thereof, thereby treating malaria in the primate.

In a further aspect, the primate has been diagnosed with malaria prior to the administering step. In a further aspect, the method further comprises the step of identifying a primate in need of treatment of malaria. In a further aspect, the method further comprises administration of one or more of quinine, quinacrine, chloroquine, primaquine, mefloquine, doxycycline, atovaquone, and proguanil hydrochloride. In a further aspect, the method further comprises administration of one or more of artemisinin or an artemisinin derivative (such as artemether or dihydroartemisinin), chloroquine, mefloquine, quinine, atovaquone/proguanil, doxycycline, hydroxychloroquine, pyronaridine, lumefantrine, pyrimethamine-sulfadoxine, quinacrine, chloroquine, primaquine, doxycycline, atovaquone, proguanil hydrochloride, piperaquine, ferroquine, tafenoquine, arterolane, Spiro[3H-indole-3,1'-[1H]pyrido[3,4-b]indol]-2(1H)-one (CAS Registry Number: 1193314-23-6), 5,7'-dichloro-6'-fluoro-2',3',4',9'-tetrahydro-3'-methyl-, (1'R,3'S)-], Sulfur, [4-[[2-(1,1-difluoroethyl)-5-methyl[1,2,4]triazolo [1,5-a]pyrimidin-7-yl]amino]phenyl]pentafluoro-] (CAS Registry Number: 1282041-94-4), Morpholine, and 4-[2-(4-cis-dispiro[cyclohexane-1,3'-[1,2,4]trioxolane-5',2"-tricyclo [3.3.1.13,7]decan]-4-ylphenoxy)ethyl]-] (CAS Registry Number: 1029939-86-3).

b. Methods for the Prevention of Malaria

In one aspect, the invention relates to a method for the prevention of malaria comprising the step of administering to a primate at risk of contracting malaria a prophylactically effective amount of at least one compound of the invention.

In a further aspect, the prophylactically effective amount is a sub-therapeutically effective amount. In a further aspect, the primate is a human.

c. Methods for Inactivating Parasitic Infection

In one aspect, the invention relates to a method for inactivating parasitic infection in a cell, comprising the step of contacting the cell with an effective amount of at least one compound of the invention.

In a further aspect, inactivating is killing the parasite. In a further aspect, inactivating is preventing replication of the parasite. In a further aspect, inactivating is preventing transmission of the parasite.

In a further aspect, the parasite is a eukaryotic protist of the genus *Plasmodium*. In a further aspect, the parasite is Plasmodium falciparum. In a further aspect, the parasite is *Plasmodium vivax*, *Plasmodium ovale*, or *Plasmodium malariae*. In a further aspect, the parasite is *Plasmodium knowlesi*.

In a further aspect, the amount is a therapeutically effective amount. In a further aspect, the amount is a prophylactically effective amount.

In a further aspect, the cell is a primate cell. In a further aspect, the cell is a red blood cell. In a further aspect, the cell is a human cell. In a further aspect, the cell has been isolated from a primate prior to the contacting step. In a further aspect, contacting is via administration to a primate.

2. Manufacture of a Medicament

In one aspect, the invention relates to a method for the manufacture of a medicament for the treatment and/or prevention of malaria.

3. Use of Compounds

In one aspect, the invention relates to the use of a disclosed compound or a product of a disclosed method. In a further aspect, a use relates to the manufacture of a medicament for the treatment and/or prevention of malaria 4. Kits In one aspect, the invention relates to a kit comprising a disclosed compound or a product of a disclosed method and one or more of: at least one agent known to prevent malaria; at least one agent known to treat malaria; or instructions for treating malaria. In a further aspect, the at least one compound or the at least one product and the at least one agent are co-formulated. In a further aspect, the at least one compound or the at least one product and the at least one agent are co-packaged. In a further aspect, the kit further comprises one or more of quinine, quinacrine, chloroquine, primaquine, mefloquine, doxycycline, atovaquone, and proguanil hydrochloride.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using, and/or the disclosed compositions.

5. Non-Medical Uses

Also provided are the uses of the disclosed compounds and products as pharmacological tools in the development and standardization of in vitro and in vivo test systems for the evaluation of the effects of drug candidates in laboratory animals such as cats, dogs, rabbits, monkeys, rats and mice, as part of the search for new therapeutic agents for the treatment of malaria.

F. Examples

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein. As indicated, some of the Examples were obtained as racemic mixtures of one or more enantiomers or diastereomers. The compounds may be separated by one skilled in the art to isolate individual enantiomers. Separation can be carried out by the coupling of a racemic mixture of compounds to an enantiomerically pure compound to form a diastereomeric mixture, followed by separation of the individual diastereomers by standard methods, such as fractional crystallization or chromatography. A racemic or diastereomeric mixture of the compounds can also be separated directly by chromatographic methods using chiral stationary phases.

1. Preparation of Aldimines 1a:

To a solution of the aldehyde (1 equiv.) and amine (1 equiv.) in methanol was added a catalytic amount of glacial acetic acid (a few drops) and the contents were stirred at 25 ° C. as outlined in reaction Scheme 1. After 4 h, the methanol was removed under reduced pressure and the crude aldimine 1a was used in the next step without further purification.

2. General Procedure for Acids 2a:

A solution of aldimine 1a (1 equiv.) and homophthalic anhydride (0.45 g, 2.80 mmol, 1 equiv.) in acetic acid (10 mL) was heated at 120 ° C. for 16 h and then concentrated under reduced pressure as outlined in reaction Scheme 1. The residue was solidified in EtOAc to afford the acid 2a. In most cases, the acid was used directly in next step although some acids required further purification. The yields were generally 55 to 65%.

3. General Procedure for Amide IIj:

To a solution of 2a (1 equiv.) and amine (1.2 equiv.) in dichloromethane was added triethylamine (2 equiv.) as outlined in reaction Scheme 1. The reaction mixture was cooled to 0° C. and propylphosphonic acid anhydride (T3P) (2.5 equiv.) was added. The reaction mixture was then warmed to room temperature and stirred for 16 h. After the completion of the reaction, the reaction mixture was diluted with dichloromethane and washed successively with saturated sodium bicarbonate solution, water, and brine and dried over anhydrous $Na_2SO_4$. The solvent was then removed under reduced pressure to yield the crude product, which was purified over silica gel using 30%-60% ethyl acetate in pet-ether as eluant to yield the pure IIj in 35 to 40% yields.

Data for selected disclosed compounds tested as a racemate mixture (unless indicated) are summarized in Table III:

TABLE III

| Example | Structure (racemate unless indicated) | Chemical name | $3D7\_EC_{50}$ (nM) |
|---|---|---|---|
| 1 | | N-(3-cyano-4-fluorophenyl)-2-isobutyl-1-oxo-3-(1H-pyrazol-4-yl)-1,2,3,4-tetrahydroisoquinoline-4-carboxamide | 11 |

TABLE III-continued

| Example | Structure (racemate unless indicated) | Chemical name | 3D7_EC$_{50}$ (nM) |
|---|---|---|---|
| 2 | | N-(3-cyano-4-fluorophenyl)-1-oxo-3-(1H-pyrazol-4-yl)-2-(2,2,2-trifluoroethyl)-1,2,3,4-tetrahydroisoquinoline-4-carboxamide | Racemate: 41 d-isomer: 19 |
| 3 | | N-(3-cyano-4-fluorophenyl)-2-isobutyl-3-(1-methyl-1H-pyrazol-4-yl)-1-oxo-1,2,3,4-tetrahydroisoquinoline-4-carboxamide | 12 |
| 4 | | N-(3-cyano-4-fluorophenyl)-3-(1-methyl-1H-pyrazol-4-yl)-1-oxo-2-(2,2,2-trifluoroethyl)-1,2,3,4-tetrahydroisoquinoline-4-carboxamide | 24 |

TABLE III-continued

| Example | Structure (racemate unless indicated) | Chemical name | 3D7_EC$_{50}$ (nM) |
|---|---|---|---|
| 5 | | N-(3-cyano-4-fluorophenyl)-2-isobutyl-1-oxo-3-(pyridin-3-yl)-1,2,3,4-tetrahydroisoquinoline-4-carboxamide | Racemate: 25<br>d-isomer: 15 |
| 6 | | N-(3-cyano-4-fluorophenyl)-1-oxo-3-(pyridin-3-yl)-2-(2,2,2-trifluoroethyl)-1,2,3,4-tetrahydroisoquinoline-4-carboxamide | Racemate: 54<br>d-isomer: 17 |
| 7 | | N-(3-chloro-5-cyanophenyl)-2-isobutyl-1-oxo-3-(1H-pyrazol-4-yl)-1,2,3,4-tetrahydroisoquinoline-4-carboxamide | 3 |
| 8 | | N-(3-chloro-5-cyanophenyl)-1-oxo-3-(1H-pyrazol-4-yl)-2-(2,2,2-trifluoroethyl)-1,2,3,4-tetrahydroisoquinoline-4-carboxamide | 26 |

TABLE III-continued

| Example | Structure (racemate unless indicated) | Chemical name | 3D7_EC$_{50}$ (nM) |
|---|---|---|---|
| 9 | | N-(3-chloro-5-cyanophenyl)-2-isobutyl-3-(1-methyl-1H-pyrazol-4-yl)-1-oxo-1,2,3,4-tetrahydroisoquinoline-4-carboxamide | 8 |
| 10 | | N-(3-chloro-5-cyanophenyl)-3-(1-methyl-1H-pyrazol-4-yl)-1-oxo-2-(2,2,2-trifluoroethyl)-1,2,3,4-tetrahydroisoquinoline-4-carboxamide | 6 |
| 11 | | N-(3-chloro-5-cyanophenyl)-2-isobutyl-1-oxo-3-(pyridin-3-yl)-1,2,3,4-tetrahydroisoquinoline-4-carboxamide | 20 |
| 12 | | N-(3-chloro-5-cyanophenyl)-1-oxo-3-(pyridin-3-yl)-2-(2,2,2-trifluoroethyl)-1,2,3,4-tetrahydroisoquinoline-4-carboxamide | 36 |

TABLE III-continued

| Example | Structure (racemate unless indicated) | Chemical name | 3D7_EC$_{50}$ (nM) |
|---|---|---|---|
| 13 | 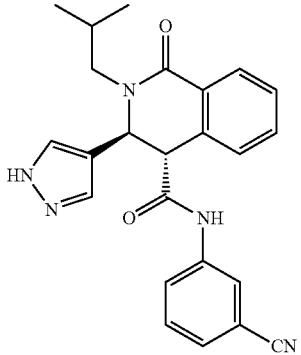 [SMILES: CC(C)CN1C(=O)c2ccccc2[C@H](C(=O)Nc2cccc(C#N)c2)[C@H]1c1cn[nH]c1] | N-(3-cyanophenyl)-2-isobutyl-1-oxo-3-(1H-pyrazol-4-yl)-1,2,3,4-tetrahydroisoquinoline-4-carboxamide | 7 |
| 14 | 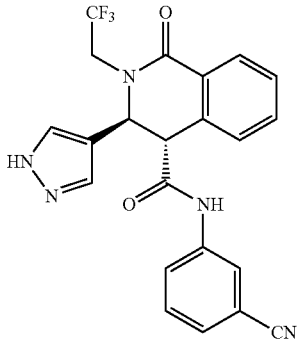 [SMILES: N#Cc1cccc(NC(=O)[C@H]2c3ccccc3C(=O)N(CC(F)(F)F)[C@@H]2c2cn[nH]c2)c1] | N-(3-cyanophenyl)-1-oxo-3-(1H-pyrazol-4-yl)-2-(2,2,2-trifluoroethyl)-1,2,3,4-tetrahydroisoquinoline-4-carboxamide | 30 |
| 15 | 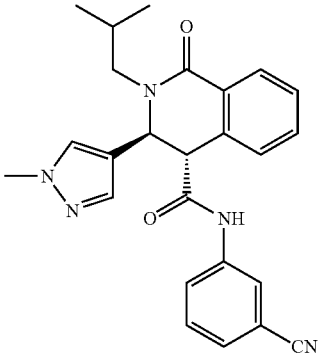 [SMILES: CC(C)CN1C(=O)c2ccccc2[C@H](C(=O)Nc2cccc(C#N)c2)[C@H]1c1cnn(C)c1] | N-(3-cyanophenyl)-2-isobutyl-3-(1-methyl-1H-pyrazol-4-yl)-1-oxo-1,2,3,4-tetrahydroisoquinoline-4-carboxamide | 36 |
| 16 | 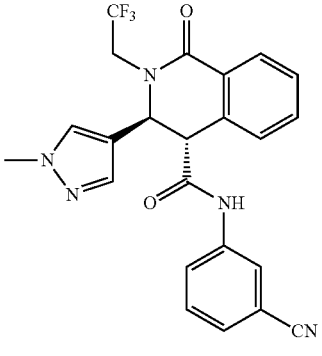 [SMILES: Cn1cc([C@@H]2[C@@H](C(=O)Nc3cccc(C#N)c3)c3ccccc3C(=O)N2CC(F)(F)F)cn1] | N-(3-cyanophenyl)-3-(1-methyl-1H-pyrazol-4-yl)-1-oxo-2-(2,2,2-trifluoroethyl)-1,2,3,4-tetrahydroisoquinoline-4-carboxamide | 22 |

TABLE III-continued

| Example | Structure (racemate unless indicated) | Chemical name | 3D7_EC$_{50}$ (nM) |
|---|---|---|---|
| 17 | | N-(3-cyanophenyl)-2-isobutyl-1-oxo-3-(pyridin-3-yl)-1,2,3,4-tetrahydroisoquinoline-4-carboxamide | 58 |
| 18 | | N-(3-cyanophenyl)-1-oxo-3-(pyridin-3-yl)-2-(2,2,2-trifluoroethyl)-1,2,3,4-tetrahydroisoquinoline-4-carboxamide | 24 |
| 19 | | N-(3-cyano-5-fluorophenyl)-2-isobutyl-1-oxo-3-(1H-pyrazol-4-yl)-1,2,3,4-tetrahydroisoquinoline-4-carboxamide | 4 |
| 20 | | N-(3-cyano-5-fluorophenyl)-1-oxo-3-(1H-pyrazol-4-yl)-2-(2,2,2-trifluoroethyl)-1,2,3,4-tetrahydroisoquinoline-4-carboxamide | Racemate: 9 d-isomer: 8 |

TABLE III-continued

| Example | Structure (racemate unless indicated) | Chemical name | 3D7_EC$_{50}$ (nM) |
|---|---|---|---|
| 21 | | N-(3-cyano-5-fluorophenyl)-2-isobutyl-3-(1-methyl-1H-pyrazol-4-yl)-1-oxo-1,2,3,4-tetrahydroisoquinoline-4-carboxamide | 21 |
| 22 | | N-(3-cyano-5-fluorophenyl)-3-(1-methyl-1H-pyrazol-4-yl)-1-oxo-2-(2,2,2-trifluoroethyl)-1,2,3,4-tetrahydroisoquinoline-4-carboxamide | 9 |
| 23 | | N-(3-cyano-5-fluorophenyl)-2-isobutyl-1-oxo-3-(pyridin-3-yl)-1,2,3,4-tetrahydroisoquinoline-4-carboxamide | 20 |
| 24 | | N-(3-cyano-5-fluorophenyl)-1-oxo-3-(pyridin-3-yl)-2-(2,2,2-trifluoroethyl)-1,2,3,4-tetrahydroisoquinoline-4-carboxamide | 38 |

TABLE III-continued

| Example | Structure (racemate unless indicated) | Chemical name | 3D7_EC$_{50}$ (nM) |
|---|---|---|---|
| 25 | 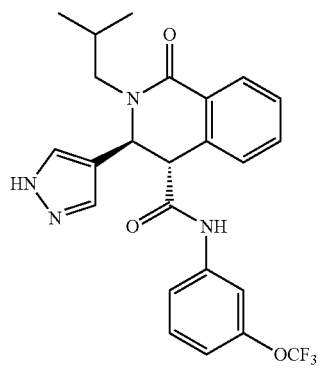 [SMILES: CC(C)CN1C(=O)c2ccccc2[C@H](C(=O)Nc2cccc(OC(F)(F)F)c2)[C@H]1c1cn[nH]c1] | 2-isobutyl-1-oxo-3-(1H-pyrazol-4-yl)-N-(3-(trifluoromethoxy)phenyl)-1,2,3,4-tetrahydroisoquinoline-4-carboxamide | 11 |
| 26 | 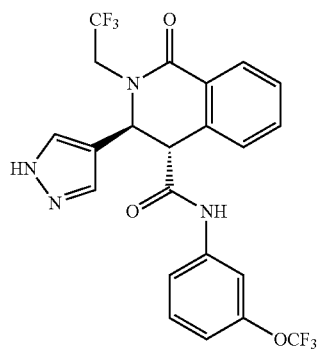 [SMILES: O=C(Nc1cccc(OC(F)(F)F)c1)[C@H]1c2ccccc2C(=O)N(CC(F)(F)F)[C@@H]1c1cn[nH]c1] | 1-oxo-3-(1H-pyrazol-4-yl)-2-(2,2,2-trifluoroethyl)-N-(3-(trifluoromethoxy)phenyl)-1,2,3,4-tetrahydroisoquinoline-4-carboxamide | 19 |
| 27 | 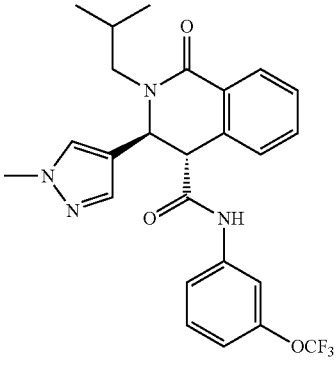 [SMILES: CC(C)CN1C(=O)c2ccccc2[C@H](C(=O)Nc2cccc(OC(F)(F)F)c2)[C@H]1c1cnn(C)c1] | 2-isobutyl-3-(1-methyl-1H-pyrazol-4-yl)-1-oxo-N-(3-(trifluoromethoxy)phenyl)-1,2,3,4-tetrahydroisoquinoline-4-carboxamide | 8 |
| 29 | 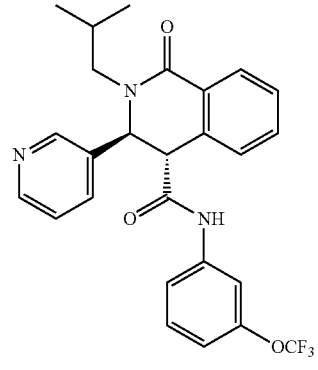 [SMILES: CC(C)CN1C(=O)c2ccccc2[C@H](C(=O)Nc2cccc(OC(F)(F)F)c2)[C@H]1c1cccnc1] | 2-isobutyl-1-oxo-3-(pyridin-3-yl)-N-(3-(trifluoromethoxy)phenyl)-1,2,3,4-tetrahydroisoquinoline-4-carboxamide | 25 |

TABLE III-continued

| Example | Structure (racemate unless indicated) | Chemical name | 3D7_EC$_{50}$ (nM) |
|---|---|---|---|
| 30 | | 1-oxo-3-(pyridin-3-yl)-2-(2,2,2-trifluoroethyl)-N-(3-(trifluoromethoxy)phenyl)-1,2,3,4-tetrahydroisoquinoline-4-carboxamide | 25 |
| 31 | | N-(4-fluoro-3-(trifluoromethoxy)phenyl)-2-isobutyl-1-oxo-3-(1H-pyrazol-4-yl)-1,2,3,4-tetrahydroisoquinoline-4-carboxamide | 13 |
| 32 | | N-(4-fluoro-3-(trifluoromethoxy)phenyl)-1-oxo-3-(1H-pyrazol-4-yl)-2-(2,2,2-trifluoroethyl)-1,2,3,4-tetrahydroisoquinoline-4-carboxamide | 22 |
| 33 | | N-(4-fluoro-3-(trifluoromethoxy)phenyl)-2-isobutyl-3-(1-methyl-1H-pyrazol-4-yl)-1-oxo-1,2,3,4-tetrahydroisoquinoline-4-carboxamide | 17 |

TABLE III-continued

| Example | Structure (racemate unless indicated) | Chemical name | 3D7_EC$_{50}$ (nM) |
|---|---|---|---|
| 35 | | N-(4-fluoro-3-(trifluoromethoxy)phenyl)-2-isobutyl-1-oxo-3-(pyridin-3-yl)-1,2,3,4-tetrahydroisoquinoline-4-carboxamide | 63 |
| 36 | | N-(4-fluoro-3-(trifluoromethoxy)phenyl)-1-oxo-3-(pyridin-3-yl)-2-(2,2,2-trifluoroethyl)-1,2,3,4-tetrahydroisoquinoline-4-carboxamide | 89 |
| 38 | | N-(3-fluoro-5-(trifluoromethoxy)phenyl)-1-oxo-3-(1H-pyrazol-4-yl)-2-(2,2,2-trifluoroethyl)-1,2,3,4-tetrahydroisoquinoline-4-carboxamide | 61 |
| 42 | | N-(3-fluoro-5-(trifluoromethoxy)phenyl)-1-oxo-3-(pyridin-3-yl)-2-(2,2,2-trifluoroethyl)-1,2,3,4-tetrahydroisoquinoline-4-carboxamide | 144 |

TABLE III-continued

| Example | Structure (racemate unless indicated) | Chemical name | 3D7_EC$_{50}$ (nM) |
|---|---|---|---|
| 43 | | N-(3-cyano-4-fluorophenyl)-2-(cyclopropylmethyl)-1-oxo-3-(pyridin-3-yl)-1,2,3,4-tetrahydroisoquinoline-4-carboxamide | 351 |
| 44 | | 2-butyl-N-(3-cyano-4-fluorophenyl)-1-oxo-3-(pyridin-3-yl)-1,2,3,4-tetrahydroisoquinoline-4-carboxamide | 651 |
| 45 | | N-(3-cyano-4-fluorophenyl)-7-fluoro-2-isobutyl-3-(1-methyl-1H-pyrazol-4-yl)-1-oxo-1,2,3,4-tetrahydroisoquinoline-4-carboxamide | 20 |

TABLE III-continued

| Example | Structure (racemate unless indicated) | Chemical name | 3D7_EC$_{50}$ (nM) |
|---|---|---|---|
| 46 | | N-(3-chloro-5-cyanophenyl)-7-fluoro-2-isobutyl-3-(1-methyl-1H-pyrazol-4-yl)-1-oxo-1,2,3,4-tetrahydroisoquinoline-4-carboxamide | 3 |
| 47 | | N-(3-cyanophenyl)-6-fluoro-2-isobutyl-3-(1-methyl-1H-pyrazol-4-yl)-1-oxo-1,2,3,4-tetrahydroisoquinoline-4-carboxamide | 7 |
| 48 | | N-(3-cyano-5-fluorophenyl)-6-fluoro-2-isobutyl-3-(1-methyl-1H-pyrazol-4-yl)-1-oxo-1,2,3,4-tetrahydroisoquinoline-4-carboxamide | 19 |
| 49 | | N-(3-cyano-4-fluorophenyl)-2-isobutyl-3-(isothiazol-4-yl)-1-oxo-1,2,3,4-tetrahydroisoquinoline-4-carboxamide | 52 |

TABLE III-continued

| Example | Structure (racemate unless indicated) | Chemical name | 3D7_EC$_{50}$ (nM) |
|---|---|---|---|
| 50 | | N-(3-cyano-4-fluorophenyl)-2-isobutyl-1-oxo-3-(pyrimidin-5-yl)-1,2,3,4-tetrahydroisoquinoline-4-carboxamide | 486 |
| 51 | | N-(3-cyano-5-fluorophenyl)-3-(5-cyanothiophen-2-yl)-6-fluoro-2-isobutyl-1-oxo-1,2,3,4-tetrahydroisoquinoline-4-carboxamide | 5 |
| 53 | | N-(3-cyano-4-fluorophenyl)-2-isobutyl-7-methoxy-1-oxo-3-(pyridin-3-yl)-1,2,3,4-tetrahydroisoquinoline-4-carboxamide | 150 |

TABLE III-continued

| Example | Structure (racemate unless indicated) | Chemical name | 3D7_EC$_{50}$ (nM) |
|---|---|---|---|
| 54 | | N-(3-cyano-4-fluorophenyl)-3-(5-cyanothiophen-2-yl)-2-(cyclopropylmethyl)-1-oxo-1,2,3,4-tetrahydroisoquinoline-4-carboxamide | 11 |
| 59 | | N-(3-cyano-4-fluorophenyl)-1-oxo-3-(1H-pyrazol-4-yl-6,7-difluoro-2-(2,2,2-trifluoroethyl)-1,2,3,4-tetrahydroisoquinoline-4-carboxamide | 7 |

4. Parasite and Cell-Based Assay Methods a. *P. Falciparum* Drug Susceptibility Assay (St. Jude, Pf3D7a)

Parasites were grown as previously described in Mallari, J. P., Guiguemde, W. A., and Guy, R. K., Antimalarial activity of thiosemicarbazones and purine derived nitriles, *Bioorg Med Chem Lett* 19 (13), 3546 (2009). For EC$_{50}$ determinations, 20 µl of RPMI 1640 (L-glutamine and HEPES, Invitrogen) with a final 5 µg/ml gentamicin were dispensed per well with a liquid dispenser (Matrix Wellmate, Thermo Scientific) in an assay plate (384-well black polystyrene microplate, clear bottom, tissue culture treated, Corning). DMSO inhibitor stock solutions were pin-transferred (V&P Scientific) into the assay plate and background fluorescence was measured in both relevant channels (485 nm /535 nm, 612 nm /665 nm) in an Envision plate reader (PerkinElmer). Then 20 µl of a synchronized culture suspension (1% rings, 10% hematocrit) were added per well, thus making a final hematocrit and parasitemia of 5% and 1% respectively. Assay plates were incubated for 72 h and parasitemia was determined based on a modified protocol. (Smilkstein, M. et al., Simple and inexpensive fluorescence-based technique for high-throughput antimalarial drug screening. *Antimicrob Agents Chemother* 48 (5), 1803 (2004)). Briefly, 5 µl of mixed DNA dye solution in RPMI (5X SYBR Green I, 1 µM YOYO-3, 1% v/v Triton X-100, 1 mg/ml saponin) were added per well, assay plates were shaken for 30 s at 2000 rpm, incubated in the dark for 4 h, then read as previously described.

b. *P. Falciparum* Drug Susceptibility Assay (Avery Lab, Pf3D7b)

Compounds were transferred into 384 well poly-D-lysine coated wells (PerkinElmer) using a 384 well mini track dispenser. 25 µl of assay media was added per well followed by 20 µl of 2 or 3% synchronized ring stage parasite in 0.75% hematocrit (3D7 or Dd2). The final assay parameters were 50 µl total volume, 0.3% final hematocrit and DMSO concentration of 0.4%. The plates were incubated for 72 h in a humidified atmosphere at 37° C., 5% O$_2$ and 5% CO$_2$. After incubation the plates were brought to room temperature and 30 µl of PBS added to all wells using a Biomek FX (Beckman Instruments). 60 µl of supernatant was then aspirated from the wells and 30 µl of DAPI staining buffer (4', 6-diamidino-2-phenylindole, (Invitrogen) in PBS containing 0.001% saponin and 0.01% Triton X-100) added. Plates were then incubated at RT in the dark for at least 5 h before imaging on the OPERA™ HTS confocal imaging system (PerkinElmer).

The digital images obtained were then analyzed using the PerkinElmer Acapella spot detection software where spots that fulfill the criteria established for a stained parasite are determined and counted. The % inhibition of parasite replication was calculated using DMSO and 2 µM artemisinin control data.

c. *P. Falciparum* Drug Susceptibility Assay (Derisi Lab, Pf3D7c)

Compounds were transferred using a Biomek FX robotic liquid handling device (Beckman Instruments) and incubated in presence of 2% hematocrit and 0.8% parasite in a total assay volume of 200 µl for 72 h in a humidified atmosphere at 37° C., 5% $O_2$ and 5% $CO_2$, in 96-well round bottom plates (Fisher). After incubation, 170 µl supernatant was discarded and cells were washed with 150 µl 1X PBS. 15 µl re-suspended cells were transferred to 384-well flat bottom non-sterile plates (Corning) already containing 15 µl of the SYBR Green lysis buffer (2X SYBR Green, 20 mM Tris base pH 7.5, 20 mM EDTA, 0.008% w/v saponin, 0.08% w/v Triton X-100). Plates were incubated for 15 min and then read on an LJL Biosystems Analyst AD 96-384 spectrophotometer.

d. Mammalian Cell Drug Susceptibility Assay

Raji, HEK293, Hep G2 and BJ cell lines were purchased from the American Type Culture Collection and were cultured according to recommendations. Exponentially growing cells respectively 1200, 400, 400, 1000 were plated per well (25 µl) in white polystyrene flat bottom sterile 384-well tissue culture treated plates (Corning), and incubated overnight at 37° C. in a humidified 5% $CO_2$ incubator. DMSO inhibitor stock solutions were pin-transferred (V&P Scientific) the following day. Plates were placed back in the incubator for 72 h incubation and equilibrated at room temperature for 20 min before addition of 25 µl Cell Titer Glo (Promega) to each well. Plates were shaken on an orbital shaker for 2 min at 500 rpm. Luminescence was read after 15 min on an Envision plate reader (PerkinElmer).

e. *Trypanosoma Brucei* Drug Susceptibility Assay

Culture adapted T brucei brucei were grown at 37° C., 5% $CO_2$ in HMI-9 medium (HyClone) supplemented with penicillin/streptomycin (50 µg/ml, Invitrogen), 10% heat inactivated FBS (Omega Scientific) and 10% Serum Plus (JHR Biosciences) to a density of $1 \times 10^6$ cells/mL, then diluted to $1 \times 10^4$ cells/mL. 100 µL of the diluted culture was added to each well of a white polycarbonate flat bottom sterile 96-well tissue culture treated plate (Greiner), and 1 µl of inhibitor in DMSO was added by pin-transfer using 200 nL slotted hydrophobic coated pins (V&P Scientific). Plates were incubated for 48 h at 37° C., 5% $CO_2$, then equilibrated at room temperature for 30 min before addition of 50 µl Cell Titer Glo (Promega) to each well. Plates were shaken on an orbital shaker for 2 min at 500 rpm. Luminescence was read after 8 min on an Envision plate reader (PerkinElmer).

f. *Toxoplasma Gondii* Drug Susceptibility Assay 10,000 U-2OS human host cells/well were grown for 24 h in 384-well plates, followed by introduction of test compound and 5000 freshly harvested RH strain *T gondii* parasites expressing luciferase in a final volume of 40 µl. (Matrajt, M. et al., Amino-terminal control of transgenic protein expression levels in *Toxoplasma gondii. Mol Biochem Parasitol* 120 (2), 285 (2002).) 44 h post-infection, DMNPE-caged luciferin (Sigma-Aldrich, St. Louis, Mo.) was added to each well to a final concentration of 10 µM, and 4 h later luminescence was read using an Analyst HT (Molecular Devices, Sunnyvale, Calif.).

g. *Leishmania Major* Promastigote Drug Susceptibility Assay

*Leishmania* major promastigotes were harvested in exponential growth phase (~2.0-3.0 X $10^7$ parasites/ml) and were seeded (5,000 parasites/22 µl) into each well of a 384 well microtiter plate using a MAPC2 bulk dispenser (Titertek, Huntsville, Ala.). Test and control chemicals (3 µl) were initially assayed at a single concentration (10 µM) and were added to individual microtiter plate wells using a Velocity 11 V-prep (Menlo Park, Calif.) liquid handling system, equipped with a 384-well dispensing head, followed by centrifugation at 50 g for 1 min. Negative (vehicle) controls contained 1% DMSO and positive controls contained 10% DMSO (final well concentrations). Assay plates were incubated for 44 h at 28° C. in the presence of 5% $CO_2$. 5 µl of Alamar Blue reagent were added to each assay plate well and incubated for 4 h at 28° C. with 5% $CO_2$. Data were captured (excitation $A_{560}$; emission $A_{590}$) on a Molecular Devices SpectraMax M5 (Sunnyvale, Calif.). Individual assay plate Z-primes (for primary screening activities) were calculated from the vehicle and positive controls and data from plates were used only if calculated Z-prime was >0.5. Primary actives were defined as chemicals displaying ≥50% inhibition of signal readout at 10 µM. For subsequent $EC_{50}$ determinations, *L. major* promastigotes were treated with a 20 point concentration range of compound from 0 to 25 µM for 44 h at 28° C. in the presence of 5% $CO_2$. 5 µl Alamar blue was added to each well, plates were incubated for 4 h at 28° C. with 5% $CO_2$, and data were captured as described above.

5. Enzymatic and Protein Assays a. Heme Crystallization Assay

Drugs were assayed in 100 µl of sodium acetate pH 4.8 containing 50 µM mono oleoyl-glycerol (Sigma) and 50 µM bovine hemin chloride (Sigma). Plates were next shaken for 5 min on a bench top plate rocker and incubated at 37° C. for 4-6 h. Plates were read in an HTS 7000 Plus 96-well plate reader (PerkinElmer) after successive additions of 100 µl of a 2% sodium dodecyl sulfate (SDS), 200 mM sodium bicarbonate solution and then 20 µl of 1 M NaOH. The $OD_{405}$ value of each measurement was converted to nmoles of soluble heme using the formula: nmoles of heme crystal=$OD_{405} \times 20.338 - 1.6369/5$. The nmoles of heme crystal formed in the presence of the drug were then divided by the number of nmoles of heme crystal formed in the 3 averaged vehicle control wells to determine a relative % inhibition for each drug. Each drug was performed in triplicate with experiments repeated at least twice.

b. PfDHOD Inhibition Assay

Compounds were initially assayed in 384-well plate format using a Biomek FX robotic liquid handling device (Beckman Instruments). The cross-validated set was screened for *P. falciparum* dihydroorotate dehydrogenase (PfDHODH) inhibitory activity at 0.1, 1.0 and 10 µM compound concentrations. Assay buffer solution (0.048 ml) (100 mM HEPES pH 8.0, 150 mM NaCl, 10% Glycerol, 0.05% Triton X-100, 20 µM $CoQ_0$, 200 µM L-dihydroorotate, 120 µM 2,6-dichloroindophenol) was transferred to each well, followed by addition of the stock solution (0.5 µl of 100X DMSO stock) for each compound. The assay was started by the addition of a 25X (2 µl) stock solution of enzyme (50 nM final in assay plate). The assay was allowed to progress at room temperature for 20 min, then 10% sodium dodecyl sulfate (5 µl) was added to stop the reaction. The plate was spun at 3000 rpm at room temperature for 1 min and the absorbance in each well was measured at 595 nm using an Envision plate reader (PerkinElmer). Hits were re-assayed to determine the $EC_{50}$ using a previously described protocol. (Phillips et al., Triazolopyrimidine-based dihydroorotate dehydrogenase inhibitors with potent and selective activity against the malaria parasite *Plasmodium falciparum. J. Med. Chem.* 51 (12), 3649 (2008)). This assay was performed in a Beckman DU650 spectrophotometer using the same buffers and reagents (final volume 0.5 ml) described for the plate assay except that the enzyme concentration was 10 nM, the triton concentration was increased to 0.1%, and a rate assay was used in place of the endpoint assay.

c. *Falcipain* (PfFP-2) Inhibition Assay $EC_{50}$s against falcipain-2 were determined as described earlier. (Shenai, B. R. et al., Structure-activity relationships for inhibition of cysteine protease activity and development of *Plasmodium falciparum* by peptidyl vinyl sulfones. *Antimicrob Agents Chemother* 47 (1), 154 (2003).) Briefly, equal amounts (1 nM) of recombinant PfFP-2 were incubated with different concentrations of compounds (in DMSO) in 100 mM sodium acetate (pH 5.5), 10 mM dithiothreitol for 30 min at room temperature before addition of the substrate benzoxycarbonyl-Leu-Arg-7-amino-4-methyl-coumarin (final concentration, 25 μM). Fluorescence was continuously monitored for 30 min at room temperature in a Labsystems Fluoroskan II spectrofluorometer. $EC_{50}$s were determined from plots of activity over enzyme concentration with GraphPad Prism software.

d. PfDHFR Inhibition Assay

*P. falciparum* dihydrofolate reductase (PfDHFR) of the 3D7 sequence was prepared in accordance to previously reported methods. (Hekmat-Nejad, M. and Rathod, P. K., *Plasmodium falciparum*: kinetic interactions of WR99210 with pyrimethamine-sensitive and pyrimethamine-resistant dihydrofolate reductase. Exp. Parasitol. 87 (3), 222 (1997); Sirawaraporn, W. et al., The dihydrofolate reductase domain of Plasmodium falciparum thymidylate synthase-dihydrofolate reductase. Gene synthesis, expression, and antifolate -resistant mutants. *J. Biol. Chem.* 268 (29), 21637 (1993)). DHFR inhibition was quantified using a previously reported assay with modifications. (Mui, E. J. et al., Novel triazine JPC -2067-B inhibits Toxoplasma gondii in vitro and in vivo. PLoS Negl Trop Dis 2 (3), e190 (2008).) The standard enzyme assay contained potassium phosphate buffer pH 7.0 (20 mM), EDTA (0.1 mM), glycerol (10% v/v), DTT (10 mM), NADPH (0.1 mM), dihydrofolic acid (0.1 mM), and sufficient enzyme to produce a change in $OD_{340}$ that is linear for about 10 min (approximately 0.02-0.05/min). All assays were run in Corning 3635 plates at 25° C. on a BioTek Synergy 4 with Gen5 software. The $OD_{340}$ was recorded at 35 second intervals for 10 min and the points between 1-7 min were used to determine velocity. The inhibitor solutions were made from 1 mM stock solutions in DMSO. Initial screens were performed at 500 and 5,000 nM with 3 replicates. $IC_{50}$s were determined with 4 replicates for each concentration. Prism 5.03 was used to generate curves from 11 different concentrations of inhibitor using a nonlinear fit method.

e. Preparation of Mitochondrial Fragments

*P. yoelii* parasites were obtained from outbred female CF-1 as described by Srivastava et al. (Srivastava, I. K., Rottenberg, H., and Vaidya, A. B., Atovaquone, a broad spectrum antiparasitic drug, collapses mitochondrial membrane potential in a malarial parasite. *J. Biol. Chem.,* 272 (7), 3961 (1997).)

Mitochondrial fragments were prepared by a procedure modified from Krungkrai et al. (Krungkrai, J., Krungkrai, S. R., Suraveratum, N., and Prapunwattana, P., Mitochondrial ubiquinol-cytochrome c reductase and cytochrome c oxidase: chemotherapeutic targets in malarial parasites. *Biochem Mol Biol Int* 42 (5), 1007 (1997); Krungkrai, J., The multiple roles of the mitochondrion of the malarial parasite. *Parasitology* 129 (Pt 5), 511 (2004).) Infected red blood cells were suspended in 125 ml of RPMI 1640 medium containing 0.075% saponin and incubated for 20 min at 37° C. After incubation the parasites were harvested by centrifugation at 8,000×g for 10 min. Intact parasites were washed in phosphate buffered saline (PBS) containing 1 mM PMSF four times and centrifuged at 8000×g for 10 min. The parasites were disrupted by resuspending the pellet in lysis buffer containing 75 mM sucrose, 225 mM mannitol, 5 mM $MgCl_2$, 5 mM $KH_2PO_4$, 1 mM EDTA, 1 mM PMSF, and 5 mM HEPES, at pH 7.4. The cells were then homogenized in a cooled glass dounce homogenizer. Cell debris was removed by centrifugation at 800×g for 5 min. Mitochondrial particles were then harvested at 20,000×g for 30 min. The pellet was resuspended in lysis buffer, and mixed to a final concentration of 30% glycerol. Aliquots of mitochondrial particles were frozen at –80° C. until needed.

f. Mitochondrial Electron Transport Studies Using *Falciparum* D10

A previously reported method (Painter, H. J., Morrisey, J. M., Mather, M. W., and Vaidya, A. B., Specific role of mitochondrial electron transport in blood-stage *Plasmodium falciparum*. Nature 446 (7131), 88 (2007)) was used to investigate whether compounds inhibit mitochondrial electron transport—the mechanism by which the known antimalarial chemotherapeutic atovaquone functions. The primary function of electron transport in erythrocytic stages of *P. falciparum* appears to be regeneration of ubiquinone, a co-factor for dihydroorotate dehydrogenase (DHOD), which is an important enzyme involved in pyrimidine biosynthesis. Antimalarial activity was measured in *P. falciparum* D10 and its transgenic strain D10_yDHOD (D10 transfected with yeast DHOD). The D10_yDHOD strain yields a phenotype whereby the pyrimidine biosynthetic pathway is independent of mitochondrial electron transport. Compounds with reduced activity in D10_yDHOD are likely to be targeting either mitochondrial electron transport or the parasite DHOD. The DHFR inhibitor Proguanil synergies with electron transport inhibitors at 1 μM by collapsing mitochondrial membrane potential; therefore, antimalarial activity will be restored in D10_yDHOD for compounds targeting electron transport. Subsequent enzyme inhibition assays were used to confirm compound targets.

g. Cytochrome $BC_1$ Complex Assays

Enzyme assays were conducted essentially as described in Smilkstein, M. J. et al., A drug -selected *Plasmodium falciparum* lacking the need for conventional electron transport. *Mol Biochem Parasitol* 159 (1), 64 (2008). Briefly, cytochrome c reduction was monitored at 550-542 nm with an Agilent Diode Array 8453 spectrophotometer. The cuvette initially contained 50 μM oxidized cytochrome c (horse heart, Sigma-Aldrich), 50 μM decylubiquinol, 2 mM KCN, 100 mM KCl, and 50 mM Tricine (pH=8.0). The reaction was initiated by addition of 40 μg of mitochondrial protein solubilized in 2 mg/ml dodecyl maltoside, after correcting for the background reduction of cytochrome c by decylubiquinol. The initial rate of cytochrome c reduction in the presence and absence of inhibitors was measured after the addition of mitochondrial protein.

h. Thermal Melt Shift Assay

In brief, initial screening of compound-protein interactions (Crowther, G. J. et al., Buffer optimization of thermal melt assays of *Plasmodium* proteins for detection of small-molecule ligands. *J. Biomol. Screen* 14 (6), 700 (2009)) was done in 96-well plates at compound concentrations of 25 μM and protein concentrations of 100 μg/ml, using a standard buffer (100 mM HEPES, 150 mM NaCl, pH 7.5) except for a few proteins found to yield better melting curves in alternative buffers. Any compound that appeared to raise a protein's melting temperature ($T_m$) by ≥2 ° C. in this initial screen was subsequently tested for dose -dependent stabilization of the protein at concentrations of 100, 50, 25, 12.5, 6.25, 3.1, and 1.6 μM. Chemicals causing dose-dependent increases in the protein's $T_m$ were then considered validated hits. Table IV provides the protein name/function and PlasmoDB.org identifier for the protein targets in this study. Dissociation constants (Kd's) for protein-ligand interactions at 37 C.° are shown in Table V and were calculated by the method of M.C. Lo et al. (Krungkrai, J., The multiple roles of the mitochondrion of the malarial parasite. Parasitology 129 (Pt 5), 511

(2004)) except that the change in heat capacity of protein unfolding was estimated from amino acid length (Robertson, A. D. and Murphy, K. P., Protein Structure and the Energetics of Protein Stability. *Chem Rev* 97 (5), 1251 (1997)), as suggested by D. Matulis et al. (Matulis, D., Kranz, J. K., Salemme, F. R., and Todd, M. J., Thermodynamic stability of carbonic anhydrase: measurements of binding affinity and stoichiometry using ThermoFluor. *Biochemistry* 44 (13), 5258 (2005)).

TABLE IV

Identity of *Plasmodium* proteins tested in thermal-melt shift experiments

| Protein name/function | PlasmoDB.org identifier |
| --- | --- |
| 2C-methyl-D-erythritol 2,4-cyclodiphosphate synthase (IspF) | PVX_003920 |
| 6-phosphogluconolactonase | PF14_0511 |
| 6-pyruvoyltetrahydropterin synthase | PFF1360w |
| 6-pyruvoyltetrahydropterin synthase | PVX_114505 |
| Adenosine deaminase | PF10_0289 |
| Adenosine deaminase | PVX_111245 |
| Adenylosuccinate lyase | PVX_003765 |
| Adenylosuccinate synthetase | PF13_0287 |
| Aspartate carbamoyltransferase | PVX_083135 |
| CDK-related protein kinase 6 (PK6) | MAL13P1.185 |
| Choline kinase | PF14_0020 |
| Cyclophilin | PFE1430c |
| D-ribulose-5-phosphate 3-epimerase | PFL0960w |
| dUTPase | PF11_0282 |
| Dynein light chain 1 | PFL0660w |
| Eukaryotic translation initiation factor 5A (eIF5a) | PFL0210c |
| Farnesyl pyrophosphate synthase | PVX_092040 |
| Glutamate dehydrogenase (NADP-specific) | PF14_0164 |
| Glyceraldehyde-3-phosphate dehydrogenase | PF14_0598 |
| Glycerol-3-phosphate dehydrogenase | PFL0780w |
| Glycogen synthase kinase 3 | PFC0525c |
| Glyoxalase I | PF11_0145 |
| Guanylate kinase | PVX_099895 |
| Hypothetical protein, conserved | MAL13P1.257 |
| Hypothetical protein, conserved | PFF0880c |
| Methionine adenosyltransferase (a.k.a. SAM synthetase) | PFI1090w |
| Methionine aminopeptidase 1 | PF10_0150 |
| N-myristoyltransferase | PF14_0127 |
| Nucleoside diphosphate kinase B | PF13_0349 |
| Nucleosome assembly protein 1 | PKH_130240 |
| Ornithine aminotransferase | PY00104 |
| Orotidine 5' monophosphate decarboxylase | PF10_0225 |
| Peptidase, putative | PF14_0517 |
| Phosphatidylethanolamine-binding protein | PVX_123630 |
| Phosphoethanolamine N-methyltransferase | MAL13P1.214 |
| Phosphoglycerate kinase | PFI1105w |
| Phosphoglycerate mutase | PF11_0208 |
| Phosphomethylpyrimidine kinase | PFE1030c |
| Protein-L-isoaspartate O-methyltransferase | PF14_0309 |
| Rab11a GTPase | PF13_0119 |
| Rab18 GTPase | PF08_0110 |
| Ribonucleotide reductase, small subunit | PVX_086155 |
| Ribose 5-phosphate isomerase | PFE0730c |
| Ribosomal RNA methyltransferase | PF13_0052 |
| S-adenosylhomocysteine hydrolase | PFE1050w |
| Spermidine synthase | PF11_0301 |
| Superoxide dismutase | PB000490.02.0 |
| Superoxide dismutase | PKH_142350 |
| Thioredoxin | PF14_0545 |
| Thioredoxin peroxidase | PFL0725w |
| Thioredoxin reductase | PFI1170c |
| Tryptophan tRNA ligase | PF13_0205 |
| Ubiquitin carboxyl-terminal hydrolase | PF14_0576 |
| Ubiquitin conjugating enzyme | PF10_0330 |
| Ubiquitin conjugating enzyme | PFE1350c |
| Ubiquitin conjugating enzyme | PF13_0301 |
| Ubiquitin conjugating enzyme | PF08_0085 |
| Ubiquitin conjugating enzyme | PFC0255c |
| Ubiquitin conjugating enzyme | PFL0190w |
| Uridine phosphorylase (purine nucleoside phosphorylase) | PFE0660c |
| Vacuolar protein-sorting protein (VPS2) | PF08_0064 |

TABLE V

Calculated Kd's from thermal melt shift experiments and antimalarial activity

| Target combined with a compound of the invention | Kd (uM) | EC$_{50}$ 3D7 (uM) |
| --- | --- | --- |
| PF14_0511 (6PGL) | 0.63 | 1.04 |
| PF14_0511 (6PGL) | 0.66 | 0.40 |
| PVX_114505 (6PTPS) | 0.22 | 0.99 |
| PVX_114505 (6PTPS) | 8.55 | 0.50 |
| PVX_114505 (6PTPS) | 0.87 | 0.09 |
| PVX_114505 (6PTPS) | 1.27 | 0.44 |
| PVX_114505 (6PTPS) | 4.20 | 1 |
| PVX_114505 (6PTPS) | 2.99 | 1.30 |
| PF14_0020 (CK) | 2.62 | 1.94 |
| PF14_0020 (CK) | 0.60 | 0.80 |
| PF14_0020 (CK) | 0.52 | 0.50 |
| PF14_0020 (CK) | 0.09 | 1.14 |
| PFL0960w (DR5P3E) | 18.98 | 1.26 |
| PFL0960w (DR5P3E) | <0.1 | 0.60 |
| PF11_0282 (dUTPase) | 1.73 | 0.22 |
| PF11_0282 (dUTPase) | 0.59 | 0.40 |
| PFC0525c (GSK) | 6.33 | 0.22 |
| PF14_0545 (TR) | <0.1 | 0.40 | i. Compound Solubility Measurements

Solubility assay was carried out on Biomek FX lab automation workstation (Beckman Coulter, Inc., Fullerton, Calif.) using uSOL Evolution software (pION Inc., Woburn, Mass.). The detailed method is described as follows. 10 µl of compound stock was added to 190 µl 1-propanol to make a reference stock plate. 5 µl from this reference stock plate was mixed with 70 µl 1-propanol and 75 µl citrate phosphate buffered saline (isotonic, pH 3, 5 and 7.4) to make the reference plate, and the UV spectrum (250 nm–500 nm) of the reference plate was read. 6 µl of 10 mM test compound stock was added to 600 µL buffer in a 96-well storage plate and mixed. The storage plate was sealed and incubated at room temperature for 18 hours. The suspension was then filtered through a 96-well filter plate (pION Inc., Woburn, Mass.). 75 µl filtrate was mixed with 75 µl 1-propanol to make the sample plate, and the UV spectrum of the sample plate was read. Calculation was carried out by µSOL Evolution software based on the AUC (area under curve) of the UV spectrum of the sample plate and the reference plate. All compounds were tested in triplicate.

6. In Vivo Methods a. In Vivo Mouse Preliminary Safety

Compounds were administered as suspensions in 1% methylcellulose to 6-week-old CD-1 female mice. Animals received single i.p. bolus doses of compounds at a 10 ml/kg rate of administration. Top initial dose in all cases was 500 mg/kg. Based on the appearance of mortality or severe adverse findings, doses were scaled down until the maximum non-lethal dose was defined.

b. In Vivo Mouse Pharmacokinetic Profile

Experimental 6-week-old CD-1 mice (n=5 mice/group) received a single bolus dose of compounds of the invention (25 mg/kg, i.p., suspension in 1% methylcellulose). Blood samples (25 µl) were collected by puncture of the lateral tail vein, mixed 1:1 with de-ionized water 0.1% saponin and stored frozen at −70° C. until use. After protein precipitation and liquid/liquid extraction, the samples were assayed by LC/MS ESI conditions by selected ion monitoring in an API 4000 mass spectrometer (Applied Biosystems Sciex, Foster City, Calif.) coupled to a HPLC chromatograph (Agilent HP1100 Series, Agilent Technologies, Spain). Quantification was conducted by comparison to calibration curves. Blood concentrations versus time data were analyzed by non-compartmental analysis (NCA) methods using WinNonlin® Professional Version 5.0 (Pharsight Corporation, Mountain View, Calif.) and GraphPad Prism® 4.0 (GraphPad Software).

c. In Vivo Mouse Therapeutic Efficacy Assay

Cohorts of 8-week-old female CD1 mice (Harlan, Gannat, France) were infected i.v. with $6.4 \times 10^6$ *P. yoelii* 17X-parasitized erythrocytes obtained from infected donors, and randomly distributed in groups of n=5 mice/group (day 0). The compound of the invention was administered as a suspension in water 1%-methylcellulose at 5, 25, 50 and 100 mg/kg i.p. every 12 h starting one hour after infection. Chloroquine administered in saline solution at 1, 2, and 4 mg/kg p.o. every 24 h was included as control of efficacy. All compounds and control vehicles were administered orally in a volume of 20 ml/kg. Parasitemia was measured in peripheral blood (2 µl/mouse) every 24 h after infection. Infected erythrocytes were detected (0.01% detection limit) by flow cytometry using the nucleic acid dye YOYO-1 (Jimenez-Diaz, M. B. et al., Improvement of detection specificity of *Plasmodium*-infected murine erythrocytes by flow cytometry using autofluorescence and YOYO-1. *Cytometry Part A* 67 (1), 27 (2005).) Efficacy was expressed as the percentage of reduction of parasitemia with respect to vehicle-treated controls.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

d. In Vivo Pharmacokinetic Analysis in Infected Mice

The levels of compounds are evaluated in whole blood in order to determine standard pharmacokinetic parameters. Peripheral blood samples (25 µl) are taken at different times (0.25, 0.5, 1, 3, 6, 8, 10 and 23 hours after the first administration of compound), mixed with 25 µl of saponine solution (0.1% in water) and immediately frozen on dry ice. The frozen samples are stored at −80 ° C. until analysis. Vehicle-treated mice suffer the same blood-sampling regimen. Blood samples are processed under standard liquid-liquid extraction conditions. Analysis by HPLC/MSMS is performed for quantification. The lower limit of quantification (LLOQ) in this assay is 1 ng/ml. Blood concentration vs time is analyzed by non-compartmental analysis (NCA) using WinNonlin ver. 5.2 (from Pharsight); exposure-related values (Cmax and AUCO-t) and tmax are estimated.

e. In Vivo Efficacy Study (*P. Falciparum*)

The therapeutic efficacy of compounds against *P. falciparum* 3D7 is studied in a "4-day test". Briefly, groups of three mice engrafted with human erythrocytes are infected with $20 \times 10^6$ *P. falciparum* infected erythrocytes per mouse. Infections are performed by intravenous inoculation. The mice are randomly assigned to their corresponding experimental groups. The treatment starts at day 3 and finishes at day 6 after infection. The volume of administration (20 ml/Kg) is calculated daily for each mouse according to its body weight. Parasitemia is measured in samples of 2 µl from peripheral blood obtained at days 3, 4, 5, 6, and 7 after infection. A qualitative analysis of the effect of treatment on *P. falciparum* 3D70087/N9 is assessed by microscopy and flow cytometry. Samples of peripheral blood are stained with TER-119-Phycoerythrine (marker of murine erythrocytes) and SYTO-16 (nucleic acid dye) and then acquired by flow cytometer (FACSCalibur, BD). Microscopic analysis of Giemsa-stained blood smears from samples taken at days 5 and 7 (48 and 96 h after start of treatment, respectively) is performed at 100× magnification.

f. In Vivo Efficacy Study (*P. Berghei*)

The therapeutic efficacy of compounds of the invention against *P. berghei* is studied using a "4-day test". Briefly, CD1 mice are infected with $1.5 \times 10^6$ *P. berghei*-infected erythrocytes.

Infections are performed by intravenous inoculation. All mice are randomly assigned to their corresponding dose group. The treatment starts at day 3 and finishes at day 6 after infection. Parasitemia is assessed in samples from peripheral blood obtained at days 3, 4, 5, 6, and 7 after infection. A qualitative analysis of the effect of treatment on *P. berghei* is assessed by microscopy and flow cytometry. Fixed samples of peripheral blood from *P. berghei*-infected mice are stained with YOYO-1 (nucleic acid dye). Then all samples are acquired in a flow cytometer (FACSCalibur, BD). The microscopy analysis is done with Giemsa-stained blood smears from samples taken at days 5 and 7 (48 and 96 h after start of treatment, respectively) and observed at 100× magnification.

g. In Vivo Mouse Preliminary Safety

Compounds were administered as suspensions in 1% methylcellulose to 6-week-old CD-1 female mice. Animals received single i.p. bolus doses of compounds at a 10 ml/kg rate of administration. Top initial dose in all cases was 500 mg/kg. Based on the appearance of mortality or severe adverse findings, doses were scaled down until the maximum non-lethal dose was defined.

7. Enantiomeric Mixtures of Enantiomers of Compounds of the Invention and Related Activities of the Specific Enantiomers Compounds (2) and (6) were prepared as racemates by the route shown in Scheme 1 above as specifically described below in Schemes 2 and 3. The enantiomers were prepared and isolated to assay their antimalarial activities.

a. Preparation of Enantiomeric Mixture of Compound (2) and Separation of Enantiomers

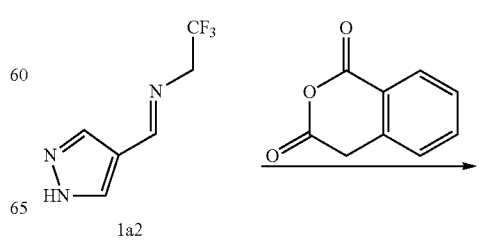

Scheme 2

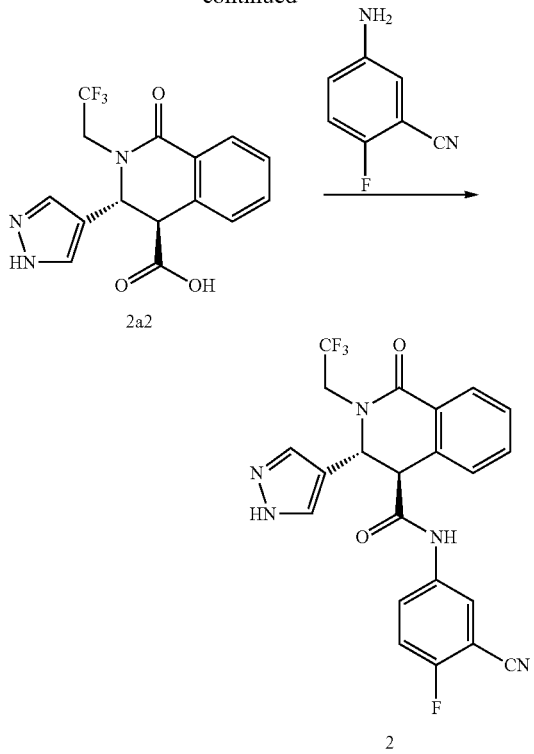

(1H-Pyrazol-4-ylmethylene)-(2,2,2-trifluoro-ethyl)-amine (1a1) (intermediate of Formula 1a when $R^1$ is $CF_3$ and Ar1 is 4-pyrazolyl)

To a solution of 2,2,2-Trifluoroethylamine hydrochloride (Sigma-Aldrich) (15.2 g, 113.2 mmol) in acetonitrile (36 mL) was added 3-pyrazole carboxaldehyde hydrochloride (which could be prepared as described in Traydakov, et. al., *Synthetic Communications*, 2011, 41, 2430-2434) (10 g, 75.75 mmol) followed by triethylamine (31.5 ml, 226.4 mmol) at 0° C.

The resulting reaction mixture was allowed to warm to room temperature and stirred at room temperature (RT) for 15 hours. The reaction mixture was filtered and the solids washed with acetonitrile. The filtrate was then concentrated in vacuo. The residue was suspended in ethyl ether, filtered and concentrated to afford 12 g (90%) of the title compound as white foam. $^1$H NMR (400 MHz, DMSO-d6) δ4.10-4.30 (m, 2H), 7.70-8.32 (m, 2H), 8.37 (s, 1H), 13.22 (br, 1H). $^{13}$C NMR (400 MHz, DMSO-d6) δ60.70 (q, J=116 Hz, *CH2CF3), 120.0, 126.0 (q, J=1100 Hz, CH2*CF3), 131.2, 138.9, 160.4. MS(ESI, [M+H]+), 178.4.

1-Oxo-3-(1H-pyrazol-4-yl)-2-(2,2,2-trifluoro-ethyl)-1,2,3,4-tetrahydro-isoquinoline-4-carboxylic acid (2a2) (intermediate of Formula 2a when $R^1$ is $CF_3$, Ar1 is 4-pyrazolyl, $R^2$ and $R^3$ are H)

A solution of 1a2 (13.1 g, 74 mmol) in acetonitrile (260 mL) was cooled to –20° C. and homophthalic anhydride (Alfa Aesar) (10 g, 61.67 mmol) was added slowly. The reaction mixture was stirred at –20° C. for 40 min during which time a yellow precipitate formed. The reaction mixture was then allowed to warm to room temperature, stirred for 20 minutes and then heated to reflux (82-83° C.) for 15 hours. After the reaction had cooled to room temperature, the white solid was filtered, washed with n-hexane, and then dried under vacuum to afford 12.2 g (58.4%) of the title compound (2a2) as a white solid. mp>217° C., decomp. $^1$H NMR (400 MHz, Methanol-d4) δ3.84 (m, 1H), 4.15 (d, J=1.6 Hz, 1H), 4.71 (m, 1H), 5.53 (d, J=1.6 Hz, 1H), 7.28 (s, 1H), 7.35 (d, J=7.5 Hz, 1H), 7.50 (t, J=7.5 Hz, 1H), 7.58 (t, J=7.5 Hz, 1H), 8.07 (d, J=7.5 Hz, 1H). $^{13}$C NMR (400 MHz, DMSO-d6) δ46.5 (q, J=136 Hz, CF3*CH2), 51.0, 56.1, 117.0, 119.4, 125.0 (q, J=1112 Hz, CF3), 127.8, 128.3, 128.4, 129.8, 132.0, 133.0, 135.1, 165.28, 172.24. MS(ESI, [M+H]+), 340.0.

N-(3-cyano,4-fluorophenyl)-1-Oxo-3-(1H-pyrazol-4-yl)-2-(2,2,2-trifluoro-ethyl)-1,2,3,4-tetrahydro-isoquinoline-4-carboxamide (2)

A solution of 2a2 (448 mg, 1.32 mmol) and 5-amino-2-fluorobenzonitrile (Sigma-Aldrich) (269 mg, 1.98 mmol) in 20 mL acetonitrile was treated with phosphorus oxychloride (0.136 mL, 1.45 mmol) and heated to reflux for 3 hours. The reaction mixture was quenched with ice water and extracted twice with ethyl acetate. The combined organic layers were washed with saturated aqueous sodium carbonate solution, dried over sodium sulfate and concentrated in vacuo. The crude product was purified by column chromatography (Silica, 20-100% ethyl acetate in hexane) to afford 420 mg (70%) of the title compound as an off-white foam. $^1$H NMR (300 MHz, Methanol-d4) δ3.81(m, 1H), 4.27 (s, 1H), 4.71 (m, 1H), 5.27 (s, 1H), 7.30-7.40 (m, 2H), 7.43 (m, 1H), 7.45-7.53 (m, 3H), 7.54-7.60 (m, 1H), 7.86 (m, 1H), 7.95 (m, 1H). $^{13}$C NMR (500 MHz, Methanol-d4) δ45.7 (q, J=150 Hz, *CH2CF3), 52.5, 56.9, 100.9, 113.3, 116.6, 116.8, 119.5, 124.3, 124.9 (q, J=1114 Hz, CH2*CF3), 127.2, 128.0, 128.6, 128.8, 133.1, 129.3, 134.6, 135.7, 158.5, 160.5, 165.3, 169.4. MS (ESI, [M+H]+), 458.5.

1-Oxo-3-(1H-pyrazol-4-yl)-2-(2,2,2-trifluoro-ethyl)-1,2,3,4-tetrahydro-isoquinoline-4-carboxylic acid methyl ester (Methyl ester of 2a2)

To a solution of 2a2 (2 g, 5.89 mmol) in methanol (30 mL) was added 0.25 mL of concentrated sulfuric acid at room temperature. The reaction mixture was then heated to reflux for 15 hours (64~65° C.). The reaction mixture was quenched with saturated sodium carbonate and extracted with ethyl acetate (3×100 mL). The combined organic layers were dried over sodium sulfate, filtered and concentrated in vacuo to afford 1.75 g (84%) of the title compound as an off-white foam. Recrystallization from 2:1 heptane:isopropyl alcohol afforded a white solid, m.p.=161-162° C. 1H NMR (300 MHz, CDCl3-d6) δ3.46 (m, 1H), 3.94 (d, J=1.8 Hz, 1H), 4.81 (m, 1H), 5.39 (d, J=1.8 Hz, 1H), 7.14-7.30 (m, 3H), 7.42-7.58 (m, 2H), 8.17 (m, 1H). MS (ESI, [M+H]+), 354.6.

Separation of (+)-2 and (–)-2

The racemic methyl ester of 2a2 was subjected to preparative super fluid chromatographic (SFC) separation on a 250× 30 mm Chiralpak AD-H column eluted with a mixture of 30% MeOH in $CO_2$ at a flow rate of 100 mL/min to afford the enantiomers of the methyl ester of 2a2. Subsequent to ester hydrolysis (LiOH, MeOH, $H_2O$), conversion of each acid enantiomer to their corresponding amides by the procedures described above afforded the enantiomers of 2. l-(N-(3-cyano,4-fluorophenyl)-1-Oxo-3-(1H-pyrazol-4-yl)-2-(2,2,2-trifluoro-ethyl)-1,2,3,4-tetrahydroisoquinoline-4-carboxamide, $[\alpha]_D$=–154.3 c=1.0, MeOH (RT=18.5 min, OJ-H 250× 4.6 mm column eluted with 0.1% DEA in 80-20 Hexane-EtOH). d-N-(3-cyano,4-fluorophenyl)-1-Oxo-3-(1H-pyrazol-4-yl)-2-(2,2,2-trifluoro-ethyl)-1,2,3,4-tetrahydroisoquinoline-4-carboxamide, $[\alpha]_D$=+151.6 c=1.0, MeOH (RT=25.5 min).

b. Preparation of Enantiomeric Mixture of Compound (6) and Separation of Enantiomers

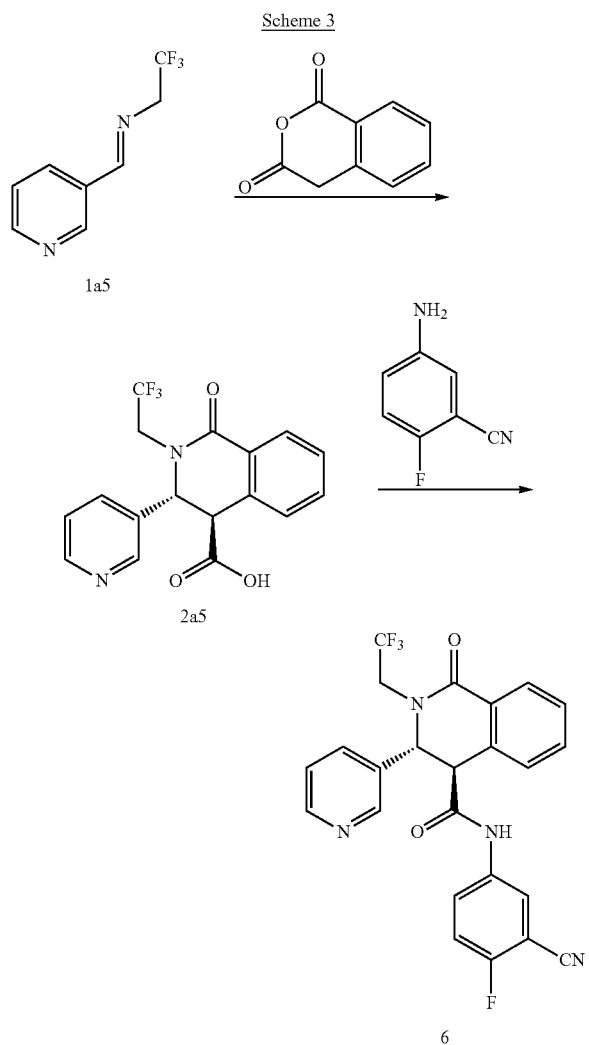

Pyridine-3-ylmethylene-(2,2,2-trifluoro-ethyl)-amine (1a2) (intermediate of Formula 1a when $R^1$ is $CF_3$ and Ar1 is 3-pyridinyl)

To a solution of 2,2,2-Trifluoroethylamine hydrochloride (3.98 g, 29.4 mmol) in acetonitrile (9 mL) was added 3-pyridinecarboxaldehyde (Sigma-Aldrich) (2.1 g, 19.6 mmol) followed by triethylamine (4 ml, 29.43 mmol) at 0° C. The resulting mixture was stirred at room temperature for 15 hours. The reaction mixture was filtered and the solids washed with acetonitrile. The filtrate was then concentrated in vacuo. The residue was taken up in ethyl ether, filtered and concentrated to afford 3.12 g (84%) of the tile compound as a white foam. $^1$H NMR (300 MHz, DMSO-$d_6$) δ4.40 (m, 2H), 7.52 (m, 1H), 8.18 (m, 1H), 8.61 (s, 1H), 8.70 (dd, J=1.8, 4.8 Hz, 1H), 8.92 (d, J=1.8, 1H). MS (ESI, [M+H] +), 189.5.

1-Oxo-3-pyridin-3-yl-2-(2,2,2-trifluoro-ethyl)-1,2,3,4-tetrahydro-isoquinoline-4-carboxylic acid (2a5) (intermediate of Formula 2a when $R^1$ is $CF_3$, Ar1 is 3-pyridinyl, $R^2$ and $R^3$ are H)

To a solution of 1a5 (3.12 g, 16.5 mmol) in acetonitrile (58 mL) cooled to −20° C., homophthalic anhydride (2.22 g, 13.75 mmol) was added slowly. The reaction mixture was stirred at −20° C. for 40 min during which time a yellow precipitate formed. The reaction mixture was then allowed to warm up to room temperature, stirred for 20 minutes and then heated to reflux (82~83° C.) for 15 hours. After cooling to room temperature, the white solid was filtered, washed with n-hexane, and dried under vacuum to afford 1.5 g (31%) of the title compound (2a5). mp>217° C., decomp. $^1$H NMR (300 MHz, DMSO-$d_6$) δ4.03 (m, 1H), 4.29 (s, 1H), 4.66 (m, 1H), 5.59 (s, 1H), 7.22-7.32 (m, 2H), 7.40 (m, 1H), 7.42-7.54 (m, 2H), 7.98 (dd, J=2, 6.9 Hz, 1H), 8.35 (d, J=2 Hz, 1H), 8.41 (dd, J=2, 4.8 Hz, 1H). MS (ESI, [M+H]$^+$), 351.6.

N-(3-cyano-4-fluoro)-1-Oxo-3-pyridin-3-yl-2-(2,2,2-trifluoro-ethyl)-1,2,3,4-tetrahydro-isoquinoline-4-carboxamide (6)

A solution of compound 2a5 (462 mg, 1.32 mmol) and 5-amino-2-fluorobenzonitrile (269 mg, 1.98 mmol) in 20 mL acetonitrile was treated with phosphorus oxychloride (0.136 mL, 1.45 mmol) and then refluxed for 3 hours. The reaction mixture was cooled and quenched with ice water and extracted twice with ethyl acetate. The combined organic layers were washed with saturated aqueous sodium carbonate, dried over sodium sulfate and concentrated in vacuo. The crude product was purified by column chromatography (Silica, 20-100% ethyl acetate in hexane) to afford 543 mg (88%) of the title compound as an off-white foam. $^1$H NMR (300 MHz, Methanol-$d_4$) δ4.11 (m, 1H), 4.19 (s, 1H), 4.56 (m, 1H), 5.55 (s, 1H), 7.22 (m, 1H), 7.30-7.40 (m, 2H), 7.45-7.60 (m, 3H), 7.84 (m, 1H), 8.00 (m, 1H), 8.13 (m, 1H). 8.41 (m, 1H), 8.46 (m, 1H). MS(ESI, [M+H]$^+$), 469.6.

1-Oxo-3-pyridin-3-yl-2-(2,2,2-trifluoro-ethyl)-1,2,3,4-tetrahydro-isoquinoline-4-carboxylic acid methyl ester (methyl ester of 2a5)

Concentrated sulfuric acid (8.39 g, 0.0856 mol) was added dropwise to a stirred solution of 2a5 (10 g, 0.0285 mol) in dry methanol (100 ml) at 0° C. After completing the addition, the reaction mixture was maintained at this temperature for 1h and then heated to reflux for 6h. The reaction was then cooled to room temperature and concentrated in vacuo. The resulting slurry was suspended in saturated sodium bicarbonate solution and extracted with chloroform (3×500 mL). The combined organic phase was dried over anhydrous sodium sulphate, filtered, and concentrated in vacuo. The crude product was purified by silica gel column chromatography to provide the title compound as a white solid 8 g, 76.93%. $^1$H NMR (400 MHz, DMSO-d6): δ8.40 (dd, J=1.36, 4.68 Hz, 1H), 8.34 (d, J=2.20 Hz, 1H), 7.98 (dd, J=1.56, 7.48 Hz, 1H), 7.43-7.52 (m, 2H), 7.39-7.41 (m, 1H), 7.25-7.28 (m, 2H), 5.58 (s, 1H), 4.68-4.79 (m, 1H), 4.48 (s, 1H), 3.93-4.04 (m, 1H), 3.66 (s, 3H). LC-MS (APCI, [M+H]$^+$), 365.2.

Separation of (+)-6 and (−)-6

The racemic methyl ester of 2a5 was subjected to preparative SFC chromatographic separation on a 250×30 mm Chiralpak AD-H column eluted with a mixture of 30% MeOH in $CO_2$ at a flow rate of 100 mL/min to afford the two enantiomers of the methyl ester of 2a5. Subsequent to ester hydrolysis (LiOH, MeOH, $H_2O$), conversion of each acid enantiomer to its corresponding amide by the procedures described above afforded the enantiomers of (6). l-N-(3-cyano-4-fluoro)-1-Oxo-3-pyridin-3-yl-2-(2,2,2-trifluoro-ethyl)-1,2,3,4-tetrahydro isoquinoline-4-carboxamide, $[α]_D$=−152.7 c=1.0, MeOH (RT=11.0 min, OJ-H 250×4.6 mm column eluted with 0.1% diethylamine in 80-20 Hexane-EtOH). d-N-(3-cyano-4-fluoro)-1-Oxo-3-pyridin-3-yl-2-(2,2,2-trifluoro-ethyl)-1,2,3,4-tetrahydro-isoquinoline-4-carboxamide, [α]p=+145.8 c=1.0, MeOH (RT=14.8 min).

c. Antimalarial Activities of Specific Enantiomers of the Invention

The antimalarial activities of the enantiomers were assayed as described in 4a and are presented in Table VI below.

TABLE VI

| Compound | Isomer | Optical Rotation $[\alpha]_D$ | Potency (nM, 3D7 strain) |
|---|---|---|---|
| Compound 6 | l | −62 | 477 |
| Compound 6 | d | +52 | 15 |
| Compound 2 | l | −154 | 303 |
| Compound 2 | d | +154 | 35 |
| Compound 20 | l | −186 | 233 |
| Compound 20 | d | +185 | 11 |

These data show that the d-isomer provides the majority of the antimalarial activity of the racemates for the above compounds of the invention.

8. In Vivo Data

The compounds of the invention were tested in vivo as follows:

a. Metabolism Studies in Mice

The metabolism of compounds of the invention was assayed as described in Method 6 above and results are presented on FIG. 1. The pharmacokinetic parameters are compared to those of a reference compound (1247) described in Guiguemde et al., 2010, *Nature* 465, 311-315 as an antimalarial agent which was reported as being potent in vitro, but exhibited low solubility and poor stability in in vitro models of liver metabolism. Additionally, reference compound 1247) has very low peak exposure and poor stability and total exposure in vivo. These data show that compounds of the invention not only present reasonable potency in vitro but have greatly improved solubility (100-fold), stability in in vitro liver metabolism models (stable to detection limit of assay) and significantly improved peak exposure (100-fold), total exposure (55- to 77-fold), and stability (1- to 2-fold) in vivo.

b. Antimalarial Activity in Mice

Figure 2:
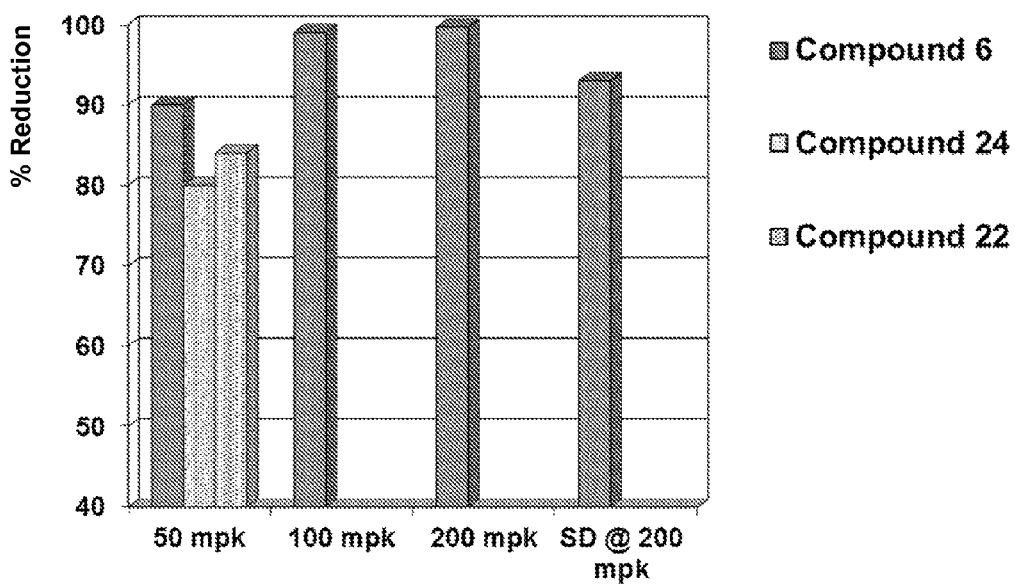
FIG. 2 shows the in vivo efficacies of compounds of the invention against *P. berghei* and *P. falciparum* in mice as described in Methods 6 and 8. 1A: % reduction in parasitemia in *P. berghei* infected mice after four days of once daily oral treatment with compounds at the indicated doses, or a single oral treatment at the indicated dose (SD). mpk: milligram compound per kilogram body weight. 1B: reduction of parasitemia (log parasitemia) in response to varying doses of compounds of the invention, each given as 4 sequential single daily oral doses in *P. falciparum* and *P. berghei* infected mice.
Figure 2:
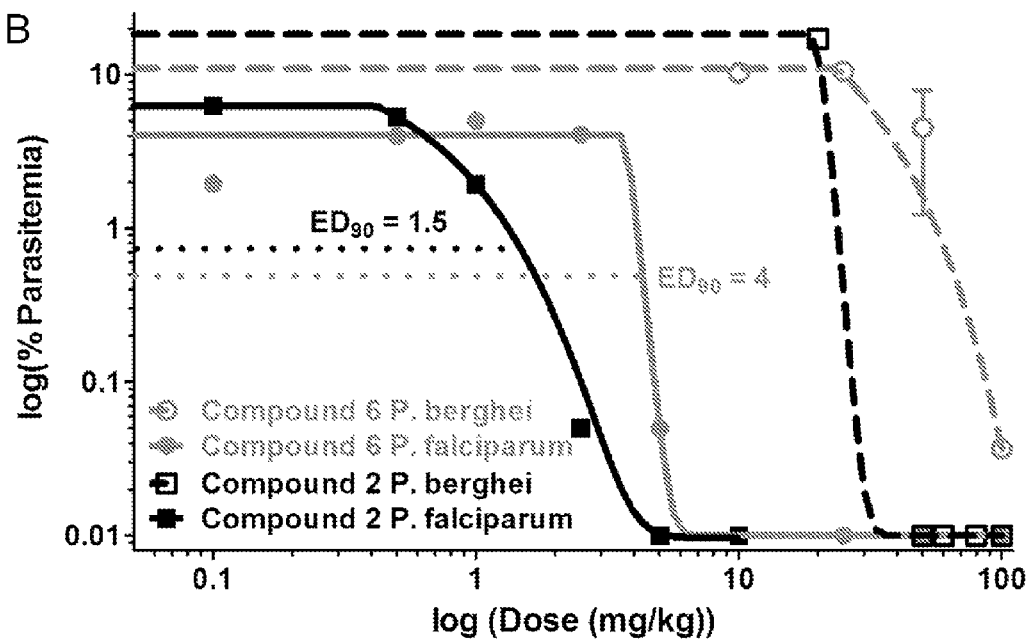

The antimalarial activities of compounds of the invention were assayed as described in Method 6 above and results are presented on FIGS. 2A and 2B. For the sake of comparison reference compound (1247) was assayed and found completely inactive.

Results of FIG. 2A clearly demonstrate that both compounds of the invention are highly potent and efficacious by the oral route and that both compounds are significantly more potent against human malaria (Pf) than against rodent malaria (Pb). These results clearly indicate that improvements in exposure by the oral route observed for compounds of the invention lead to efficacy in reducing malaria by the oral route. Therefore, altogether, these data show clear improvement in the exposure of the compounds of the invention relative to the reference compounds which have pharmacokinetic parameters matching the requirements of an antimalarial drug.

The invention claimed is:

1. A compound having a structure represented by a formula:

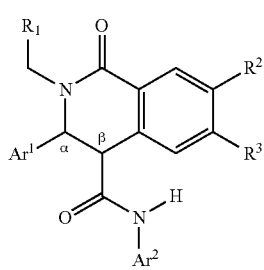

(II)

wherein $Ar^1$ is selected from 3-pyridinyl, 4-isoxazolyl, N-methyl-4-pyrazolyl, 4-pyrazolyl, 4-isothiazolyl, 5-thiazolyl, 5-pyrimidinyl, or 4-pyridazinyl; $R^1$ is selected from $CF_3$, $(CH_3)_2CH$ or cyclopropyl, $R^2$ and $R^3$ are independently selected from H, $OCH_3$ or F; $Ar^2$ has a structure represented by a formula:

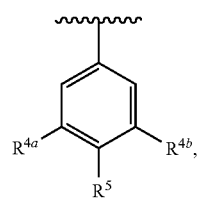

wherein $R^{4a}$, $R^{4b}$ and $R^5$ are independently selected from H, CN, F, Cl or $OCF_3$, or a pharmaceutically acceptable salt, tautomer, geometrical isomer or optically active form thereof.

2. The compound of claim 1 wherein R1 is CF3.
3. The compound of claim 1 wherein R1 is $(CH_3)_2CH$.
4. The compound of claim 1 wherein R1 is cyclopropyl.
5. The compound according to claim 1, selected from:
N-(3-cyano-4-fluorophenyl)-1-oxo-3-(pyridin-3-yl)-2-(2,2,2-trifluoroethyl)-1,2,3,4-tetrahydroisoquinoline-4-carboxamide;
N-(3-chloro-5-cyanophenyl)-1-oxo-3-(pyridin-3-yl)-2-(2,2,2-trifluoroethyl)-1,2,3,4-tetrahydroisoquinoline-4-carboxamide;
N-(3-cyanophenyl)-1-oxo-3-(pyridin-3-yl)-2-(2,2,2-trifluoroethyl)-1,2,3,4-tetrahydroisoquinoline-4-carboxamide;
N-(3-cyano-5-fluorophenyl)-1-oxo-3-(pyridin-3-yl)-2-(2,2,2-trifluoroethyl)-1,2,3,4-tetrahydroisoquinoline-4-carboxamide;
1-oxo-3-(pyridin-3-yl)-2-(2,2,2-trifluoroethyl)-N-(3-(trifluoromethoxy)phenyl)-1,2,3,4-tetrahydroisoquinoline-4-carboxamide;
N-(4-fluoro-3-(trifluoromethoxy)phenyl)-1-oxo-3-(pyridin-3-yl)-2-(2,2,2-trifluoroethyl)-1,2,3,4-tetrahydroisoquinoline-4-carboxamide;
N-(3-fluoro-5-(trifluoromethoxy)phenyl)-1-oxo-3-(pyridin-3-yl)-2-(2,2,2-trifluoroethyl)-1,2,3,4-tetrahydroisoquinoline-4-carboxamide;
N-(3-cyano-4-fluorophenyl)-2-(cyclopropylmethyl)-1-oxo-3-(pyridin-3-yl)-1,2,3,4-tetrahydroisoquinoline-4-carboxamide;
N-(3-cyano-5-fluorophenyl)-7-fluoro-3-(1-methyl-1H-pyrazol-4-yl)-1-oxo-2-(2,2,2-trifluoroethyl)-1,2,3,4-tetrahydroisoquinoline-4-carboxamide;
N-(3-cyano-4-fluorophenyl)-2-isobutyl-7-methoxy-1-oxo-3-(pyridin-3-yl)-1,2,3,4-tetrahydroisoquinoline-4-carboxamide;

N-(3-cyano-4-fluorophenyl)-2-isobutyl-1-oxo-3-(pyridin-3-yl)-1,2,3,4-tetrahydroisoquinoline-4-carboxamide;
N-(3-chloro-5-cyanophenyl)-2-isobutyl-1-oxo-3-(pyridin-3-yl)-1,2,3,4-tetrahydroisoquinoline-4-carboxamide;
N-(3-cyanophenyl)-2-isobutyl-1-oxo-3-(pyridin-3-yl)-1,2,3,4-tetrahydroisoquinoline-4-carboxamide;
N-(3-cyano-5-fluorophenyl)-2-isobutyl-1-oxo-3-(pyridin-3-yl)-1,2,3,4-tetrahydroisoquinoline-4-carboxamide;
2-isobutyl-1-oxo-3-(pyridin-3-yl)-N-(3-(trifluoromethoxy)phenyl)-1,2,3,4-tetrahydroisoquinoline-4-carboxamide;
N-(4-fluoro-3-(trifluoromethoxy)phenyl)-2-isobutyl-1-oxo-3-(pyridin-3-yl)-1,2,3,4-tetrahydroisoquinoline-4-carboxamide;
N-(3-fluoro-5-(trifluoromethoxy)phenyl)-2-isobutyl-1-oxo-3-(pyridin-3-yl)-1,2,3,4-tetrahydroisoquinoline-4-carboxamide;
N-(3-cyanophenyl)-6-fluoro-2-isobutyl-3-(1-methyl-1H-pyrazol-4-yl)-1-oxo-1,2,3,4-tetrahydroisoquinoline-4-carboxamide;
N-(3-cyano-4-fluorophenyl)-3-(1-methyl-1H-pyrazol-4-yl)-1-oxo-2-(2,2,2-trifluoroethyl)-1,2,3,4-tetrahydroisoquinoline-4-carboxamide;
N-(3-chloro-5-cyanophenyl)-3-(1-methyl-1H-pyrazol-4-yl)-1-oxo-2-(2,2,2-trifluoroethyl)-1,2,3,4-tetrahydroisoquinoline-4-carboxamide;
N-(3-cyanophenyl)-3-(1-methyl-1H-pyrazol-4-yl)-1-oxo-2-(2,2,2-trifluoroethyl)-1,2,3,4-tetrahydroisoquinoline-4-carboxamide;
N-(3-cyano-5-fluorophenyl)-3-(1-methyl-1H-pyrazol-4-yl)-1-oxo-2-(2,2,2-trifluoroethyl)-1,2,3,4-tetrahydroisoquinoline-4-carboxamide;
3-(1-methyl-1H-pyrazol-4-yl)-1-oxo-2-(2,2,2-trifluoroethyl)-N-(3-(trifluoromethoxy)phenyl)-1,2,3,4-tetrahydroisoquinoline-4-carboxamide;
N-(4-fluoro-3-(trifluoromethoxy)phenyl)-3-(1-methyl-1H-pyrazol-4-yl)-1-oxo-2-(2,2,2-trifluoroethyl)-1,2,3,4-tetrahydroisoquinoline-4-carboxamide;
N-(3-fluoro-5-(trifluoromethoxy)phenyl)-3-(1-methyl-1H-pyrazol-4-yl)-1-oxo-2-(2,2,2-trifluoroethyl)-1,2,3,4-tetrahydroisoquinoline-4-carboxamide;
2-butyl-N-(3-cyano-4-fluorophenyl)-1-oxo-3-(pyridin-3-yl)-1,2,3,4-tetrahydroisoquinoline-4-carboxamide;
N-(3-cyano-4-fluorophenyl)-2-isobutyl-3-(1-methyl-1H-pyrazol-4-yl)-1-oxo-1,2,3,4-tetrahydroisoquinoline-4-carboxamide;
N-(3-chloro-5-cyanophenyl)-2-isobutyl-3-(1-methyl-1H-pyrazol-4-yl)-1-oxo-1,2,3,4-tetrahydroisoquinoline-4-carboxamide;
N-(3-cyanophenyl)-2-isobutyl-3-(1-methyl-1H-pyrazol-4-yl)-1-oxo-1,2,3,4-tetrahydroisoquinoline-4-carboxamide;
N-(3-cyano-5-fluorophenyl)-2-isobutyl-3-(1-methyl-1H-pyrazol-4-yl)-1-oxo-1,2,3,4-tetrahydroisoquinoline-4-carboxamide;
2-isobutyl-3-(1-methyl-1H-pyrazol-4-yl)-1-oxo-N-(3-(trifluoromethoxy)phenyl)-1,2,3,4-tetrahydroisoquinoline-4-carboxamide;
N-(4-fluoro-3-(trifluoromethoxy)phenyl)-2-isobutyl-3-(1-methyl-1H-pyrazol-4-yl)-1-oxo-1,2,3,4-tetrahydroisoquinoline-4-carboxamide;
N-(3-fluoro-5-(trifluoromethoxy)phenyl)-2-isobutyl-3-(1-methyl-1H-pyrazol-4-yl)-1-oxo-1,2,3,4-tetrahydroisoquinoline-4-carboxamide;
N-(3-cyano-5-fluorophenyl)-6-fluoro-2-isobutyl-3-(1-methyl-1H-pyrazol-4-yl)-1-oxo-1,2,3,4-tetrahydroisoquinoline-4-carboxamide;
N-(3-cyano-4-fluorophenyl)-1-oxo-3-(1H-pyrazol-4-yl)-2-(2,2,2-trifluoroethyl)-1,2,3,4-tetrahydroisoquinoline-4-carboxamide;
N-(3-chloro-5-cyanophenyl)-1-oxo-3-(1H-pyrazol-4-yl)-2-(2,2,2-trifluoroethyl)-1,2,3,4-tetrahydroisoquinoline-4-carboxamide;
N-(3-cyanophenyl)-1-oxo-3-(1H-pyrazol-4-yl)-2-(2,2,2-trifluoroethyl)-1,2,3,4-tetrahydroisoquinoline-4-carboxamide;
N-(3-cyano-5-fluorophenyl)-1-oxo-3-(1H-pyrazol-4-yl)-2-(2,2,2-trifluoroethyl)-1,2,3,4-tetrahydroisoquinoline-4-carboxamide;
1-oxo-3-(1H-pyrazol-4-yl)-2-(2,2,2-trifluoroethyl)-N-(3-(trifluoromethoxy)phenyl)-1,2,3,4-tetrahydroisoquinoline-4-carboxamide;
N-(4-fluoro-3-(trifluoromethoxy)phenyl)-1-oxo-3-(1H-pyrazol-4-yl)-2-(2,2,2-trifluoroethyl)-1,2,3,4-tetrahydroisoquinoline-4-carboxamide;
N-(3-fluoro-5-(trifluoromethoxy)phenyl)-1-oxo-3-(1H-pyrazol-4-yl)-2-(2,2,2-trifluoroethyl)-1,2,3,4-tetrahydroisoquinoline-4-carboxamide;
N-(3-cyano-4-fluorophenyl)-7-fluoro-2-isobutyl-3-(1-methyl-1H-pyrazol-4-yl)-1-oxo-1,2,3,4-tetrahydroisoquinoline-4-carboxamide;
N-(3-cyano-4-fluorophenyl)-2-isobutyl-1-oxo-3-(1H-pyrazol-4-yl)-1,2,3,4-tetrahydroisoquinoline-4-carboxamide;
N-(3-chloro-5-cyanophenyl)-2-isobutyl-1-oxo-3-(1H-pyrazol-4-yl)-1,2,3,4-tetrahydroisoquinoline-4-carboxamide;
N-(3-cyanophenyl)-2-isobutyl-1-oxo-3-(1H-pyrazol-4-yl)-1,2,3,4-tetrahydroisoquinoline-4-carboxamide;
N-(3-cyano-5-fluorophenyl)-2-isobutyl-1-oxo-3-(1H-pyrazol-4-yl)-1,2,3,4-tetrahydroisoquinoline-4-carboxamide;
2-isobutyl-1-oxo-3-(1H-pyrazol-4-yl)-N-(3-(trifluoromethoxy)phenyl)-1,2,3,4-tetrahydroisoquinoline-4-carboxamide;
N-(4-fluoro-3-(trifluoromethoxy)phenyl)-2-isobutyl-1-oxo-3-(1H-pyrazol-4-yl)-1,2,3,4-tetrahydroisoquinoline-4-carboxamide;
N-(3-fluoro-5-(trifluoromethoxy)phenyl)-2-isobutyl-1-oxo-3-(1H-pyrazol-4-yl)-1,2,3,4-tetrahydroisoquinoline-4-carboxamide;
N-(3-chloro-5-cyanophenyl)-7-fluoro-2-isobutyl-3-(1-methyl-1H-pyrazol-4-yl)-1-oxo-1,2,3,4-tetrahydroisoquinoline-4-carboxamide;
N-(3-cyano-4-fluorophenyl)-2-isobutyl-3-(isothiazol-4-yl)-1-oxo-1,2,3,4-tetrahydroisoquinoline-4-carboxamide;
N-(3-cyano-4-fluorophenyl)-2-isobutyl-1-oxo-3-(pyrimidin-5-yl)-1,2,3,4-tetrahydroisoquinoline-4-carboxamide; or
N-(3-cyano-4-fluorophenyl)-1-oxo-3-(1H-pyrazol-4-yl-6,7-difluoro-2-(2,2,2-trifluoroethyl)-1,2,3,4-tetrahydroisoquinoline-4-carboxamide.

6. A pharmaceutical composition comprising at least one compound according to claim 1 and a pharmaceutically acceptable carrier, diluent or excipient thereof.

7. A pharmaceutical formulation comprising at least one compound according to claim 1 or a pharmaceutically acceptable salt, tautomer, geometrical isomer or optically active form thereof, the formulation further comprising at least one further antimalarial agent.

8. The pharmaceutical formuation according to claim 7, wherein the further antimalarial agent is selected from artemisinin or an artemisinin derivative selected from artemether and dihydroartemisinin, chloroquine, mefloquine, quinine, atovaquone/proguanil, doxycycline, hydroxychloroquine, pyronaridine, lumefantrine, pyrimethamine-sulfadoxine, quinacrine, chloroquine, primaquine, doxycycline, atovaquone, proguanil hydrochloride, piperquine, ferroquine, tafenoquine, arterolane, Spiro[3H-indole-3,1'-[1H]pyrido[3,4- b]indol]-2(1H)-one, 5,7'-dichloro-6'-fluoro-2',3',4',9'-tetrahydro-3'-methyl-,(1'R,3'S)-], [4-[[2-(1,1-difluoroethyl)-5-methyl[1,2,4]triazolo[1,5-a]pyrimidin-7-yl]amino]phenyl]pentafluoro-sulfur], or 4-[2-(4-cis-dispiro[cyclohexane-1,3'-[1,2,4]trioxolane-5',2''-tricyclo[3.3.1.13,7]decan]-4-ylphenoxy)ethyl]-morpholine.

9. A method for the prevention or treatment of malaria, the method comprising administering a therapeutically effective amount of a compound according to claim 1 to a primate in need of the prevention or treatment of malaria.

10. The method according to claim 9, further comprising the administration of one or more additional antimalarial agent.

11. A method for inactivating parasitic infection in a cell, comprising the step of contacting the cell with an effective amount of at least one compound according to claim 1.

12. A method for the prevention or treatment of malaria comprising the step of administering to a primate in need thereof, a therapeutically effective amount of at least one compound selected from:

N-(3-cyano-4-fluorophenyl)-1-oxo-3-(pyridin-3-yl)-2-(2,2,2-trifluoroethyl)-1,2,3,4-tetrahydroisoquinoline-4-carboxamide;
N-(3-chloro-5-cyanophenyl)-1-oxo-3-(pyridin-3-yl)-2-(2,2,2-trifluoroethyl)-1,2,3,4-tetrahydroisoquinoline-4-carboxamide;
N-(3-cyanophenyl)-1-oxo-3-(pyridin-3-yl)-2-(2,2,2-trifluoroethyl)-1,2,3,4-tetrahydroisoquinoline-4-carboxamide;
N-(3-cyano-5-fluorophenyl)-1-oxo-3-(pyridin-3-yl)-2-(2,2,2-trifluoroethyl)-1,2,3,4-tetrahydroisoquinoline-4-carboxamide;
1-oxo-3-(pyridin-3-yl)-2-(2,2,2-trifluoroethyl)-N-(3-(trifluoromethoxy)phenyl)-1,2,3,4-tetrahydroisoquinoline-4-carboxamide;
N-(4-fluoro-3-(trifluoromethoxy)phenyl)-1-oxo-3-(pyridin-3-yl)-2-(2,2,2-trifluoroethyl)-1,2,3,4-tetrahydroisoquinoline-4-carboxamide;
N-(3-fluoro-5-(trifluoromethoxy)phenyl)-1-oxo-3-(pyridin-3-yl)-2-(2,2,2-trifluoroethyl)-1,2,3,4-tetrahydroisoquinoline-4-carboxamide;
N-(3-cyano-4-fluorophenyl)-2-(cyclopropylmethyl)-1-oxo-3-(pyridin-3-yl)-1,2,3,4-tetrahydroisoquinoline-4-carboxamide;
N-(3-cyano-5-fluorophenyl)-7-fluoro-3-(1-methyl-1H-pyrazol-4-yl)-1-oxo-2-(2,2,2-trifluoroethyl)-1,2,3,4-tetrahydroisoquinoline-4-carboxamide;
N-(3-cyano-4-fluorophenyl)-2-isobutyl-7-methoxy-1-oxo-3-(pyridin-3-yl)-1,2,3,4-tetrahydroisoquinoline-4-carboxamide;
N-(3-cyano-4-fluorophenyl)-2-isobutyl-1-oxo-3-(pyridin-3-yl)-1,2,3,4-tetrahydroisoquinoline-4-carboxamide;
N-(3-chloro-5-cyanophenyl)-2-isobutyl-1-oxo-3-(pyridin-3-yl)-1,2,3,4-tetrahydroisoquinoline-4-carboxamide;
N-(3-cyanophenyl)-2-isobutyl-1-oxo-3-(pyridin-3-yl)-1,2,3,4-tetrahydroisoquinoline-4-carboxamide;
N-(3-cyano-5-fluorophenyl)-2-isobutyl-1-oxo-3-(pyridin-3-yl)-1,2,3,4-tetrahydroisoquinoline-4-carboxamide;
2-isobutyl-1-oxo-3-(pyridin-3-yl)-N-(3-(trifluoromethoxy)phenyl)-1,2,3,4-tetrahydroisoquinoline-4-carboxamide;
N-(4-fluoro-3-(trifluoromethoxy)phenyl)-2-isobutyl-1-oxo-3-(pyridin-3-yl)-1,2,3,4-tetrahydroisoquinoline-4-carboxamide;
N-(3-fluoro-5-(trifluoromethoxy)phenyl)-2-isobutyl-1-oxo-3-(pyridin-3-yl)-1,2,3,4-tetrahydroisoquinoline-4-carboxamide;
N-(3-cyanophenyl)-6-fluoro-2-isobutyl-3-(1-methyl-1H-pyrazol-4-yl)-1-oxo-1,2,3,4-tetrahydroisoquinoline-4-carboxamide;
N-(3-cyano-4-fluorophenyl)-3-(1-methyl-1H-pyrazol-4-yl)-1-oxo-2-(2,2,2-trifluoroethyl)-1,2,3,4-tetrahydroisoquinoline-4-carboxamide;
N-(3-chloro-5-cyanophenyl)-3-(1-methyl-1H-pyrazol-4-yl)-1-oxo-2-(2,2,2-trifluoroethyl)-1,2,3,4-tetrahydroisoquinoline-4-carboxamide;
N-(3-cyanophenyl)-3-(1-methyl-1H-pyrazol-4-yl)-1-oxo-2-(2,2,2-trifluoroethyl)-1,2,3,4-tetrahydroisoquinoline-4-carboxamide;
N-(3-cyano-5-fluorophenyl)-3-(1-methyl-1H-pyrazol-4-yl)-1-oxo-2-(2,2,2-trifluoroethyl)-1,2,3,4-tetrahydroisoquinoline-4-carboxamide;
3-(1-methyl-1H-pyrazol-4-yl)-1-oxo-2-(2,2,2-trifluoroethyl)-N-(3-(trifluoromethoxy)phenyl)-1,2,3,4-tetrahydroisoquinoline-4-carboxamide;
N-(4-fluoro-3-(trifluoromethoxy)phenyl)-3-(1-methyl-1H-pyrazol-4-yl)-1-oxo-2-(2,2,2-trifluoroethyl)-1,2,3,4-tetrahydroisoquinoline-4-carboxamide;
N-(3-fluoro-5-(trifluoromethoxy)phenyl)-3-(1-methyl-1H-pyrazol-4-yl)-1-oxo-2-(2,2,2-trifluoroethyl)-1,2,3,4-tetrahydroisoquinoline-4-carboxamide;
N-(3-cyano-4-fluorophenyl)-2-isobutyl-3-(1-methyl-1H-pyrazol-4-yl)-1-oxo-1,2,3,4-tetrahydroisoquinoline-4-carboxamide;
N-(3-chloro-5-cyanophenyl)-2-isobutyl-3-(1-methyl-1H-pyrazol-4-yl)-1-oxo-1,2,3,4-tetrahydroisoquinoline-4-carboxamide;
N-(3-cyanophenyl)-2-isobutyl-3-(1-methyl-1H-pyrazol-4-yl)-1-oxo-1,2,3,4-tetrahydroisoquinoline-4-carboxamide;
N-(3-cyano-5-fluorophenyl)-2-isobutyl-3-(1-methyl-1H-pyrazol-4-yl)-1-oxo-1,2,3,4-tetrahydroisoquinoline-4-carboxamide;
2-isobutyl-3-(1-methyl-1H-pyrazol-4-yl)-1-oxo-N-(3-(trifluoromethoxy)phenyl)-1,2,3,4-tetrahydroisoquinoline-4-carboxamide;
N-(4-fluoro-3-(trifluoromethoxy)phenyl)-2-isobutyl-3-(1-methyl-1H-pyrazol-4-yl)-1-oxo-1,2,3,4-tetrahydroisoquinoline-4-carboxamide;
N-(3-fluoro-5-(trifluoromethoxy)phenyl)-2-isobutyl-3-(1-methyl-1H-pyrazol-4-yl)-1-oxo-1,2,3,4-tetrahydroisoquinoline-4-carboxamide;
2-butyl-N-(3-cyano-4-fluorophenyl)-3-(5-cyanothiophen-2-yl)-1-oxo-1,2,3,4-tetrahydroisoquinoline-4-carboxamide;
N-(3-cyano-5-fluorophenyl)-6-fluoro-2-isobutyl-3-(1-methyl-1H-pyrazol-4-yl)-1-oxo-1,2,3,4-tetrahydroisoquinoline-4-carboxamide;
N-(3-cyano-4-fluorophenyl)-1-oxo-3-(1H-pyrazol-4-yl)-2-(2,2,2-trifluoroethyl)-1,2,3,4-tetrahydroisoquinoline-4-carboxamide;
N-(3-chloro-5-cyanophenyl)-1-oxo-3-(1H-pyrazol-4-yl)-2-(2,2,2-trifluoroethyl)-1,2,3,4-tetrahydroisoquinoline-4-carboxamide;
N-(3-cyanophenyl)-1-oxo-3-(1H-pyrazol-4-yl)-2-(2,2,2-trifluoroethyl)-1,2,3,4-tetrahydroisoquinoline-4-carboxamide;
N-(3-cyano-5-fluorophenyl)-1-oxo-3-(1H-pyrazol-4-yl)-2-(2,2,2-trifluoroethyl)-1,2,3,4-tetrahydroisoquinoline-4-carboxamide;
1-oxo-3-(1H-pyrazol-4-yl)-2-(2,2,2-trifluoroethyl)-N-(3-(trifluoromethoxy)phenyl)-1,2,3,4-tetrahydroisoquinoline-4-carboxamide;
N-(4-fluoro-3-(trifluoromethoxy)phenyl)-1-oxo-3-(1H-pyrazol-4-yl)-2-(2,2,2-trifluoroethyl)-1,2,3,4-tetrahydroisoquinoline-4-carboxamide;

N-(3-fluoro-5-(trifluoromethoxy)phenyl)-1-oxo-3-(1H-pyrazol-4-yl)-2-(2,2,2-trifluoroethyl)-1,2,3,4-tetrahydroisoquinoline-4-carboxamide;

N-(3-cyano-4-fluorophenyl)-7-fluoro-2-isobutyl-3-(1-methyl-1H-pyrazol-4-yl)-1-oxo-1,2,3,4-tetrahydroisoquinoline-4-carboxamide;

N-(3-cyano-4-fluorophenyl)-2-isobutyl-1-oxo-3-(1H-pyrazol-4-yl)-1,2,3,4-tetrahydroisoquinoline-4-carboxamide;

N-(3-chloro-5-cyanophenyl)-2-isobutyl-1-oxo-3-(1H-pyrazol-4-yl)-1,2,3,4-tetrahydroisoquinoline-4-carboxamide;

N-(3-cyanophenyl)-2-isobutyl-1-oxo-3-(1H-pyrazol-4-yl)-1,2,3,4-tetrahydroisoquinoline-4-carboxamide;

N-(3-cyano-5-fluorophenyl)-2-isobutyl-1-oxo-3-(1H-pyrazol-4-yl)-1,2,3,4-tetrahydroisoquinoline-4-carboxamide;

2-isobutyl-1-oxo-3-(1H-pyrazol-4-yl)-N-(3-(trifluoromethoxy)phenyl)-1,2,3,4-tetrahydroisoquinoline-4-carboxamide;

N-(4-fluoro-3-(trifluoromethoxy)phenyl)-2-isobutyl-1-oxo-3-(1H-pyrazol-4-yl)-1,2,3,4-tetrahydroisoquinoline-4-carboxamide;

N-(3-fluoro-5-(trifluoromethoxy)phenyl)-2-isobutyl-1-oxo-3-(1H-pyrazol-4-yl)-1,2,3,4-tetrahydroisoquinoline-4-carboxamide;

N-(3-chloro-5-cyanophenyl)-7-fluoro-2-isobutyl-3-(1-methyl-1H-pyrazol-4-yl)-1-oxo-1,2,3,4-tetrahydroisoquinoline-4-carboxamide;

N-(3-cyano-4-fluorophenyl)-2-isobutyl-3-(isothiazol-4-yl)-1-oxo-1,2,3,4-tetrahydroisoquinoline-4-carboxamide;

N-(3-cyano-4-fluorophenyl)-2-isobutyl-1-oxo-3-(pyrimidin-5-yl)-1,2,3,4-tetrahydroisoquinoline-4-carboxamide; or N-(3-cyano-4-fluorophenyl)-1-oxo-3-(1H-pyrazol-4-yl-6,7-difluoro-2-(2,2,2-trifluoroethyl)-1,2,3,4-tetrahydroisoquinoline-4-carboxamide.

\* \* \* \* \*